United States Patent [19]

Ort et al.

[11] Patent Number: 5,324,710

[45] Date of Patent: Jun. 28, 1994

[54] SULFONATED HETEROCYCLIC CARBOXAMIDES AND THEIR USE AS HERBICIDES, AND GROWTH REGULATORS

[75] Inventors: Oswald Ort, Kelkheim; Lothar Willms, Hillscheid; Klaus Bauer, Hanau; Hermann Bieringer, Eppstein; Arno Schulz, Hattersheim am Main; Burkhard Sachse, Kelkheim; Peter Braun, Mainz, all of Fed. Rep. of Germany

[73] Assignee: Hoechst Aktiengesellschaft, Frankfurt am Main, Fed. Rep. of Germany

[21] Appl. No.: 849,034

[22] PCT Filed: Oct. 18, 1990

[86] PCT No.: PCT/EP90/01768
§ 371 Date: Apr. 21, 1992
§ 102(e) Date: Apr. 21, 1992

[87] PCT Pub. No.: WO91/06541
PCT Pub. Date: May 16, 1991

[30] Foreign Application Priority Data

Oct. 24, 1989 [DE] Fed. Rep. of Germany ....... 3935277

[51] Int. Cl.$^5$ ............... A01N 43/54; C07D 239/26; C07D 401/12; C07D 401/14
[52] U.S. Cl. ................... 504/239; 504/242; 504/243; 544/122; 544/123; 544/82; 544/69; 544/229; 544/310; 544/311; 544/316; 544/317; 544/319; 544/320; 544/321; 544/323; 544/324; 544/327; 544/331; 544/332; 544/333; 544/334; 544/335
[58] Field of Search ............... 71/92; 544/310, 311, 544/316, 317, 319, 320, 321, 323, 324, 327, 331, 332, 333, 334, 335, 122, 123, 82, 69, 229; 504/239, 242, 243

[56] References Cited

U.S. PATENT DOCUMENTS 2,876,224 3/1959 Grant et al. ................... 260/256.4

FOREIGN PATENT DOCUMENTS 0162538 11/1985 European Pat. Off. .
0353640 2/1990 European Pat. Off. .
1445155 10/1968 Fed. Rep. of Germany .
3243590 5/1984 Fed. Rep. of Germany .

Primary Examiner—John M. Ford
Attorney, Agent, or Firm—Curtis, Morris & Safford

[57] ABSTRACT

Compounds of the formula I or their salts

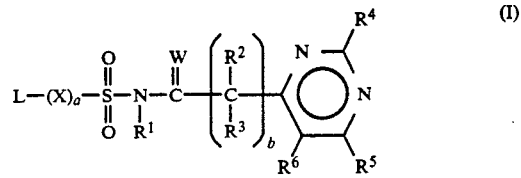

in which
$R^1$ to $R^6$, W, X, a and b are as defined in claim 1 and L is a heterocyclic or isocyclic aromatic radical having 5 to 6 ring atoms, which can be condensed with an aromatic or non-aromatic 5- or 6-membered ring, where the radical can be unsubstituted or substituted, and a, b and c independently of one another are 0 or 1, are suitable as herbicides, plant growth regulators and fungicides. They can be prepared by the processes defined herein, it being possible in some cases to use novel intermediates.

13 Claims, No Drawings

SULFONATED HETEROCYCLIC CARBOXAMIDES AND THEIR USE AS HERBICIDES, AND GROWTH REGULATORS

It is already known that certain sulfonylated bi- or tricyclic heteroaromatic carboxamides have herbicidal and growth-regulatory properties (EP-A-244,166). Sulfonylated monocyclic pyridinecarboxamides have been described as fungicides and microbiocides [sic] in agriculture (Chem. Abstr. 108 (19): 167298p; Chem. Abstr. 108 (15): 131590p). A herbicidal action of these compounds has not been disclosed.

It has already been proposed to employ sulfonated 2-pyrimidinylcarboxamides [sic] and 2-triazinylcarboxamides as herbicides and growth regulators (see German Patent Application P 38 26 230.4 or EP-A-353,640).

It has now been fond that sulfonated 4-pyrimidinylcarboxamides have advantageous herbicidal, growth-regulatory and fungicidal properties.

The present invention relates to compounds of the formula I or their salts

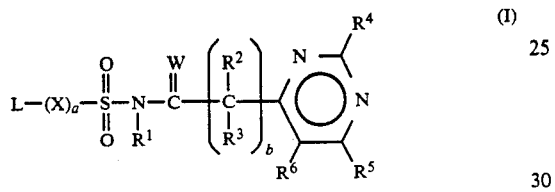

(I)

in which $R^1$ is hydrogen, $(C_1-C_4)$alkyl, $(C_2-C_6)$alkenyl or $(C_2-C_6)$-alkynyl $R^2$, $R^3$ independently of one another are hydrogen, $(C_1-C_3)$-alkyl or phenyl;

W is O, S, $NR^7$ or $NOR^7$;

X is $CHR^2$, O, $NR^7$ or $NOR^7$;

$R^4$, $R^5$ independently of one another are hydrogen, hydroxyl, halogen, $(C_1-C_6)$alkyl, $(C_1-C_6)$alkoxy or $(C_1-C_6)$alkylthio, where the three abovementioned radicals can be monosubstituted or polysubstituted by halogen or monosubstituted or disubstituted by $(C_1-C_4)$alkoxy or $(C_1-C_4)$alkylthio; $-NR^8R^9$, $(C_3-C_6)$-cycloalkyl, $-OCHR^8CO_2R^{10}$, $(C_2-C_5)$alkenyl, $(C_2-C_4)$-alkynyl, $(C_3-C_5)$alkenyloxy or $(C_3-C_5)$alkynyloxy;

$R^6$ is hydrogen, halogen, $(C_1-C_3)$alkyl, $(C_1-C_3)$alkoxy, $-CN$, $-NO_2$, $-CO-R^{11}$, $-CO_2R^{12}$, $(C_1-C_3)$alkylthio, $-SO-R^{12}$, $-SO_2-R^{12}$ or $-CO-NR^8R^9$;

$R^7$ is hydrogen, $(C_1-C_3)$alkyl, $(C_1-C_3)$haloalkyl or phenyl;

$R^8$ is hydrogen or $(C_1-C_4)$alkyl or $R^8$ and $R^9$ together are $-(CH_2)_2(CH_2)_c(CH_2)_2-$ or $-(CH_2)_2O(CH_2)_2-$;

$R^9$ is hydrogen, $(C_1-C_4)$alkyl, $(C_1-C_4)$alkoxy, $(C_2-C_4)$alkenyl or $R^8$ and $R^9$ together are $-(CH_2)_2(CH_2)_c(CH_2)_2$ or $-(CH_2)_2O(CH_2)_2-$;

$R^{10}$ is hydrogen, $(C_1-C_4)$alkyl which is unsubstituted, or monosubstituted or polysubstituted by halogen or monosubstituted or disubstituted by CN, $CO_2-R^{12}$, $-NR^8R^9$, $OR^{12}$ or $Si(CH_3)_3$; $(C_3-C_4)$alkynyl or $(C_3-C_4)$-alkenyl, where the two abovementioned radicals are unsubstituted or substituted by $CH_3$ or $-Si(CH_3)_3$; $(C_3-C_6)$cycloalkyl which is unsubstituted or substituted by $(C_1-C_4)$alkyl or $(C_1-C_4)$alkoxy; or $Si(CH_3)_3$;

$R^{11}$ is hydrogen, $(C_1-C_4)$alkyl, $(C_1-C_4)$alkyl which is monosubstituted or polysubstituted by halogen or $(C_1-C_3)$alkoxy; $(C_3-C_6)$cycloalkyl which is unsubstituted, or monosubstituted or polysubstituted by halogen, such as, for example, F, Cl and Br, or $CH_3$, $(C_2-C_4)$alkenyl or $(C_2-C_4)$alkynyl;

$R^{12}$ is $(C_1-C_3)$alkyl;

L is a heterocyclic or isocyclic aromatic radical having 5 to 6 ring atoms, which can be condensed with an aromatic or non-aromatic 5- or 6-ring, the radical being unsubstituted or substituted, and a, b and c independently of one another are 0 or 1.

Of particular interest are compounds according to the invention of the formula (I) or their salts in which L is a hetero- or isocyclic radical of the formulae (L1) to (L5)

(L1)

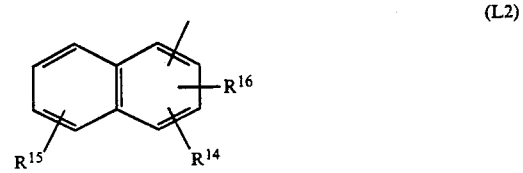

(L2)

(L3)

(L4)

(L5)

$R^{13}$ is hydrogen, halogen, $NO_2$, CN, $(C_1-C_4)$alkyl which is unsubstituted, or monosubstituted or polysubstituted by halogen, such as, for example, F, Cl and Br, or monosubstituted by CN, $OCH_3$ or $SCH_3$; $(C_2-C_4)$alkenyl which is unsubstituted, or monosubstituted or polysubstituted by halogen, such as, for example, F, Cl and Br, or monosubstituted by $OCH_3$; $(C_2-C_4)$alkynyl which is unsubstituted, or monosubstituted or polysubstituted by halogen, such as, for example, F, Cl and Br, or monosubstituted by $OCH_3$ or $Si(CH_3)_3$; $(C_3-C_6)$cycloalkyl which is unsubstituted, or monosubstituted or polysubstituted by halogen, such as, for example, F and Cl, or $CH_3$; $-CO-R^{11}$, $-OCH_2CH_2OR^{11}$, $-OH$, $-C(R^{11})(OR^{17})(OR^{18})$; $-CO_2R^{10}$, $-CO-NR^8R^9$, $-N_3$, $-SO_2NR^8R^9$, $-SO_3R^{19}$, $-OSO_2R^{20}$; phenyl which is unsubstituted or monosubstituted or polysubstituted by halogen, such as, for example F, Cl and Br, $CH_3$ or $OCH_3$; —E—$R^{21}$ or —$(CH_2)_0$—G;

$R^{14}$ is hydrogen, halogen; CN, $NO_2$, $(C_1$-$C_4)$-alkyl which is unsubstituted, or monosubstituted or polysubstituted by halogen or monosubstituted or disubstituted by —$CO_2R^{10}$, —$SO_2NR^8R^9$, —$NR^8R^9$, $(C_1$-$C_2)$alkoxy, —E—$R^{22}$, $(C_1$-$C_2)$haloalkoxy, $(C_1$-$C_2)$alkylthio, $(C_1$-$C_2)$haloalkylthio, —CN, —OH or SH; —$CO_2R^{10}$, —$SO_2NR^8R^9$, —$NR^8R^9$ or —E—$R^{22}$;

$R^{15}$ is hydrogen, $(C_1$-$C_4)$alkyl, $(C_1$-$C_4)$haloalkyl, $(C_2$-$C_4)$-alkenyl, phenyl or phenyl which is monosubstituted or polysubstituted by halogen or —E—$R^{22}$; —E—$R^{22}$ or halogen;

$R^{16}$ is hydrogen, $(C_1$-$C_4)$alkyl, $(C_1$-$C_4)$haloalkyl, halogen, —$CO_2R^{10}$, —$SO_2NR^8R^9$, —$OSO_2R^{20}$, —E—$R^{22}$, —CN or —$NO_2$;

E, Z independently of one another are O or $S(O)_f$;
a, b, c, d, e independently of one another are 0 or 1;
f is 0, 1 or 2;

$R^{17}$, $R^{18}$ independently of one another are $(C_1$-$C_4)$alkyl, or $R^{17}$ and $R^{18}$ together are —$CH_2CH_2$—, —$CH_2OCH_2$— or —$CH_2$—$C(CH_3)_2CH_2$—;

$R^{19}$ is $(C_1$-$C_4)$alkyl or $(C_1$-$C_4)$haloalkyl,
$R^{20}$ is $(C_1$-$C_4)$alkyl, —$NR^8R^9$ or $(C_1$-$C_4)$haloalkyl,
$R^{21}$ is $(C_1$-$C_4)$alkyl, $(C_1$-$C_4)$haloalkyl, $(C_2$-$C_4)$alkoxyalkyl, $(C_2$-$C_4)$alkenyl, $(C_3$-$C_4)$alkynyl, phenyl or phenyl which is monosubstituted or polysubstituted by halogen $(C_1$-$C_3)$alkyl, $(C_1$-$C_3)$alkoxy or $(C_1$-$C_3)$haloalkyl; or $(C_2$-$C_4)$haloalkenyl;

$R^{22}$ is $(C_1$-$C_4)$alkyl or $(C_1$-$C_4)$alkyl which is monosubstituted or polysubstituted by F, Cl or monosubstituted by $OR^{19}$;

$R^{23}$ is hydrogen, $(C_1$-$C_4)$alkyl which is unsubstituted, or monosubstituted or polysubstituted by halogen or monosubstituted by phenyl, or $(C_2$-$C_4)$alkenyl, phenyl or phenyl which is monosubstituted or polysubstituted by halogen, $(C_1$-$C_4)$alkyl, $(C_1$-$C_4)$haloalkyl, —$NO_2$, —CN or $(C_1$-$C_4)$alkoxy, and G is a heterocyclic saturated or unsaturated, unsubstituted or substituted radical having 5 or 6 ring atoms which has 1 to 4 hetero ring atoms from the group comprising N, O and S, and preferably up to 4 nitrogen atoms and up to one oxygen or sulfur atom as hetero ring atoms, and $R^1$ to $R^{12}$, W and X have the abovementioend meaning.

Of particular interest are compounds according to the invention of the formula (I) or their salts in which G is a heterocyclic radical from the group of radicals of the formulae (G1)–(G25);

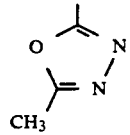

(G1)

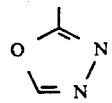

(G2)

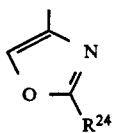 (G15)

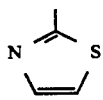 (G16)

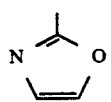 (G17)

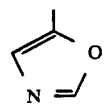 (G18)

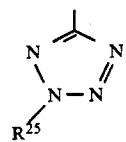 (G19)

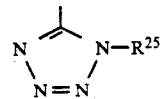 (G20)

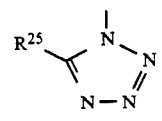 (G21)

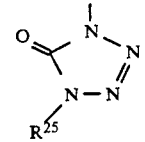 (G22)

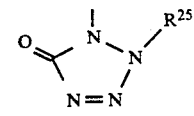 (G23)

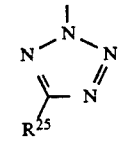 (G24)

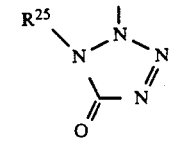 (G25)

and
$R^{24}$ is hydrogen or $(C_1-C_4)$alkyl and
$R^{25}$ is hydrogen, $(C_1-C_3)$alkyl or $(C_2-C_4)$alkenyl.

The compound [sic] of the formula I can contain one or more chirality centers and are then present as diastereomer or enantiomer mixtures. The invention includes both the pure enantiomers or diastereomers and their mixtures.

If $R^1$=H, the compounds of the formula I can form salts in which the hydrogen of the —$SO_2$—NH group is replaced by a cation suitable for agriculture. These salts are in general metal, in particular alkali metal, alkaline earth metal, optionally alkylated ammonium or organic amine salts. They are preferably prepared in inert solvents such as, for example, water, methanol or acetone at temperatures of 0°-100° C. Suitable bases for the preparation of the salts according to the invention are, for example, alkali metal carbonates, such as potassium carbonate, alkali metal and alkaline earth metal hydroxides, ammonia or ethanolamine.

The compounds of the formula (I) which contain nitrogen-containing heterocycles can additionally form salts with inorganic or organic acids. Suitable acids for the preparation of the acid addition salts according to the invention are, for example, inorganic acids such as HCl, $H_2SO_4$ and $H_3PO_4$ or organic acids such as formic acid, acetic acid, palmitic acid, trichloroacetic acid or 4-toluenesulfonic acid.

In the abovementioned definitions, the expression "alkyl", on its own or in combined words such as "alkylthio", "haloalkyl", "alkylamino" or "bisalkylamino", is in each case straight-chain or branched alkyl.

Alkenyl is similarly straight- or branched-chain alkenyl, for example 1-propenyl, 2-propenyl or 3-propenyl. Alkynyl is straight- or branched-chain alkynyl, for example ethynyl, 1-propynyl, 2-propynyl or the various butynyl isomers. Alkylsulfonyl is, for example, methylsulfonyl, ethylsulfonyl or the various propylsulfonyl isomers.

The expression "halogen", alone or in combined words such as "haloalkyl", is fluorine, chlorine, bromine or iodine. Furthermore, in combined words such as "haloalkyl", said alkyl is partially or completely halogenated. Examples of haloalkyl are $CHF_2$, $CH_2CH_2F$, $CF_2CF_3$ and $CH_2CHFCl$. Preferred compounds of the general formula I are those ni which L is a radical of the formulae (L1), (L3), (L4) or (L5);
X is $CH_2$, $CH(CH_3)$, O, NH, $NCH_3$, $NC_2H_5$, $NOCH_3$, in particular $CH_2$, O or NH;
W is oxygen;
$R^1$ is hydrogen;
$R^2$, $R^3$ independently of one another are hydrogen or $(C_1-C_3)$alkyl, in particular hydrogen;
$R^4$, $R^5$ independently of one another are hydrogen, $(C_1-C_2)$-alkyl, $(C_1-C_2)$alkoxy, —$OCH_2OCH_3$, —$CH_2OCH_3$, F, Cl, Br, I, —$CH_2OCH_2CH_3$, —$NHCH_3$, —$N(CH_3)_2$, —$N(CH_3(OCH_3)$, —$CF_3$, —$SCH_3$, —$CH(OCH_3)_2$, —$OCH_2CH$=$CH_2$, —$OCH_2C$≡$CH$, —$OCH_2CH_2OC$—$H_3$, —$CH_2SCH_3$, —$OCHF_2$, —$SCHF_2$, cyclopropyl, —C≡CH or —C≡C—$CH_3$;
$R^6$ is hydrogen, halogen, —$CH_3$, —$OCH_3$, —$NO_2$, —CN, —CHO, —$CO_2CH_3$, $CO_2C_2H_5$ or —$SCH_3$, in particular hydrogen, halogen, —$NO_2$, —CN, —CHO, —$CO_2CH_3$ or —$CO_2C_2H_5$;
$R^8$ is hydrogen or —$CH_3$ or $R^8$ and $R^9$ together are —$(CH_2)_4$—, —$(CH_2)_5$— or —$(CH_2)_2O(CH_2)_2$—;
$R^9$ is —$CH_3$, —$CH_2CH_3$, —$OCH_3$ or $R^8$ and $R^9$ together are —$(CH_2)_4$—, —$(CH_2)_5$— or —$(CH_2)_2O(CH_2)_2$—;

$R^{10}$ is $(C_1-C_3)$alkyl, $(C_3)$alkenyl, $(C_3)$alkynyl, —CH$_2$CH$_2$F, —CH$_2$CH$_2$Cl, —CH$_2$CH$_2$OCH$_3$, —CH$_2$CH$_2$Si(CH$_3$)$_3$ or cyclopropylmethyl;

$R^{11}$ is $(C_1-C_3)$alkyl, hydrogen, cyclopropyl or $(C_3)$alkenyl;

$R^{12}$ is —CH$_3$, —CH$_2$CH$_3$, —CH$_2$CH$_2$CH$_3$ or —CH(CH$_3$)$_2$;

$R^{13}$ is halogen, —NO$_2$, —CN, $(C_1-C_3)$alkyl which is unsubstituted or substituted by F, Cl, Br, CN, OCH$_3$ or SCH$_3$; $(C_3)$alkenyl which is unsubstituted or substituted by F, Cl or Br, $(C_3)$alkynyl, cyclopropyl which is unsubstituted or substituted by F, Cl or CH$_3$; —C(O)R$^{11}$, —OCH$_2$CH$_2$OR$^{11}$, —OH, C(R$^{11}$)(OR$^{17}$)(OR$^{18}$), —CO$_2$R$^{10}$, —CO—NR$^8$R$^9$, —N$_3$, —SO$_2$NR$^8$R$^9$, —OSO$_2$R$^{20}$, —E —R$^{21}$ or —(CH$_2$)$_e$G;

$R^{14}$ is hydrogen, halogen, —CN, —NO$_2$, —CH$_3$, —CF$_3$, —E—R$^{22}$, or $(C_1-C_2)$alkoxy-$(C_1-C_2)$alkyl, $(C_1-C_2)$haloalkoxy, $(C_1-C_2)$alkylthio, $(C_1-C_2)$haloalkylthio, —CO$_2$R$^{10}$ or SO$_2$NR$^8$R$^9$;

$R^{15}$ is hydrogen;

$R^{17}$, $R^{18}$ independently of one another are $(C_1-C_2)$alkyl or $R^{17}$ and $R^{18}$ together are —CH$_2$CH$_2$—;

$R^{19}$ is $(C_1-C_3)$alkyl;

$R^{20}$ is $(C_1-C_3)$alkyl or $(C_1-C_3)$haloalkyl;

$R^{21}$ is $(C_1-C_3)$alkyl, $(C_1-C_3)$haloalkyl, $(C_2-C_3)$alkoxyalkyl, allyl, propargyl or $(C_2-C_3)$haloalkenyl;

$R^{22}$ is $(C_1-C_2)$alkyl which is unsubstituted or substituted by F, Cl or OCH$_3$;

$R^{23}$ is hydrogen, $(C_1-C_3)$alkyl, phenyl or phenyl which is monosubstituted or polysubstituted by halogen, —NO$_2$, $(C_1-C_3)$alkyl, $(C_1-C_3)$haloalkyl or $(C_1-C_3)$alkoxy;

$R^{24}$ is hydrogen or $(C_1-C_3)$alkyl;

$R^{25}$ is hydrogen or $(C_1-C_3)$alkyl;

Z is S;

d is O;

e is O;

and E, a, b, f and G are as defined above.

For $R^4$ and $R^5$, particularly preferred radicals independently of one another are hydrogen, —CH$_3$, —OCH$_3$, —CH$_2$CH$_3$, —OCH$_2$CH$_3$, —OCHF$_2$, —OCH$_2$OCH$_3$, —CH$_2$OCH$_3$, —NHCH$_3$, —CH(OCH$_3$)$_2$, —Cl or cyclopropyl.

The present invention also relates to processes for the preparation of the compound of the formula I and its salts, wherein a) for the preparation of compounds where W=O a$_1$) a compound of the formula II

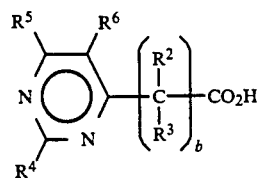

(II)

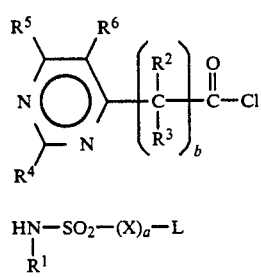

(III)

is reacted with a compound of the formula III in the presence of a base or a$_2$) a compound of the formula (IIa)

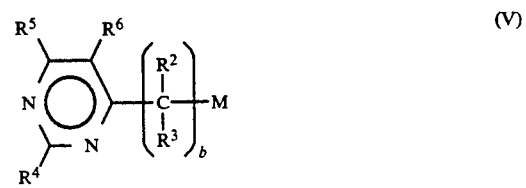

(IIa)

is reacted in the presence of activating reagents, such as 2-chloro-1-methylpyridinium chloride (IVa), dicyclohexylcarbodiimide (IVb) or 1,1-carbonyldiimidazole (IVc), and optionally in the presence of a base with a compound of the formula III or a$_3$) for the preparation of compounds where W=O and $R^1$=H, a compound of the formula (V)

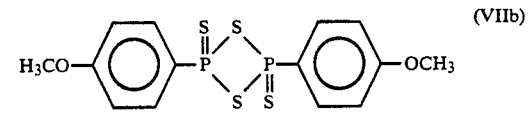

(V)

$$O=C=N-\overset{\overset{O}{\|}}{\underset{\underset{O}{\|}}{S}}-(X)_a-L$$ (VI)

in which M is hydrogen (for b=O) or lithium is reacted with a compound of the formula (VI) or b) for the preparation of compounds where W=S, a compound of the formula I obtained under a) is reacted with P$_4$S$_{10}$(VIIa) or the compound of the formula VIIb

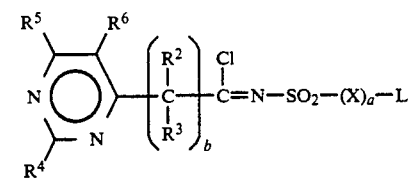

(VIIb)

c) for the preparation of compounds where W=NR$^7$, a compound of the formula VIII

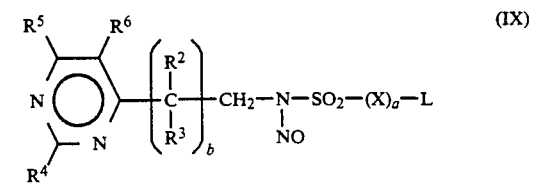

(VIII)

is reacted with an amine of the formula H$_2$N—R$^7$, d) for the preparation of compounds where W=NOR$^7$ d$_1$) a compound of the formula IX (IX)

is reacted with an alkali metal or alkaline earth metal hydroxide or ammonium hydroxide or d2) a compound of the formula VIII is reacted in the presence of a base with a hydroxylamine of the formula H₂NOR⁷ or e) for the preparation of compounds of the formula I in which R¹ is not equal to hydrogen, a compound of the formula I where R¹=H is reacted in the presence of a base with an alkyl halide of the formula R¹'—X¹, in which R¹' has the meaning of R¹ apart from hydrogen and X¹ is chlorine, bromine or iodine.

The acid chloride of the formula II employed in process a₁) can be prepared in a known manner from the corresponding carboxylic acid of the formula IIa or its salt with inorganic acid chlorides such as thionyl chloride or with oxalyl chloride in the presence of suitable bases, i particular organic nitrogen bases, such as pyridine, 2,6-lutidine or triethylamine and/or catalysts such as N,N-4-dimethylaminopyridine or dimethylformamide and is expediently reacted with the component III in the presence of said base directly without intermediate isolation. Excess thionyl chloride or oxalyl chloride is distilled off before the reaction of the acid chloride II with the sulfonamide III.

The reactions according to process variant a₂) are known per se. They are preferably carried out in an inert aprotic solvent, such as dichloromethane, 1,2-dichloroethane, acetonitrile or glycol dimethyl ether at temperatures between −30° C. to 83° C. Bases used are, for example, organic nitrogen bases such as pyridine, triethylamine etc. In the case of carbonyldiimidazole, no addition of base is necessary.

Process a₃) is known per se; it is preferably carried out in an inert aprotic solvent such as dichloromethane, tetrahydrofuran, 1,2-dichloroethane or glycol dimethyl ether in the temperature range from −78° C. to 85° C.

The process according to variant b) is likewise known per se; it is preferably carried out in an inert aprotic solvent such as toluene or xylene at temperatures between 0° and 145° C. In cases in which the products are insoluble in the reaction medium, they can be isolated by simple filtration. If the reaction products are soluble, they can be obtained by crystallization or chromatography of the residue after evaporating off the solvent.

Process variants c) and d) are known in principle. Processes c) and d₂) are preferably carried out in an inert aprotic solvent such as dichloroethane or toluene in the temperature range between 0° C. and 110° C.

The imidoyl chlorides of the formula VIII can be obtained from a compound of the formula I prepared according to variant a) by reaction with triphenylphosphine/tetrachloromethane or PCl₅/POCl₃. The process is preferably carried out in CCl₄ or POCl₃ at temperatures between 0° C. and 105° C., cf. Houben-Weyl, Vol. E5/1, pp. 628–632 (1985); Vol. 5/3 pp. 916–922 and Vol. 8 pp. 345, 673–76.

Process e), which is known per se, is preferably carried out in an inert aprotic solvent such as dichloromethane, tetrahydrofuran, 1,2-dichloroethane or glycol dimethyl ether in the temperature range from −78° C. to 85°.

The carboxylic acids of the formula (IIa) corresponding to the acid chlorides of the formula (II) can be prepared by various methods. A possible method is, for example, the alkaline hydrolysis of the corresponding carboxylic acid esters (J. March "Advanced Organic Chemistry", 3rd edition, John Wiley & Sons, N.Y. 1985, pages 334–338), or the reaction of the ester compounds with lithium iodide in pyridine or other amines or with trimethylsilyl chloride and sodium iodide (cf. J. March, "Advanced Organic Chemistry" 3rd edition, John Wiley & Sons, N.Y. 1985, page 386) or by [sic] reaction with iodotrimethylsilane, see Olah, Narany, Tetrahedron 38, 2225–2277 (1982) or by [sic] reaction with hydrobromic acid.

The carboxylic acids (IIa) can additionally be prepared from the corresponding nitriles by hydrolysis, see Monatsh. Chem. 87, 526–35 (1956) or conversion into the imidoether and subsequent hydrolysis, see T. Sakamoto; Chem. Pharm. Bull. 28, 3362–8 (1980).

In addition, the carboxylic acids (IIa) can be prepared from the corresponding benzyl esters by hydrogenation in the presence of a catalyst such as palladium, see Houben-Weyl, "Methoden der organischen Chemie" (Methods of Organic Chemistry), Vol. 4/1c (1980), pp. 379–387.

Alternatively to this, the carboxylic acids of the formula IIa can be obtained from the halogenated heterocycles of the formula (IIb)

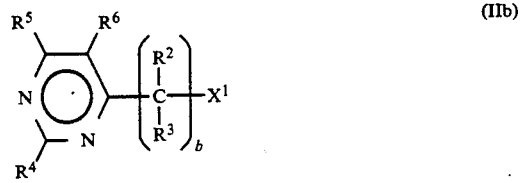

by reaction with carbon dioxide directly—cyanides or indirectly via organometallic intermediates, see Volpin and Kolomnikov, Organomet. React. 5, 313–386 (1975); Langley, J. Am. Chem. Soc. 78, 2136 (1956); Sneeden, in Patai "The Chemistry of Carboxylic Acids and Esters", pp. 137–173, Interscience, N.Y. 1969; and Kharasch and Reinmuth, "Grignard Reactions of Nonmetallic Substances", pp. 913–948, Prentice-Hall, Englewood Cliffs, N.Y. 1954.

The nitriles on which the carboxylic acids IIa are based can be prepared from the compounds of the formula (IIc)

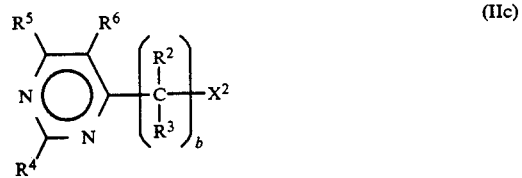

by reaction with alkali metal cyanides or tetraalkylammonium cyanides. In the formula (IIc, X² is a leaving group such as chlorine, bromine, iodine, p-tosyl, OSO₂C₃ or tetraalkylammonium, see K. Klötzer, Monatsh. Chem. 78, 526–35 (1956); Sakamoto, Chem. Pharm. Bull. 28, 3362–8 (1980); J. March, "Advanced Organic Chemistry", 3rd edition, John Wiley & Sons, N.Y. 1985, pp. 594–595; Houben-Weyl, Vol. E5/2, pp. 1447–1474 (1985); K. Hermann, Liebigs Ann. Chem. 1981, 333–41; Hurst, D. T.; Heterocycles 6, 2005–15 (1977).

Alternatively to this, the nitrile compounds can be prepared by reaction of heterocyclic N-oxides with trimethylsilyl cyanide, see H. Yamanaka, Synthesis 1984, 681–3; and H. Vorbrüggen, Synthesis 1983, 316–9; Houben-Weyl, Vol. E5/2, pp. 1444–1446 (1985).

In addition, the nitriles can be prepared from the corresponding aminopyrimidines according to the Sandmeyer reaction, i.e. by diazotization and subsequent reaction with copper(II) cyanide.

The halogenated heterocycles of the formula (IIb) can be prepared by halogenation of the corresponding alkylated heterocyclic N-oxides, see Craig, J. Org. Chem. 1970 (35), 1721; Bauer, J. Org. Chem. 1963 (28), 1323; Hunt, J. Chem. Soc. 525–530 (1959) and Matsumura, Nippon Kagaku Zasshi 74, 363 (1953).

In addition, the halogenated heterocycles of the formula IIb can be obtained from the corresponding hydroxy compounds of the formula IId by reaction with halogenating reagents, such as thionyl chloride or phosphorus oxychloride, see Angerstein, Ber. dtsch. Chem. Ges. 34, 3956 (1901); d'Atri, J. Med. Chem. 1984 (27), 1621–1629 or Sakamoto, Chem. Pharm. Bull. 28, 3362–8 (1980).

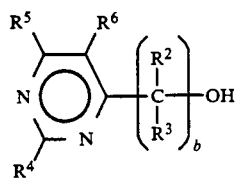
(IId)

Or if b=O by reaction of the corresponding aminopyrimidinea in a Sandmeyer-like reaction, see Tagaki, Chem. Pharm. Bull. 11, 1382 (1963); Houben-Weyl, "Methoden der organischen Chemie" (Methods of Organic Chemistry), Vol. 10/3, 53 et seq., Georg Thieme Verlag, Stuttgart 1965, Vol. 5/3, 846 et seq. and Vol. 5/4, 437 et seq.

The heterocyclic amines are known or can be prepared by processes known in principle, see "The Chemistry of Heterocyclic Compounds", Vol. XVI, (1962), Interscience Publ. N.Y. & London, and Supplement I (1970) of this reference book.

Pyrimidinecarboxylic acid derivatives which can be used as intermediates, of the general formula IIe

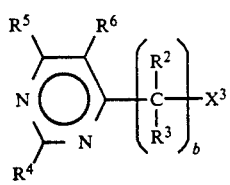
(IIe)

in which
R$^4$ and/or R$^5$ are (C$_1$–C$_6$)alkoxy, (C$_1$–C$_6$)alkylthio, NR$^8$R$^9$, hydroxyl or halogen and X$^3$ is —CO—Hal, CN, CO$_2$H, CO$_2$R$^{10}$ or CO$_2$CH$_2$C$_6$H$_5$ and R$^2$, R$^3$, R$^6$, R$^8$, R$^9$, R$^{10}$ and b have the meanings already mentioned, can be prepared, for example, as follows:

alkoxy-, alkylthio- and amino-substituted derivatives (formula IIe, R$^4$ and/or R$^5$=(C$_1$–C$_6$)alkoxy, (C$_1$–C$_6$)alkylthio or NR$^8$R$^9$) can be prepared from the appropriate halogenated pyrimidinecarboxylic acid derivatives (formula IIe, R$^4$ and/or R$^5$=halogen) by reaction with the corresponding (C$_1$–C$_6$)alcohols, (C$_1$–C$_6$)alkylmercaptans or amines HNR$^8$R$^9$ in the presence or absence of equivalent amounts of alcoholate, mercaptide or amide or another suitable auxiliary base; see H. Gershon, J. Org. Chem. 27, pp. 3507–3510 (1962); G. D. Daves, J. Org. Chem. 26, pp. 2755–2763 (1961).

The abovementioned halogenated pyrimidinecarboxylic acid derivatives (formula IIe, R$^4$ and/or R$^5$=halogen; and X$^3$, R$^2$, R$^3$, R$^6$ and b with said meanings) can be prepared b reaction of the corresponding hydroxypyrimidines (formula IIe; R$^4$ and/or R$^5$=hydroxyl) with halogenating reagents such as, for example, POCl$_3$, PCl$_5$ or SOCl$_2$, if desired in the presence of an auxiliary base such as, for example, pyridine or an N,N-dialkylamine; see H. Gershon, J. Org. Chem. 27, pp. 3507–2510 (1962); G. D. Daves, J. Org. Chem. 26, pp. 2755–2763 (1961); Z. Budesinsky, Coll. Czechoslov. Chem. Commun. 26, 2871–2885 (1961). Alternatively, the compounds of the formula IIe [lacuna] where R$^4$ and/or R$^5$=halogen can be obtained by reaction of the corresponding aminopyrimidines (formula IIe) [lacuna] R$^4$ and/or R$^5$=amino in a Sandmeyer-like reaction; see Tagaki, Chem. Pharm. Bull. 11, pp. 1382–8 (1963).

Alkoxy-substituted pyrimidinecarboxylic acid derivatives (formula IIe, R$^4$ and/or R$^5$=C$_1$–C$_6$-alkoxy) can also be prepared from the abovementioend corresponding hydroxypyrimidines (formula IIe, R$^4$ and/or R$^5$=OH) by reaction with alkylating reagents such as dialkyl sulfate, alkyl halides, alkylsulfonates or trialkyloxonium salts (Meerwein salts).

Said hydroxypyrimidines (formula IIe, R$^4$ and/or R$^5$=OH) can be prepared by condensation of compounds of the formula

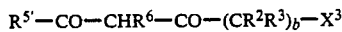

or

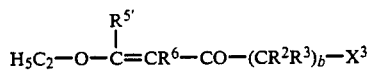

in which
R$^{5'}$ is alkoxy or alkyl and b, X$^3$ and R$^6$ have said meanings, preferably b=O and X$^3$=CO$_2$R$^{10}$ or CO$_2$CH$_2$C$_6$H$_5$, with amidines or ureas of the formula

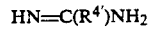

in which
R$^{4'}$ is alkyl, alkoxy or hydroxyl, in the presence of a catalytic or equivalent amount of an acid, such as, for example, hydrochloric acid, or a base, such as, for example, sodium hydroxide solution in aqueous or alcoholic medium, see Budesinsky, Colletc. Czechoslov. Chem. Commun. 26, 2871 (1961); A. Pinner, Chem. Ber. 25, 1414 (1892).

Alternatively to this, certain hydroxypyrimidines (formula IIe, R$^5$=OH, R$^4$=hydrogen or alkyl, R$^6$=hydrogen or halogen, X$^3$=CO$_2$R$^{10}$ or CO$_2$CH$_2$C$_6$H$_5$ and b=O) can be obtained by oxidative cyclization of alkylideneasparagines of the formula

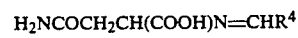

with hypohalites or potassium permanganate, see Cherbuliez, Helv. Chim. Acta 5, 267 (1922).

The compound [sic] of the formula (II), (IIa), (IIb), (IIc), (IId) and (IIe) and precursors thereof used in the processes described above are novel in some cases and correspond in particular tot he formula (II')

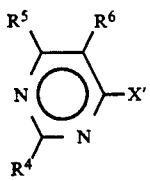

(II')

in which

X' is CO-halogen, $CO_2R^{10}$, $COO^-Me^+$, in which $Me^+$ is the equivalent of an alkali metal or alkaline earth metal, or $CO_2CH_2C_6H_5$ or CN and $R^6$, $R^5$, $R^4$ and $R^{10}$ have the meanings already mentioned.

Specific heterocyclic precursors for the preparation of the compounds of the formula I are described in the following publications:

Reiner, Eugster; Helv. Chem. Acta 50, 128 (1967); (2-methylpyrimidine-4-carboxylic acid).

Holy, Collect. Czech. Chem. Commun. 40, 738 (1975); (methyl 2,6-dimethoxypyrimidine-4-carboxylate).

Budesinsky, Collect. Czech. Chem. Commun. 37, 1721 (1972);
(2-methoxy-5-bromo-4-pyrimidinecarboxylic acid and 2-methoxy-5-chloro-4-pyrimidinecarboxylic acid).

Cherkasov, Chem. Heterocycl. Compd. (Engl. Transl.) 8, 509 (1972);
(6-methoxy-4-pyrimidinecarboxylic acid, 6-chloro-4-pyrimidinecarboxylic acid).

Sakasai, Heterocycles 13, 235 (1979); Brown, Aust. J. Chem. 27, 2251 (1974);
(methyl 2,6-dimethylpyrimidine-4-carboxylate, methyl 6-methylpyrimidine-4-carboxylate, methyl 2-methylpyrimidine-4-carboxylate).

Budesinsky, Collect. Czech. Chem. Commun. 27, 2250 (1962);
(ethyl 6-chloro-5-fluoro-2-methylpyrimidine-4-carboxylate).

Schwan, J. Heterocycl. Chem. 2,202 (1965); (methyl 5-cyano-2-methylpyrimidine-4-carboxylate).

Budesinsky, Collect. Czech. Chem. Commun. 26, 2871 (1961);
(methyl 2-chloro-6-methylpyrimidine-4-carboxylate, 2-chloro-6-methylpyrimidine-4-carboxylic acid, 2,6-dimethylpyrimidine-4-carboxylic acid).

Daves, J. Heterocycl. Chem. 1, 130 (1964); (methyl 6-chloropyrimidine-4-carboxylate).

Klötzer, Monatsh. Chem. 87, 526 (1956); Beak, J. Am. Chem. Soc. 98, 3601 (1976);
(2,6-dimethoxypyrimidine-4-carboxylic acid,2,6-dimethylpyrimidine-4-carboxylic acid).

Yamanaka, hem. Pharm. Bull. 6, 638 (1958); (ethyl 2,6-dimethylpyrimidine-4-carboxylate).

Budesinsky, Collect. Czech. Chem. Commun. 14, 224 (1949); (ethyl 5-bromo-2-methylpyrimidine-4-carboxylate, ethyl 5-chloro-2-methylpyrimidine-4-carboxylate, 5-bromo-2-methylpyrimidine-4-carboxylic acid, 5-chloro-2-methylpyrimidine-4-carboxylic acid).

Angerstein, Chem. Ber. 34, 3958 (1901); (6-methylpyrimidine-4-carboxylic acid).

Bhatt, J. Heterocycl. Chem. 18, 771 (1981); (methyl 5-iodo-2,6-dimethoxypyrimidine-4-carboxylate).

The invention therefore also relates to carboxylic acids which can be used as intermediates, of the formula II' (X'=COOH), their salts, their esters, benzyl esters and carboxylic acid halides, with the exception of the known compounds (see Table; known compounds are characterized by indication of the CAS registry number, <Reg. No.>):

TABLE 1

| $R^6$ | $R^5$ | $R^4$ | CAS <Reg. No.> or m.p. [°C.] | Ester CAS <Reg. No.> or m.p. [°C.] |
|---|---|---|---|---|
| H | $OCH_3$ | $OCH_3$ | <59864-30-1> | methyl ester <55870-45-0> |
| F | $OCH_3$ | $OCH_3$ | | |
| Cl | $OCH_3$ | $OCH_3$ | 177-119 | methyl ester 98-100 |
| Br | $OCH_3$ | $OCH_3$ | | |
| I | $OCH_3$ | $OCH_3$ | 125-126 | methyl ester <79115-66-5> |
| CN | $OCH_3$ | $OCH_3$ | | |
| $NO_2$ | $OCH_3$ | $OCH_3$ | | |
| $CO_2CH_3$ | $OCH_3$ | $OCH_3$ | | |
| $CO_2C_2H_5$ | $OCH_3$ | $OCH_3$ | | |
| H | $OCH_3$ | $CH_3$ | 184-188 | methyl ester 90-93 |
| F | $OCH_3$ | $CH_3$ | | |
| CL | $OCH_3$ | $CH_3$ | | |
| Br | $OCH_3$ | $CH_3$ | | |
| I | $OCH_3$ | $CH_3$ | | |
| CN | $OCH_3$ | $CH_3$ | | |
| $NO_2$ | $OCH_3$ | $CH_3$ | | |
| $CO_2CH_3$ | $OCH_3$ | $CH_3$ | | |
| $CO_2C_2H_5$ | $OCH_3$ | $CH_3$ | | |
| H | $CH_3$ | $OCH_3$ | 161-163 | methyl ester 101-103 |
| F | $CH_3$ | $OCH_3$ | | |
| Cl | $CH_3$ | $OCH_3$ | | |
| Br | $CH_3$ | $OCH_3$ | | |
| I | $CH_3$ | $OCH_3$ | | |
| CN | $CH_3$ | $OCH_3$ | | |
| $NO_2$ | $CH_3$ | $OCH_3$ | | |

TABLE 1-continued

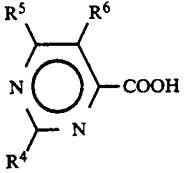

| R⁶ | R⁵ | R⁴ | CAS <Reg. No.> or m.p. [°C] | Ester CAS <Reg. No.> or m.p. [°C] |
|---|---|---|---|---|
| CO₂CH₃ | CH₃ | OCH₃ | | |
| CO₂C₂H₅ | CH₃ | OCH₃ | | |
| H | CH₃ | CH₃ | <54198-74-2> | Ethyl ester <103796-11-8> |
|   |   |   |   | Methyl ester <54198-73-1> |
| F | CH₃ | CH₃ | | |
| Cl | CH₃ | CH₃ | | |
| Br | CH₃ | CH₃ | | |
| I | CH₃ | CH₃ | | |
| CN | CH₃ | CH₃ | | |
| NO₂ | CH₃ | CH₃ | | |
| CO₂CH₃ | CH₃ | CH₃ | | |
| CO₂C₂H₅ | CH₃ | CH₃ | | |
| H | Cl | CH₃ | from 132 | |
| F | Cl | CH₃ | | |
| Cl | Cl | CH₃ | | Methyl ester <712-22-1> |
| Br | Cl | CH₃ | | |
| I | Cl | CH₃ | | |
| CN | Cl | CH₃ | | |
| NO₂ | Cl | CH₃ | | |
| CO₂CH₃ | Cl | CH₃ | | |
| CO₂C₂H₅ | Cl | CH₃ | | |
| H | CH₃ | Cl | <89581-58-8> | Methyl ester <89793-11-3> |
| F | CH₃ | Cl | | |
| Cl | CH₃ | Cl | | |
| Br | CH₃ | Cl | | |
| I | CH₃ | Cl | | |
| CN | CH₃ | Cl | | |
| NO₂ | CH₃ | Cl | | |
| CO₂CH₃ | CH₃ | Cl | | |
| CO₂C₂H₅ | CH₃ | Cl | | |
| H | Cl | OCH₃ | | |
| F | Cl | OCH₃ | | |
| Cl | Cl | OCH₃ | | |
| Br | Cl | OCH₃ | | |
| I | Cl | OCH₃ | | |
| CN | Cl | OCH₃ | | |
| NO₂ | Cl | OCH₃ | | |
| CO₂CH₃ | Cl | OCH₃ | | |
| CO₂C₂H₅ | Cl | OCH₃ | | |
| H | OCH₃ | Cl | <89581-58-8> | Methyl ester <89793-11-3> |
| F | OCH₃ | Cl | | |
| Cl | OCH₃ | Cl | | |
| Br | OCH₃ | Cl | | |
| I | OCH₃ | Cl | | |
| CN | OCH₃ | Cl | | |
| NO₂ | OCH₃ | Cl | | |
| CO₂OCH₃ | OCH₃ | Cl | | |
| CO₂C₂H₅ | OCH₃ | Cl | | |

If a=O, the sulfonamides of the formula III used in processes a₁) and a₂) as intermediates are obtained from the corresponding anilines by diazotization and replacement of the diazo group by sulfur dioxide in the presence of a catalyst such as copper(I) chloride in hydrochloric acid or acetic acid and reaction of the resultant sulfonyl chloride with ammonia, cf. Meerwein, Chem. Ber. 1957, 90, 841–852.

The intermediates of the formula III (where X=O and a=1 are obtained from the corresponding phenols by reaction with chlorosulfonyl isocyanate and subsequent hydrolysis, cf. Lohaus, Chem. Ber. 1972, 105, 2791–2799.

The compounds of the formula III where X=NR⁷ and a=1 are prepared from the corresponding anilines in a known manner by reaction with amidosulfonyl chloride in the presence of an auxiliary base such as triethylamine.

The sulfonamides of the formula III where X=CHR² and a=1 are obtained by customary methods from the corresponding benzyl halides by reaction with thiourea, then oxidation with chlorine and subsequent reaction with ammonia. The sulfonamides of the formula III where X=CHR² and a=1 are also obtained from the corresponding benzyl halides after conversion into the Grignard reagent by reaction with SO₂ and subsequent reaction of the resultant sulfinate salt with hydroxylamine-O-sulfonic acid in buffered aqueous acid, cf. S. L. Graham, Synthesis 1986, 1031, 1032.

Alternatively, in the case of the 2-pyridyl derivatives, sulfonamides of the general formula (III) in which, preferably, L=L5, X=CHR² and a=1 can be obtained by metalation of the corresponding 2-methylpyridine compounds of the general formula (IIIa)

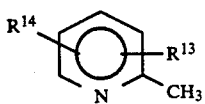

(IIIa)

in which $R^{13}$ and $R^{14}$ have the abovementioned meaning, with suitable bases such as, for example, butyllithium, subsequent reaction of the organometallic compound with $SO_2$ and reaction of the resultant sulfinate salt with hydroxylamine-O-sulfonic acid. The metalation and the reaction with $SO_2$ in this case preferably take place in ethereal solvents and hydrocarbons in the temperature range from $-120°$ C. to $+10°$ C., while the resultant sulfinate salts are preferably reacted in buffered aqueous solution.

Likewise, sulfonamides of the general formula (III) in which, preferably, L=L5, X=$CHR^2$ and a=1 can be obtained by substitution reactions of pyridine compounds of the general formula (IIIb)

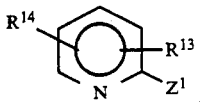

(IIIb)

in which
$Z^1$ is a leaving group, such as, for example, halogen, methylsulfonyl or tetraalkylammonium, with substituted alkylsulfonamides of the general formula (X)

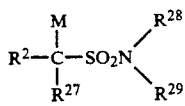

(X)

in which
M is hydrogen or a metal atom, $R^{27}$ is hydrogen or $CO_2(C_1-C_3)$alkyl, $R^{28}$ is tert.-butyl or trialkylsilyl and $R^{29}$ is hydrogen, a metal atom or trialkylsilyl, and subsequent alkaline or, preferably, acid hydrolysis.

Sulfonamides of the general formula (III) in which, preferably, L=5, X=$CHR^2$ and a=1 can likewise be prepared by cyclization of open-chain intermediates of the general formula (XI) and (XII)

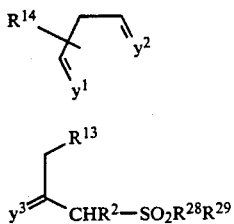

(XI)

(XII)

in which
$y^1$ is oxygen, (Oalkyl)$_2$ or NH, $y^2$ is oxygen or (Oalkyl)$_2$, $y^3$ is oxygen or NH and $R^2$, $R^{13}$, $R^{14}$, $R^{28}$ and $R^{29}$ have the abovementioned meaning.

Compounds of the formula III in which $R^1$ [lacuna] said meaning, preferably, H, and X=$CH_2$, a=1 and L=L5 are novel and likewise a subject of the invention.

The sulfonyl isocyanates of the formula (VI) are prepared by standard processes known to the person skilled in the art, see "Newer Methods of Preparative Organic Chemistry", Volume VI, 223–241, Academic Press, New York & London, Lohaus, Chem. Ber. 105 1972), 2791.

The compounds of the formula I according to the invention have an excellent herbicidal activity against a wide spectrum of economically important mono- and dicotyledon weeds. Even poorly controllable perennial weeds, which sprout from rhizomes, root stocks or other perennial organs, are easily controlled by the active compounds. It is unimportant here whether the substances are applied in the presowing, pre-emergence or post-emergence processes. In particular, by way of example, some representatives of the mono- and dicotyledon weed flora may be mentioned which can be controlled by the compounds according to the invention without a restriction to certain species resulting owing to their mention.

On the side of monocotyledon weed species, for example, Avena, Lolium, Alopecurus, Phalaris, Echinochloa, Digitaria, Setaria etc. and also Cyperus species from the annual group and on the side of the perennial species Agropyron, Cynondon, Imperata and Sorghum etc. and also perennial Cyperus species are well controlled.

In the case of dicotyledon weed species, the spectrum of action extends to species such as, for example, Galium, Viola, Veronica, Lamium, Stellaria, Amarathus, Sinapis, Ipomoea, Matricaria, Abutilon, Sida etc. on the annual side and Convolvulus, Cirsium, Rumex, Artemisia etc. in the perennials.

Weeds occurring under the specific cultivation conditions in rice such as, for example, Sagittaria, Alisma, Eleocharis, Scirpus, Cyperus etc. are likewise excellently controlled by the active compounds according to the invention.

If the compounds according to the invention are applied to the soil surface before the seeds, either the emergence of the weed seedlings is completely prevented or the weeds grow to the seed leaf stage, but then cease their growth and finally die off completely after three to four weeks have elapsed. When the active compounds are applied to the green parts of plants in the post-emergence process, a drastic stop in growth likewise occurs very rapidly after the treatment, and the weed plants remain at the stage of growth existing at the time of application or die off more or less rapidly after a certain time, so that in this way weed competition which is harmful to the cultivated plants can be eliminated very early and in a lasting manner by the use of the novel compounds according to the invention.

Although the compounds according to the invention exhibit an excellent herbicidal activity to mono- and dicotyledon weeds, cultivated plants of economically important cultures such as, for example, wheat, barley, rye, rice, corn, sugar beet, cotton and soya are only damaged insignificantly or not at all. For these reasons, the present compounds are highly suitable for the selective control of undesired plant growth in productive agricultural plantations.

Moreover, the compounds according to the invention show growth-regulatory properties in cultivated plants. They intervene in the plant's own metabolism in a regulating manner and can therefore be employed to facilitate harvesting such as, for example, by inducing desiccation, abscission and compression of growth. In addition, they are also suitable for the general control and inhibition of undesired vegetative growth, without at the same time killing the plants. Inhibition of the vegetative growth plays a large role in many mono- and dicotyledon cultures, as storage can be reduced or completely prevented by means of this.

The compounds of the formula (I) or their combination with one or more of said herbicides or herbicide groups can be variously formulated, according to which biological and/or physicochemical parameters have been presented. Examples of suitable formulation possibilities are: wettable powders (WP), emulsifiable concentrates (EC), aqueous solutions (SL), emulsions, sprayable solutions, dispersions having an oil or water base, suspoemulsions (SC), dusting agents (DP), seed dressings, granules for the soil or for broadcasting, water dispersible granules (WG), ULV formulations, microcapsules or waxes.

These individual formulation types are known in principle and are described, for example, in: Winnacker-Küchler, "Chemische Technoloie" (Chemical Technology), Volume 7, C. Hauser Verlag Munich, 4th Ed. 1986; van Valkenburg, "Pesticides Formulations", Marcel Dekker N.Y., 2nd Ed. 1972-73; K. Martens, "Spray Drying Handbook", 3rd Ed. 1979, G. Goodwin Ltd. London.

The formulation auxiliaries required such as inert materials, surfactants, solvents and other additives are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y., Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Suchönfeldt, "Grenzflächenaktive Äthylenoxidaddukte" (Surface-active ethylene oxide adducts), Wiss. Verlagsgesell., Stuttgart 1976; Winnacker-Küchler, "Chemische Technologie" (Chemical Technology), Volume 7, C. Hauser Verlag Munich, 4th Ed. 1986.

On the basis of these formulations, combinations with other pesticidally active substances, fertilizers and/or growth regulators can also be prepared, for example in the form of a finished formulation or as a tank mix.

Wettable powders are preparations which can be uniformly dispersed in water and, besides the active compound, apart from a diluent or inert substance additionally contain wetting agents, for example polyoxyethylated alkylphenols, polyoxyethylated fatty alcohols or fatty amines alkane- or alkylbenzenesulfonates and dispersing agents, for example sodium ligninsulfonate, sodium 2,2'-dinaphthylmethane-6,6'-disulfonate, sodium dibutylnaphthalenesulfonate or, alternatively, sodium oleylmethyltaurate.

Emulsifiable concentrates are prepared by dissolving the active compound in an organic solvent, for example butanol, cyclohexanone, dimethylformamide, xylene or, alternatively, higher-boiling aromatics or hydrocarbons with the addition of one or more emulsifiers. Examples of emulsifiers which can be used are: alkylarylsulfonic acid calcium slats such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, pyrophillite or diatomaceous earth.

Granules can either be prepared by spraying the active compound onto adsorptive granulated inert material or by applying active compound concentrates by means of adhesives, for example polyvinyl alcohol, sodium polyacrylate or, alternatively, mineral oils, to the surface of support substances such as sand or kaolinites or of granulated inert material. Suitable active compounds can also be granulated in the customary manner for the preparation of fertilizer granules—if desired mixed with fertilizers.

The agrochemical preparations as a rule contain 0.1 to 99% by weight, in particular 0.1 to 95% by weight, of active compound of the formula (I), 1 to 99.9% by weight, in particular 5 to 99.8% by weight, of a solid or liquid additive and 0 to 25% by weight of a surfactant.

In wettable powders the active compound concentration is, for example, about 10 to 90% by weight, the remainder to 100% by weight consists of customary formulation components. In the case of emulsifiable concentrates, the active compound concentration can be about 1 to 85% by weight, preferably 5 to 80% by weight. Dust-like formulations contain about 1 to 25% by weight, mostly 5 to 20% by weight of active compound, sprayable solutions about 0.2 to 25% by weight, preferably 2 to 20% by weight of active compound. In the case of water-dispersible granules, the active compound content partially depends on whether the active compound is liquid or solid. In general, the content in the water-dispersible granules is between 10 and 90% by weight.

In addition, said active compound formulations optionally contain the adhesives, wetting agents, dispersants, emulsifiers, penetrants, solvents, fillers or support substances customary in each case.

For application, the formulations present in commercial form are optionally diluted in a customary manner, for example by means of water in the case of wettable powders, emulsifiable concentrates, dispersions and water-dispersible granules. Dust-like preparations, granules for the soil or for broadcasting and sprayable solutions are customarily not diluted further with other inert substances before application.

The application rate of the compounds of the formula (I) required varies with the external conditions such as temperature, humidity, the nature of the herbicide used and the like. It can vary within wide limits, for example between 0.005 and 10.0 kg/ha or more of active substance, but it is preferably between 0.01 and 5 kg/ha.

Mixtures or mixed formulations with other active compounds, such as, for example, insecticides, acaricides, herbicides, safeners, fertilizers, growth regulators or fungicides may also be possible.

The compounds of the formula (I) according to the invention are additionally distinguished by an excellent fungicidal action. Causative organisms of fungal disease which have already penetrated into the plant tissue can be successfully controlled in a curative manner. This is particularly important and advantageous in those fungal diseases which, after infection has occurred, can no longer be controlled effectively with the otherwise customary fungicides. The spectrum of action of the compounds claimed includes various economically important phytopathogenic fungi, such as, for example, Pyricularia oryzae, Leptospaeria nodorum, Pyrenophora teres, various rust fungi and Botrytis cinerea; the excellent action against natural mildew fungi is particularly to be emphasized.

The compounds according to the invention are in addition also suitable for use in industrial fields, for example as wood preservatives, as preservatives in paints, in cooling lubricants for metal processing or as preservatives in drilling and cutting oils.

The invention also relates to fungicidal agents which contain the compounds of the formula I in addition to suitable formulation auxiliaries. The fungicidal agents according to the invention in general contain the active compounds of the formula I in amounts of 1 to 95% by weight.

They can be variously formulated, depending on how it is prespecified by the biological and/or physicochemical parameters. Suitable formulation possibilities are in principle all those which have already been mentioned above for herbicidal agents.

The application rate required varies with the external conditions such as temperature, humidity and the like. It can vary within wide limits, for example between 0.005 and 10.0 kg/ha or more of active substance, but it is preferably between 0.01 and 5 kg/ha. [sic]

The active compounds according to the invention in their commercial formulations can be applied either alone or in combination with other fungicides known from the literature.

Examples of fungicides known from the literature which may be mentioned and which, according to the invention, can be combined with the compounds of the formula I are the following products:

imazalil, prochloraz, fenapanil, SSF 105, triflumizol, PP 969, flutriafol, BAY-MEB 6401, propiconazole, etaconazole, diclobutrazol, bitertanol, triadimefon, triadimenol, fluotrimazole, tridemorph, dodemorph, fenpropimorph, falimorph, S-32165, chlobenzthiazone, parinol, buthiobate, fenpropidin, triforine, fenarimol, nuarimol, triarimol, ethirimol, dimethirimol, bupirimate, rabenzazole, tricyclazole, fluobenzimine, pyroxyfur, NK-483, PP-389, pyroquilon, hymexazole, fenitropan, UHF-8227, cymoxanil, dichlofunanid [sic], captafol, captan, folpet, tolyfluanid, chlorothalonil, etridiazsole, iprodione, procymidone, vinclozole [sic], metomeclan, myclozolin, dichlozolinate, fluorimide, drazaxolan, quinomethionate, nitrothal-isopropyl, dithianon, dinocap, binapacyl, fentin acetate, fentin hydroxide, carboxin, oxycarboxin, pyracarolid [sic], methfuroxam, fenfura [sic], furmecyclos, benodanil, mebenil, mepronil, flutalanil, fuberidazole, thiabendazole, carbendazim, benomyl, thiofante [sic], thiofanate-methyl [sic], CDG-95340 F, IKF-1216, mancozeb, maneb, zineb, nabam, thiram, probineb, prothiocarb, propamocarb, dodine, quazatine, dicloran, quintozene, chloroneb, techazene, biphenyl, anilazine, 2-phenylphenol, copper compounds such as Cu oxychloride, oxine Cu, Cu oxides, sulfur, fosethylaluminum, sodium dodecylbenzenesulfonate, sodium dodecyl sulfate, sodium C13/C15 alcohol ether sulfonate, sodium cetostearylphosphate ester, dioctyl sodium sulfosuccinate, sodium isopropylnaphthalenesulfonate, sodium methylenebisnaphthalenesulfonate, cetyltrimethylammonium chloride, Salts of long-chain primary, secondary or tertiary amines, alkylpropyleneamines, laurylpyridinium bromide, ethoxylated quaternized fatty amines, alkyldimethylbenzylammonium chloride and 1-hydroxyethyl-2-alkylimidazoline.

The abovementioned combination components are known active compounds, many of which are described in CH [sic].R. Worthing, U. [sic] S. B. Walker, "The Pesticide Manual", 7th Edition (1983) and 8th Edition (1987), British Crop Protection Council.

The active compounds according to the invention, in particular those of the examples mentioned, can in addition be present in their commercial formulations and in the formulations prepared from these and in the application forms prepared from these formulations mixed with other active compounds, such as insecticides, attractants, sterilants, acaricides, nematicides, fungicides, growth-regulating substances or herbicides. The insecticides include, for example, phosphoric acid esters, carbamates, carboxylic acid esters, formamidines, tin compounds, substances produced by microorganisms and the like. Preferred mixture components are:

1. from the phosphoric acid ester group azinphos ethyl, azinphos methyl, 1-(e-chlorophenyl)-4-(O-ethyl, S-propyl)phosphoryl-oxypyrazole sic] (TIA-230), chloropyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, pirimiphosethyl, pirimiphos-ethyl, profenoos, prothiofos, sulprofos, triazophos or trichlorophene [sic].

2. from the carbamate group aldicarb, bendiocarb, BPMC (2-(1-methylpropyl)-phenylmethyl carbamate), butocarboxim, butoxycarboxim, carbaryl, carbofuran, carbosulfan, cloethocarb, isoprocarb, methomyl, oxamyl, primicarb [sic], promecarb, propoxur or thiodicarb.

3. from the carboxylic acid ester group allethrin, alphamethrin, bioallethrin, bioresmethrin, cycloprothrin, cyfluthrin, cyhalothrin, cypermethrin, deltamethrin, alpha-cyano-3-phenyl-2-methyl-benzyl 2,2-dimethyl-3-(2-chloro-2-trifluoromethylvinyl)-cyclopropanecarboxyl (FMC 54800), fenpropathrin, fenfluthrin, fenvalerate, flucythrinate, flumethrin, fluvalinate, permethrin, resmethrin or tralomethrin.

4. rom the formamidine group Amitraz or chlorodimeform 5 from the tin compound group azocyclotin, cyhexatin and fenbutatin oxide 6. Miscellaneous abamektin, Bacillus thuringiensis, bensultap, binapacyl, bromopropylate, buprofgecin, camphechlor, cartap, chlorenzialate [sic], chlorofluazuron, 2-(4-chlorophenyl)-4,5-diphenylthiophene (UBI-T 930), chlofentezine, 2-naphthylmethyl cyclopropanecarboxylate (Ro 12-0470), cyromacin, DDT, dicofol, N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,2-thioazol- 2-ylidene)-2,4-xylidine, dinobuton, dinocap, endosulfan, fenoxycarb, fenothiocarb, flubenzimine, flufenoxuron, gamma-HCH, hexythiazox, hydramethylnon (AC 217 300), ivermectin, 2-nitromethyl-4,5-dihydro-6H-thiazine (SD 52618), 2-nitromethyl-3,4-dihydrothiazole (SD 35651), 2-nitromethylene-1,3-thiazinan-3-yl-carbamaldehyde (WL 108 477), propargite, teflubenzuron, tetradifon, tetrasul, thicyclam, triflumaron, core polyhdrosis and granulosis viruses.

The active compound content of the application forms prepared from the commercial formulations can vary within wide ranges, and the active compound concentrations of the application forms can be from 0.0001 up to 100% by weight of active compound, preferably between 0.001 and 1% by weight. Application is carried out in one [lacuna] customary ways suited to the application forms.

A. Formulation examples a) A dusting agent is obtained by mixing 10 parts by weight of a compound of the formula (I) and 90 parts by weight of talc as the inert substance and comminuting in a hammer mill.

b) A wettable powder which is easily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurate as the wetting agent and dispersant and grinding the mixture in a pinned disk mill.

c) A dispersion concentrate which is easily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 pats by weight of paraffin mineral oil (boiling range, for example, about 255 to above 277° C.) and grinding the mixture in a friction ball mill to a fineness of less than 5 microns.

d) An emulsifiable concentrate is obtained from 15 parts by weight of a compound of the formula (I), 75 parts by weight of cyclohexanone as the solvent and 10 parts by weight of oxyethylated nonylphenol as the emulsifier.

e) Granules dispersible in water are obtained in by mixing

| |
|---|
| 75 parts by weight of a compound of the formula I, |
| 10 parts by weight of calcium ligninsulfonate, |
| 5 parts by weight of sodium lauryl sulfate, |
| 3 parts by weight of polyvinyl alcohol and |
| 7 parts by weight of kaolin | grinding the mixture in a pinned disk mill ad granulating the powder in a fluidized bed by spraying in water as the granulating liquid.

f) Granules dispersible in water are also obtained b homogenizing and precomminuting

| | |
|---|---|
| 25 parts by weight | of a compound of the formula (I), |
| 5 parts by weight | of sodium 2,2'-dinaphthylmethane-6,6'-disulfonate, |
| 2 parts by weight | of sodium oleoylmethyltaurate, |
| 1 parts by weight | of polyvinyl alcohol, |
| 17 parts by weight | of calcium carbonate and |
| 50 parts by weight | of water | ps in a colloid mill, then grinding the mixture in a bead mill and comminuting the suspension thus obtained in a spray tower by means of a single-component nozzle and drying the product.

g) Granules can be prepared from 2 to 15 parts b weight of active compound and an inert granulate support material such as attapulgite, pumice granules and/or quartz sand. Expediently, a suspension of the wettable powder from Example Ab) having a solid content of 30% is used and this is sprayed onto the surface of attapulgite granules, dried and mixed intimately. The weight content of the wettable powder here is about 5% and that of the inert support material is about 95% of the finished granules.

B. Chemical examples

EXAMPLE 1

Methyl 5-chloro-2,6-dimethoxypyrimidine-4-carboxylate 4 g of methyl 2,5,6-trichloropyrimidine-4-carboxylate dissolved in 100 ml of abs. methanol are added dropwise to a solution of 7.4 g of sodium in 100 ml of abs. methanol, whereupon the reaction temperature rises. Stirring is continued for a further hour at room temperature, the solvent is distilled off in vacuo and the residue is taken up in water/dichloromethane. The aqueous phase is neutralized using 2N hydrochloric acid and extracted twice using dichloromethane. The combined organic phases are dried over sodium sulfate and filtered through a silica gel bed. After distilling off the solvent, 32.0 g of methyl 5-chloro-2,6-dimethoxypyrimidine-4-carboxylate of melting point 98°–100° C. are obtained.

EXAMPLE 2

5-Chloro-2,6-dimethoxypyrimidine-4-carboxylic acid 29.5 g of methyl 5-chloro-2,6-dimethoxypyrimidine-4-carboxylate solid are added to a stirred solution of 5.4 g of sodium hydroxide in 100 ml of methanol and 5 ml of water. Stirring is continued at room temperature until completion of the hydrolysis (3H), methanol is distilled off and the residue is taken up in water. The aqueous phase is first extracted once using ethyl acetate, then acidified to pH 2-3 with conc. hydrochloric acid and extracted five times using dichloromethane. The combined dichloromethane extracts are dried over sodium sulfate, the solvent is distilled off and the residue is dried in vacuo at 50° c. 23.0 g of 5-chloro-2,5-dimethoxypyrimidine-4-carboxylic acid of melting point 117°–119° C. (dec.) are obtained in this way.

EXAMPLE 3

2,6-Dimethoxy-5-iodopyrimidine-4-carboxylic acid 18.0 g of methyl, 2,6-dimethoxy-5-iodopyrimidine-4-carboxylate are introduced in portions into a stirred solution of 2.4 g of sodium hydroxide in 70 ml of methanol and 4 ml of water. Stirring is allowed to continue overnight at room temperature, the methanol is distilled off and the residue is taken up in water. The aqueous phase is extracted using ethyl acetate, acidified to pH 2-3 using conc. hydrochloric acid and extracted using dichloromethane. The combined dichloromethane extracts are dried over sodium sulfate and the solvent is distilled off in vacuo. 10.1 g of 2,6-dimethoxy-5-iodopyrimidine-4-carboxylic acid of melting point 125°–126° C. are obtained in this way.

EXAMPLE 4

Methyl 2-methoxy-6-methylpyrimidine-4-carboxylate 30.0 g of methyl 2-chloro-6-methylpyrimidine-4-carboxylate are added to a solution of 4.2 g of sodium in 100 ml of methanol. The mixture is heated under reflux for 2 h and concentrated under reduced pressure, and the residue is taken upon in dichloromethane/water. The organic phase is separated off and the aqueous solution is extracted a further five times using dichloromethane. The combined organic extracts are dried over sodium sulfate and the solvent is distilled off under reduced pressure. 25.5 g of methyl 2-methoxy-6-methylpyrimidine-4-carboxylate of melting point 101°–103° C. are obtained in this way.

EXAMPLE 5

2-methoxy-6-methylpyrimidine-4-carboxylic acid 15.5 g of methyl 2-methoxy-6-methylpyrimidine-4-carboxylate are added to a stirred solution of 3.6 g of sodium hydroxide in 100 ml of methanol and 10 ml of water. Stirring is continued at room temperature until the starting material disappears (TLC checking; 3 h). The methanol is distilled off under reduced pressure, the residue is taken up in water and the mixture is extracted once with ethyl acetate. The aqueous phase is acidified to pH 2 with conc. hydrochloric acid and then stirred for 1 h, and the product is filtered off with suction. 6.6 g of 2-methoxy-6-methylpyrimidine-4-carboxylic acid of melting point 161°–163° C. are obtained in this way. Concentration and extraction of the mother liquor using dichloromethane additionally gives 3.1 g of product of melting point 159°–161° C.

EXAMPLE 6

6-Chloro-2-methylpyrimidine-4-carbonyl chloride 126.1 g of 6-hydroxy-2-methylpyrimidine-4-carboxylic acid hydrate are heated to boiling in 500 ml of phosphorus oxychloride for 4 h until the evolution of gas is complete. The mixture is allowed to cool, 145 g of phosphorus(V) chloride are added and it is heated again under reflux until the evolution of gas is complete (5 h). The mixture is cooled to room temperature, the precipitated inorganic salts are filtered off with suction and excess phosphorus oxychloride is distilled off in a water jet vacuum. The residue is fractionated. 82.9 g of 6-chloro-2-methylpyrimidine-4-carbonyl chloride of boiling point 116°–119° C./38 mbar' are obtained in this way.

EXAMPLE

Methyl 6-methoxy-2-methylpyrimidine-4-carboxylate 78.9 g of 6-chloro-2-methylpyrimidine-4-carbonyl chloride is [sic] added dropwise with stirring to 750 ml of abs. methanol. Stirring is continued at room temperature for 14 h, the solvent is distilled off, the residue is taken up in dichloromethane and washed once with saturated aqueous sodium hydrogen carbonate solution and the organic phase is dried over sodium sulfate. After distilling off the dichloromethane, 65.5 g of methyl 6-methoxy-2-methylpyrimidine-4-carboxylate of melting point 90°–93° C. (recrystallized from diisopropyl ether) are obtained.

EXAMPLE 8

6-Methoxy-2-methylpyrimidine-4-carboxylic acid 62.6 g of methyl 6-methoxy-2-methylpyrimidine-4-carboxylate are added to a stirred solution of 14.4 g of sodium hydroxide in 100 ml of water and 350 ml of methanol and stirring is continued until hydrolysis is complete (TLC checking). 200 ml of methanol are added to the reaction mixture, and the sodium salt is filtered off with suction and then washed with methanol/diethyl ether (1:1) on the suction filter. The filter residue (59.3 g; melting point above 265° C.) dried in vacuo at 50° C. is introduced in portions into a solution of 24.5 g of acetyl chloride in 300 ml of methanol. The mixture is then stirred at room temperature for ½ h, the solid is filtered off with suction and the filter residue is then washed with abs. methanol. The filtrate is concentrated in vacuo on a rotary evaporator and the residue is dried at high vacuum. 25.1 g of 6-methoxy-2-methylpyrimidine-4-carboxylic acid of melting point 184°–188° C. (dec.) are obtained in this way.

EXAMPLE 9

6-Chloro-2-methylpyrimidine-4-carboxylic acid 16 g of 6-chloro-2-methylpyrimidine-4-carbonyl chloride are added dropwise at 10°–15° C. to 150 ml of water. The mixture is then stirred for ½ h, the solid is filtered off with suction, and the filter residue is then washed well with water and dried in vacuo at 50° C. 11.5 g of 6-chloro-2-methylpyrimidine-4-carboxylic acid of melting point 132° C. (dec.) are obtained in this way.

EXAMPLE 10

1-(2-Trifluoromethylphenyl)sulfuryldiamide 5.0 g of 2-trifluoromethylaniline are dissolved in 50 ml of dichloromethane and 3.5 of triethylamine are added. A solution of 4.0 g of sulfamoyl chloride in 40 ml of dichloromethane are added dropwise to this, whereupon the reaction temperature rises slightly. The mixture is then stirred at room temperature for 2 h, the solvent is distilled off under reduced pressure and the residue is stirred with 50 ml of 2N hydrochloric acid. The product is filtered off with suction, washed with water and dried in a high vacuum. 4.5 g of 1-(2-trifluoromethylphenyl)sulfuryldiamide of melting point 111°–113° C. are obtained in this way.

EXAMPLE 11

2,6-Dichlorophenyl sulfamate 2.6 ml of water are added dropwise at 30° C. to 40° C. to a solution of 24.4 g of 2,6-dichlorophenoxysulfonyl isocyanate in 200 ml of tetrachloromethane. The mixture is then stirred at room temperature until the evolution of carbon dioxide is complete and cooled to 0° C., the product is filtered off with suction and the residue is then washed with ice-cold tetrachloromethane. After drying in vacuo, 21.4 g of 2,6-dichlorophenyl sulfamate of melting point 108°–110° C. are obtained.

EXAMPLE 12

3-Methyl-2-picolylsulfonamide [sic]

36.5 g of 2,3-lutidine are slowly added dropwise at 0° C. to a solution of 0.51 mol of n-butyllithium as a 1.6N solution in hexane and 500 ml of abs. diethyl ether cooled to this temperature. The mixture is allowed to warm to 10° C. and is then stirred at this temperature for 3 h, and the lithium salt solution is added in portions at −60° C. to a solution of 150 ml of $SO_2$ and 200 ml of diethylether. The mixture is then stirred at this temperature for ½ h, allowed to warm to room temperature overnight and the solvent is distilled off under reduced pressure. The crude lithium sulfinate is taken up in 1.6 l of water, 66 g of sodium acetate and 50 g of hydroxylamine-O-sulfonic acid are added and the mixture is stirred at room temperature for 5 h. The aqueous solution is extracted repeatedly with dichloromethane at pH 7, the combined organic phases are dried over $Na_2SO_4$ and the solvent is distilled off in vacuo. The residue is recrystallized from diisopropyl ether/dichloromethane. 22.3 g of 3-methyl-2-picolylsulfonamide of melting point 155°–158° C. are obtained in this way.

EXAMPLE 13

2-Nitro-N-[(6-chloro-2-methylpyrimidin-4-yl)carbonyl]benzylsulfonamide 2.2 g of 2-nitrobenzylsulfonamide are added in portions at 0°–2° C. to a stirred solution of 2.3 g of dicyclohexylcarbodiimide, 120 mg of 4-dimethylaminopyridine and 1.9 g of 6-chloro-2-methylpyrimidine-4-carboxylic acid in 80 ml of abs. dichloromethane. Stirring is continued at 0° C. for ½ h and the mixture allowed to stand at room temperature for 2 days. The solid is filtered off with suction, the solvent is distilled off under reduced pressure, the residue is dissolved using acetone and the mixture is stirred with 100 ml of 10% strength aqueous sodium acetate solution for 2 h. The solid is filtered off, and the filtrate is extracted with diethyl ether and then acidified with conc. hydrochloric acid. The product is filtered off with suction and dried at 50° C./20 mbar. 1.55 g of 2-nitro-N-[(6-chloro-2-methylpyrimidin-4-dyl)carbonyl]benzylsulfonamide of melting point 190°–192° C. are obtained in this way.

EXAMPLE 14

2-Chloro-N-[(2-chloro-6-methylpyrimidin-4-yl)carbonyl]benzenesulfonamide 1.9 g of 2-chlorobenzenesulfonamide are added in portions at 0° C. to 2.1 g of 2-chloro-6-methylpyrimidine-4-carboxylic acid, 2.3 g of dicyclohexylcarbodiimide and 120 mg of 4-dimethylaminopyridine in 80 ml of abs. dichloromethane. The mixture is allowed to warm to room temperature during the course of ½ h and is then stirred for 4 days. After working up as described in Example 13, 1.2 g of 2-chloro-N-[(2-chloro-6-methylpyrimidin-4-yl)carbonyl]benzenesulfonamide of melting point 170°–171° C. are obtained.

EXAMPLE 15

2-Trifluoromethyl-N-[(6-methoxy-2-methylpyrimidin-4-yl)carbonyl]benzylsulfonamide 2.4 g of 2-trifluoromethylbenzylsulfonamide are added in portions at 0°–2° C. to a mixture of 2.3 g of dicyclohexylcarbodiimide, 120 mg of 4-dimethylaminopyridine and 2.0 g of 6-methoxy-2-methylpyrimidine-4-carboxylic acid in 80 ml of abs. dichloromethane. The mixture is then stirred at 0° C. for ½ h, allowed to warm to room temperature and then stirred for 14 h. The precipitated urea is filtered off with suction, the solvent is distilled off under reduced pressure, and the residue is dissolved in acetone and stirred with 100 ml of 1N aqueous sodium carbonate solution for ½ h. The solid is filtered off, the filtrate is extracted with diethyl ether and acidified with conc. hydrochloric acid, and the product is filtered off with suction and dried at 50° C./20 mbar [lacuna] 2-Trifluoromethyl-N-[(6-methoxy-2-methylpyrimidin-4-yl)carbonyl]benzylsulfonamide of melting point 120°–122° C. is obtained in this way.

EXAMPLE 16

1-(2-Trifluorometylphenyl)-3-[(2,6-dimethoxypyrimidin-4-yl)-carbonyl]sulfuryldiamide A solution of 2.4 g of 1-(2-trifluoromethylphenyl)sulfuryldiamide and 1.0 ml of triethylamine in 30 ml of acetone are added dropwise at 0° C. to 2° C. to a stirred mixture of 2.3 g of dicyclohexylcarbodiimide, 120 mg of 4-N,N-dimethylaminopyridine and 2.2 g of 2,6-dimethoxypyrimidine-4-carboxylic acid in 80 ml of dichloromethane. Stirring is continued at 0° C. for a further ½ h, then overnight at room temperature. The solid is filtered off with suction, the solvent is distilled off under reduced pressure and the residue is stirred with a solution of 50 ml of acetone and 100 ml of 1M sodium carbonate solution. Undissolved material is filtered off, the aqueous solution is extracted once with diethyl ether and then acidified with conc. hydrochloric acid to pH 2–3. The mixture is then stirred for ¼ h, and the product is filtered off with suction and dried at 50° C. in vacuo. 1.9 g of 1-(2-trifluoromethylphenyl)-3-[(2,6-dimethoxypyrimidin-4-yl)carbonyl]sulfuryldiamide of melting point 133°–135° C. are obtained in this way.

EXAMPLE 17

2-Nitro-N-[(2-methoxy-6-methylpyrimidin-4-yl)carbonyl]benzenesulfonamide 2.0 g of solid 2-nitrobenzenesulfonamide are added slid [sic] in portions at 0° C. to 2° C. to a stirred mixture of 2.3 g of dicyclohexylcarbodiimide, 120 mg of 4-N,N-dimethylaminopyridine and 2.0 g of 2-methoxy-6-methylpyrimidine-4-carboxylic acid in 80 ml of abs. dichloromethane. Stirring is continued at room temperature for ½ h and the mixture is then allowed to stand overnight. It is worked up as described in Example 16 and 1.55 g of 2-nitro-N-[(2-methoxy-6-methylpyrimidin-4-yl)carbonyl]benzenesulfonamide of melting point 212°–216° C. are obtained.

EXAMPLE 18

2-Trifluoromethyl-N-[(2-chloro-6-methylpyrimidin-4-yl)carbonyl]benzylsulfonamide 0.44 g of sodium hydride suspension (60% strength in mineral oil) is added to a stirred solution of 2.4 g of 2-trifluoromethylbenzylsulfonamide in 40 ml of dimethoxyethane and stirring is continued until the evolution of hydrogen is complete. A solution of 2-chloro-6-methylpyrimidine-4-carbonyl chloride (from 2.1 g of carboxylic acid, 20 ml of dioxane, [lacuna] drops of dimethylformamide and 2.1 g of thionyl chloride) in 20 ml of dimethoxyethane is rapidly added dropwise to this. The mixture is then stirred at room temperature for 3 h and worked up as described in Example 13. 1.4 g of 2-trifluoromethyl-N-[(2-chloro-6-methylpyrimidin-4-yl)carbonyl]benzylsulfonamide of melting point 198°–199° C. are obtained in this way.

The compounds of Tables 2 to 12 which follow can be prepared analogously to the procedures described in Examples 1 to 18. The definitions of the radicals of the formulae L 1-1 to L 5-29 precede Table 2. The meanings of the symbols in Tables 2 to 12 relate to the general formula preceding the respective table.

L 1 = 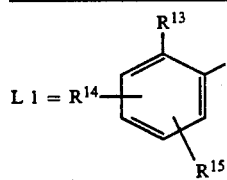

| | | | |
|---|---|---|---|
| L 1-1: $R^{13}$ = —$CO_2CH_3$; | $R^{14}, R^{15}$ = H | | |
| L 1-2: $R^{13}$ = —$CO_2CH_2CH_3$; | " | | |
| L 1-3: $R^{13}$ = —$CO_2CH(CH_3)_2$; | " | | |
| L 1-4: $R^{13}$ = —$CO_2CH_3$; | $R^{14}$ = 5-$OCF_2H$; | $R^{15}$ = H | |
| L 1-5: $R^{13}$ = —$CO_2CH_3$; | $R^{14}$ = 5-Cl,; | $R^{15}$ = H | |
| L 1-6: $R^{13}$ = —$CO_2CH_3$; | $R^{15}$ = 5-$OCH_3$; | $R^{15}$ = H | |
| L 1-7: $R^{13}$ = —$CO_2CON(CH_3)_2$; | $R^{14}, R^{15}$ = H | | |
| L 1-8: $R^{13}$ = —$CO_2CF_3$; | " | | |

L 1-9: $R^{13}$ = 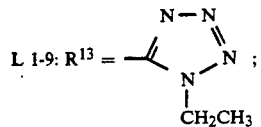 ;     "

L 1-10: $R^{13}$ = 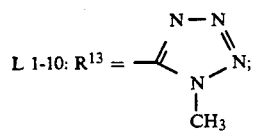 ;     "

L 1-11: $R^{13}$ = 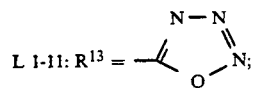 ;     "

L 1-12: $R^{13}$ = 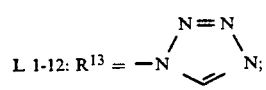 ;     "

L 1-13: $R^{13}$ = 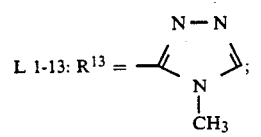 ;     $R^{14}$ = 6-Cl;     $R^{15}$ = H

L 1-14: $R^{13}$ = 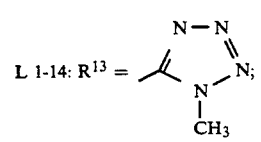 ;     $R^{14}$ = 5-$OCH_3$;     $R^{15}$ = H

| | | | |
|---|---|---|---|
| L 1-15: $R^{13}$ = —$OCH_3$; | $R^{14}, R^{15}$ = H | | |
| L 1-16: $R^{13}$ = —$OC_2H_5$; | " | | |
| L 1-17: $R^{13}$ = —$OCH(CH_3)_2$; | " | | |
| L 1-18: $R^{13}$ = —$OCH_2CH_2Cl$; | " | | |
| L 1-19: $R^{13}$ = —$OCH_2CH_2$—$OCH_3$; | " | | |
| L 1-20: $R^{13}$ = —$OCH_2CF_3$; | " | | |
| L 1-21: $R^{13}$ = —$OCF_2CF_3$; | " | | |
| L 1-22: $R^{13}$ = —$OSO_2CH_3$; | " | | |
| L 1-23: $R^{13}$ = —$OSO_2CH_2CH_3$; | " | | |
| L 1-24: $R^{13}$ = —Br; | " | | |
| L 1-25: $R^{13}$ = —F; | " | | |
| L 1-26: $R^{13}$ = —Cl; | " | | |
| L 1-27: $R^{13}$ = —$OCF_2CHF_2$; | " | | |
| L 1-28: $R^{13}$ = —$NO_2$; | " | | |
| L 1-29: $R^{13}$ = —$N(CH_3)_2$; | " | | |
| L 1-30: $R^{13}$ = —$N(CH_3)CH_2CH_3$; | " | | |
| L 1-31: $R^{13}$ = —$N(CH_2CH_3)_2$; | " | | |
| L 1-32: $R^{13}$ = —CN; | " | | |
| L 1-33: $R^{13}$ = —CO—$CH_3$; | " | | |
| L 1-34: $R^{13}$ = —F | $R^{14}$ = 6-F; | $R^{15}$ = H | |
| L 1-35: $R^{13}$ = —Cl; | $R^{14}$ = 6-Cl; | $R^{15}$ = H | |
| L 1-36: $R^{13}$ = —Br; | $R^{14}$ = 6-Br; | $R^{15}$ = H | |
| L 1-37: $R^{13}$ = —$NO_2$; | $R^{14}$ = 6-$CH_3$; | $R^{15}$ = H | |
| L 1-38: $R^{13}$ = —$CH_3$; | $R^{14}, R^{15}$ = H | | |
| L 1-39: $R^{13}$ = —$C_6H_5$; | " | | |

-continued

L 1-40: $R^{13}$ = —SO$_2$CH$_3$;  "
L 1-41: $R^{13}$ = —SO$_2$CH$_2$CH$_3$;  "
L 1-42: $R^{13}$ = —SO$_2$CH(CH$_3$)$_2$;  "
L 1-43: $R^{13}$ = —SO$_2$CH$_2$CH$_2$CH$_3$;  "
L 1-44: $R^{13}$ = —SO$_2$N(CH$_3$)$_2$;  "
L 1-45: $R^{13}$ = —CH$_2$Cl;  "
L 1-46: $R^{13}$ = —CH$_2$OCH$_3$;   $R^{14}, R^{15}$ = H
L 1-47: $R^{13}$ = —CH$_2$N(CH$_3$)$_2$;  "
L 1-48: $R^{13}$ = —CH$_2$SCH$_3$;  "
L 1-49: $R^{13}$ = —N$_3$;  "
L 1-50: $R^{13}$ = —SCH$_3$;  "
L 1-51: $R^{13}$ = —SCH$_2$CH$_3$;  "
L 1-52: $R^{13}$ = —OCF$_2$H;  "
L 1-53: $R^{13}$ = —OCF$_3$;  "
L 1-54: $R^{13}$ = —I;  "
L 1-55: $R^{13}$ = —NO$_2$;   $R^{14}$ = 6-F;   $R^{15}$ = H
L 1-56: $R^{13}$ = —NO$_2$;   $R^{14}$ = 6-Cl;   $R^{15}$ = H
L 1-57: $R^{13}$ = —NO$_2$;   $R^{14}$ = 6-I;   $R^{15}$ = H
L 1-58: $R^{13}$ = —Cl;   $R^{14}$ = 6-CH$_3$;   $R^{15}$ = H
L 1-59: $R^{13}$ = —CO$_2$CH$_3$;   $R^{14}$ = 6-NO$_2$;   $R^{15}$ = H
L 1-60: $R^{13}$ = —CO$_2$CH$_3$;   $R^{14}$ = 6-Cl;   $R^{15}$ = H
L 1-61: $R^{13}$ = —CO$_2$CH$_3$;   $R^{14}$ = 6-I;   $R^{15}$ = H
L 1-62: $R^{13}$ = —CO$_2$CH$_3$;   $R^{14}$ = 6-SO$_2$N(CH$_3$)$_2$;   $R^{15}$ = H
L 1-63: $R^{13}$ = —F;   $R^{14}$ = 6-I;   $R^{15}$ = H
L 1-64: $R^{13}$ = —F;   $R^{14}$ = 6-Cl;   $R^{15}$ = H
L 1-65: $R^{13}$ = —Cl;   $R^{14}$ = 6-I;   $R^{15}$ = H
L 1-66: $R^{13}$ = —SO$_2$N(CH$_3$)$_2$;   $R^{14}$ = 6-SO$_2$N(CH$_3$)$_2$;   $R^{15}$ = H
L 1-67: $R^{13}$ = —SO$_2$N(CH$_3$)$_2$;   $R^{14}$ = 6-Cl;   $R^{15}$ = H
L 1-68: $R^{13}$ = —SO$_2$N(CH$_3$)$_2$;   $R^{14}$ = 6-NO$_2$;   $R^{15}$ = H

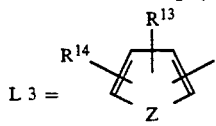

L 3 =

L 3-1: 3-Methoxycarbonyl-2-thienyl
L 3-2: 2-Methoxycarbonyl-3-thienyl
L 3-3: 2-Ethoxycarbonyl-3-thienyl
L 3-4: 4-Methoxycarbonyl-3-thienyl
L 3-5: 3-Chloro-2-thienyl

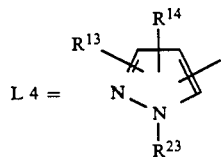

L 4 =

L 4-1: $R^{14}$ = H; $R^{13}$ = 4-CO$_2$CH$_3$; $R^{23}$ = CH$_3$; free valency on C-5
L 4-2: $R^{14}$ = H; $R^{13}$ = 4-CO$_2$CH$_2$CH$_3$; $R^{23}$ = —CH$_3$; free valency on C-5
L 4-3: $R^{14}$ = 3-Cl; $R^{13}$ = 4-CO$_2$CH$_3$; $R^{23}$ = —CH$_3$; free valency on C-5
L 4-4: $R^{14}$ = 3-SO$_2$N(CH$_3$)$_2$; $R^{13}$ = H; $R^{23}$ = —CH$_3$; free valency on C-4
L 4-5: $R^{14}$ = 3-CH$_3$; $R^{13}$ = 5-CO$_2$CH$_3$; $R^{23}$ = —CH$_3$; free valency on C-4

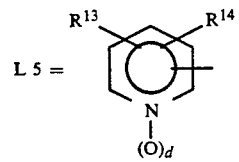

L 5 =

L 5-1: 3-Methoxycarbonyl-2-pyridyl
L 5-2: 3-Methylsulfonyl-2-pyridyl
L 5-3: 3-Ethoxycarbonyl-2-pyridyl
L 5-4: 3-Dimethylaminosulfonyl-2-pyridyl
L 5-5: 3-trifluoromethyl-2-pyridyl
L 5-6: 3-Methoxy-2-pyridyl
L 5-7: 3-Ethoxy-2-pyridyl
L 5-8: 3-Methyl-2-pyridyl
L 5-9: 3-Ethyl-2-pyridyl
L 5-10: 2-Dimethylaminosulfonyl-3-pyridyl
L 5-11: 2-Ethoxy-3-pyridyl
L 5-12: 2-chloro-3-pyridyl
L 5-13: 2-Methoxycarbonyl-3-pyridyl
L 5-14: 2-Ethoxycarbonyl-3-pyridyl
L 5-15: 2-Methoxy-3-pyridyl
L 5-16: 2-Methylsulfonyl-3-pyridyl
L 5-17: 3-chloro-2-pyridyl -continued L 5-18: 3-bromo-2-pyridyl
L 5-19: 3-iodo-2-pyridyl
L 5-20: 2-bromo-3-pyridyl
L 5-21: 2-fluoro-3-pyridyl
L 5-22: 2-iodo-3-pyridyl
L 5-23: 3-fluoro-2-pyridyl
L 5-24: 2-trifluoromethyl-3-pyridyl
L 5-25: 2-Pyridyl
L 5-26: 3-Thiomethyl-2-pyridyl
L 5-27: 3-Thioethyl-2-pyridyl
L 5-28: 3-Ethylsulfonyl-2-pyridyl
L 5-29: 3-Trifluormethoxy-2-pyridyl

TABLE 2

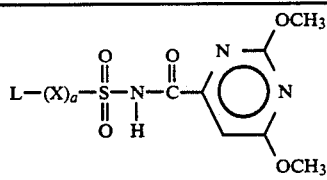

| Ex. No. | L | X | a | m.p. [°C.] |
|---|---|---|---|---|
| 1 | L1-1 | — | 0 | 124–126 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 149–152 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | 170–174 |
| 16 | L1-16 | — | 0 | 163–174 |
| 17 | L1-17 | — | 0 | |
| 18 | L1-18 | — | 0 | |
| 29 | L1-29 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | 172–180 |
| 26 | L1-26 | — | 0 | 200–202 |
| 27 | L1-27 | — | 0 | |
| 28 | L1-28 | — | 0 | 143–148 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | 175–182 |
| 36 | L1-36 | — | 0 | |
| 37 | L1-37 | — | 0 | 187–188 |
| 38 | L1-38 | — | 0 | 188–191 |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | 198–200 |
| 45 | L1-45 | — | 0 | 154–156 |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | 152–153 |
| 54 | L1-54 | — | 0 | 183–185 |
| 55 | L1-55 | — | 0 | |
| 56 | L1-56 | — | 0 | |

TABLE 2-continued

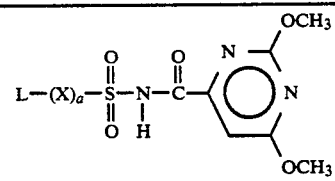

| Ex. No. | L | X | a | m.p. [°C.] |
|---|---|---|---|---|
| 57 | L1-57 | — | 0 | |
| 58 | L1-58 | — | 0 | 163–166 |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | CH$_2$ | 1 | 126–127 |
| 70 | L1-2 | CH$_2$ | 1 | |
| 71 | L1-3 | CH$_2$ | 1 | |
| 72 | L1-4 | CH$_2$ | 1 | |
| 73 | L1-5 | CH$_2$ | 1 | |
| 74 | L1-6 | CH$_2$ | 1 | |
| 75 | L1-7 | CH$_2$ | 1 | |
| 76 | L1-8 | CH$_2$ | 1 | 164–167 |
| 77 | L1-9 | CH$_2$ | 1 | |
| 78 | L1-10 | CH$_2$ | 1 | |
| 79 | L1-11 | CH$_2$ | 1 | |
| 80 | L1-12 | CH$_2$ | 1 | |
| 81 | L1-13 | CH$_2$ | 1 | |
| 82 | L1-14 | CH$_2$ | 1 | |
| 83 | L1-15 | CH$_2$ | 1 | |
| 84 | L1-16 | CH$_2$ | 1 | |
| 85 | L1-17 | CH$_2$ | 1 | |
| 86 | L1-18 | CH$_2$ | 1 | |
| 87 | L1-29 | CH$_2$ | 1 | |
| 88 | L1-20 | CH$_2$ | 1 | |
| 89 | L1-21 | CH$_2$ | 1 | |
| 90 | L1-22 | CH$_2$ | 1 | |
| 91 | L1-23 | CH$_2$ | 1 | |
| 92 | L1-24 | CH$_2$ | 1 | |
| 93 | L1-25 | CH$_2$ | 1 | 177–178 |
| 94 | L1-26 | CH$_2$ | 1 | 181–185 |
| 95 | L1-27 | CH$_2$ | 1 | |
| 96 | L1-28 | CH$_2$ | 1 | 172–177 |
| 97 | L1-29 | CH$_2$ | 1 | |
| 98 | L1-30 | CH$_2$ | 1 | |
| 99 | L1-31 | CH$_2$ | 1 | |
| 100 | L1-32 | CH$_2$ | 1 | |
| 101 | L1-33 | CH$_2$ | 1 | |
| 102 | L1-34 | CH$_2$ | 1 | |
| 103 | L1-35 | CH$_2$ | 1 | |
| 104 | L1-36 | CH$_2$ | 1 | |
| 105 | L1-37 | CH$_2$ | 1 | |
| 106 | L1-38 | CH$_2$ | 1 | |
| 107 | L1-39 | CH$_2$ | 1 | |
| 108 | L1-40 | CH$_2$ | 1 | |
| 109 | L1-41 | CH$_2$ | 1 | |
| 110 | L1-42 | CH$_2$ | 1 | |
| 111 | L1-43 | CH$_2$ | 1 | |
| 112 | L1-44 | CH$_2$ | 1 | |

TABLE 2-continued

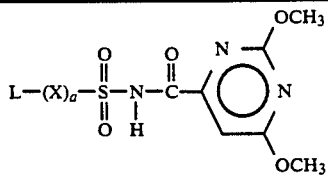

| Ex. No. | L | X | a | m.p. [°C.] |
|---|---|---|---|---|
| 113 | L1-45 | CH$_2$ | 1 | |
| 114 | L1-46 | CH$_2$ | 1 | |
| 115 | L1-47 | CH$_2$ | 1 | |
| 116 | L1-48 | CH$_2$ | 1 | |
| 117 | L1-49 | CH$_2$ | 1 | |
| 118 | L1-50 | CH$_2$ | 1 | |
| 129 | L1-51 | CH$_2$ | 1 | |
| 120 | L1-52 | CH$_2$ | 1 | |
| 121 | L1-53 | CH$_2$ | 1 | |
| 122 | L1-54 | CH$_2$ | 1 | 177 |
| 123 | L1-55 | CH$_2$ | 1 | |
| 124 | L1-56 | CH$_2$ | 1 | |
| 125 | L1-57 | CH$_2$ | 1 | |
| 126 | L1-58 | CH$_2$ | 1 | |
| 127 | L1-59 | CH$_2$ | 1 | 157–159 |
| 128 | L1-60 | CH$_2$ | 1 | |
| 129 | L1-61 | CH$_2$ | 1 | |
| 130 | L1-62 | CH$_2$ | 1 | |
| 131 | L1-63 | CH$_2$ | 1 | |
| 132 | L1-64 | CH$_2$ | 1 | |
| 133 | L1-65 | CH$_2$ | 1 | |
| 134 | L1-66 | CH$_2$ | 1 | |
| 135 | L1-67 | CH$_2$ | 1 | |
| 136 | L1-68 | CH$_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-29 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |

TABLE 2-continued

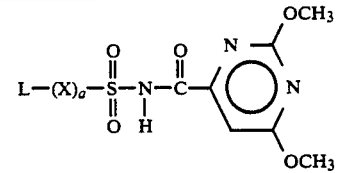

| Ex. No. | L | X | a | m.p. [°C.] |
|---|---|---|---|---|
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | 133–135 |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 229 | L1-15 | NH | 1 | |
| 220 | L1-16 | NH | 1 | 111–113 |
| 221 | L1-17 | NH | 1 | |
| 222 | L1-18 | NH | 1 | |
| 223 | L1-29 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |

TABLE 2-continued

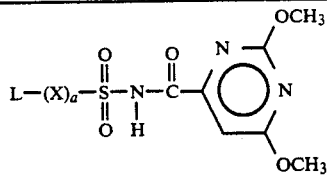

| Ex. No. | L | X | a | m.p. [°C.] |
|---|---|---|---|---|
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH$_2$ | 1 | |
| 299 | L4-2 | CH$_2$ | 1 | |
| 300 | L4-3 | CH$_2$ | 1 | |
| 301 | L4-4 | CH$_2$ | 1 | |
| 302 | L4-5 | CH$_2$ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-4 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 329 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-29 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH$_2$ | 1 | |
| 338 | L5-2 | CH$_2$ | 1 | |
| 339 | L5-3 | CH$_2$ | 1 | |
| 340 | L5-4 | CH$_2$ | 1 | |
| 341 | L5-5 | CH$_2$ | 1 | |
| 342 | L5-6 | CH$_2$ | 1 | |
| 343 | L5-7 | CH$_2$ | 1 | |
| 344 | L5-8 | CH$_2$ | 1 | |
| 345 | L5-9 | CH$_2$ | 1 | |
| 346 | L5-10 | CH$_2$ | 1 | |
| 347 | L5-11 | CH$_2$ | 1 | |
| 348 | L5-12 | CH$_2$ | 1 | |
| 349 | L5-13 | CH$_2$ | 1 | |
| 350 | L5-14 | CH$_2$ | 1 | |
| 351 | L5-15 | CH$_2$ | 1 | |
| 352 | L5-16 | CH$_2$ | 1 | |
| 353 | L5-17 | CH$_2$ | 1 | |
| 354 | L5-18 | CH$_2$ | 1 | |
| 355 | L5-29 | CH$_2$ | 1 | |
| 356 | L5-20 | CH$_2$ | 1 | |
| 357 | L5-21 | CH$_2$ | 1 | |
| 358 | L5-22 | CH$_2$ | 1 | |
| 359 | L5-23 | CH$_2$ | 1 | |
| 360 | L5-24 | CH$_2$ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-29 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 392 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 499 | L5-15 | NH | 1 | |
| 400 | L5-16 | NH | 1 | |

TABLE 2-continued

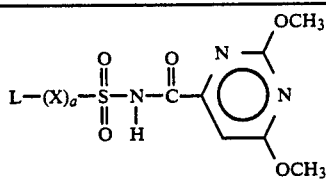

| Ex. No. | L | X | a | m.p. [°C.] |
|---|---|---|---|---|
| 401 | L5-17 | NH | 1 | |
| 402 | L5-18 | NH | 1 | |
| 403 | L5-29 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 3

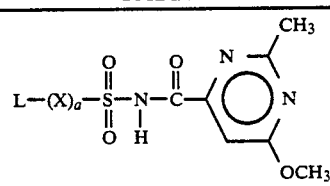

| Ex. No. | L | X | a | m.p. [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 159–162 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | 178–180 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |

TABLE 3-continued

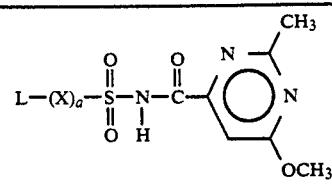

| Ex. No. | L | X | a | m.p. [°C.] |
|---|---|---|---|---|
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | CH$_2$ | 1 | |
| 70 | L1-2 | CH$_2$ | 1 | |
| 71 | L1-3 | CH$_2$ | 1 | |
| 72 | L1-4 | CH$_2$ | 1 | |
| 73 | L1-5 | CH$_2$ | 1 | |
| 74 | L1-6 | CH$_2$ | 1 | |
| 75 | L1-7 | CH$_2$ | 1 | |
| 76 | L1-8 | CH$_2$ | 1 | 120–122 |
| 77 | L1-9 | CH$_2$ | 1 | |
| 78 | L1-10 | CH$_2$ | 1 | |
| 79 | L1-11 | CH$_2$ | 1 | |
| 80 | L1-12 | CH$_2$ | 1 | |
| 81 | L1-13 | CH$_2$ | 1 | |
| 82 | L1-14 | CH$_2$ | 1 | |
| 83 | L1-15 | CH$_2$ | 1 | 142–144 |
| 84 | L1-16 | CH$_2$ | 1 | 117–119 |
| 85 | L1-17 | CH$_2$ | 1 | |
| 86 | L1-18 | CH$_2$ | 1 | |
| 87 | L1-19 | CH$_2$ | 1 | |
| 88 | L1-20 | CH$_2$ | 1 | |
| 89 | L1-21 | CH$_2$ | 1 | |
| 90 | L1-22 | CH$_2$ | 1 | |
| 91 | L1-23 | CH$_2$ | 1 | |
| 92 | L1-24 | CH$_2$ | 1 | |
| 93 | L1-25 | CH$_2$ | 1 | |
| 94 | L1-26 | CH$_2$ | 1 | |
| 95 | L1-27 | CH$_2$ | 1 | |
| 96 | L1-28 | CH$_2$ | 1 | 141–142 |
| 97 | L1-29 | CH$_2$ | 1 | |
| 98 | L1-30 | CH$_2$ | 1 | |
| 99 | L1-31 | CH$_2$ | 1 | |
| 100 | L1-32 | CH$_2$ | 1 | |
| 101 | L1-33 | CH$_2$ | 1 | |
| 102 | L1-34 | CH$_2$ | 1 | |
| 103 | L1-35 | CH$_2$ | 1 | |
| 104 | L1-36 | CH$_2$ | 1 | |
| 105 | L1-37 | CH$_2$ | 1 | |
| 106 | L1-38 | CH$_2$ | 1 | 165–166 |
| 107 | L1-39 | CH$_2$ | 1 | |
| 108 | L1-40 | CH$_2$ | 1 | |
| 109 | L1-41 | CH$_2$ | 1 | |
| 110 | L1-42 | CH$_2$ | 1 | |
| 111 | L1-43 | CH$_2$ | 1 | |
| 112 | L1-44 | CH$_2$ | 1 | |
| 113 | L1-45 | CH$_2$ | 1 | |
| 114 | L1-46 | CH$_2$ | 1 | |
| 115 | L1-47 | CH$_2$ | 1 | |
| 116 | L1-48 | CH$_2$ | 1 | |
| 117 | L1-49 | CH$_2$ | 1 | |
| 118 | L1-50 | CH$_2$ | 1 | |
| 119 | L1-51 | CH$_2$ | 1 | |
| 120 | L1-52 | CH$_2$ | 1 | |
| 121 | L1-53 | CH$_2$ | 1 | |

TABLE 3-continued

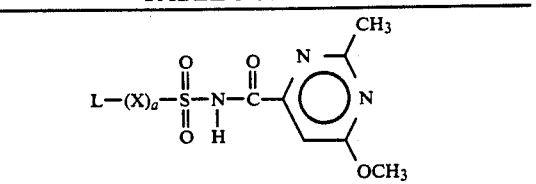

| Ex. No. | L | X | a | m.p. [°C.] |
|---|---|---|---|---|
| 122 | L1-54 | $CH_2$ | 1 | |
| 123 | L1-55 | $CH_2$ | 1 | |
| 124 | L1-56 | $CH_2$ | 1 | |
| 125 | L1-57 | $CH_2$ | 1 | |
| 126 | L1-58 | $CH_2$ | 1 | |
| 127 | L1-59 | $CH_2$ | 1 | |
| 128 | L1-60 | $CH_2$ | 1 | |
| 129 | L1-61 | $CH_2$ | 1 | |
| 130 | L1-62 | $CH_2$ | 1 | |
| 131 | L1-63 | $CH_2$ | 1 | |
| 132 | L1-64 | $CH_2$ | 1 | |
| 133 | L1-65 | $CH_2$ | 1 | |
| 134 | L1-66 | $CH_2$ | 1 | |
| 135 | L1-67 | $CH_2$ | 1 | |
| 136 | L1-68 | $CH_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-19 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |

TABLE 3-continued

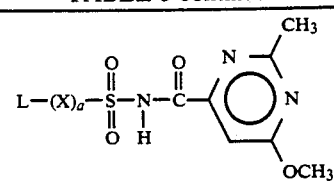

| Ex. No. | L | X | a | m.p. [°C.] |
|---|---|---|---|---|
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 219 | L1-15 | NH | 1 | |
| 220 | L1-16 | NH | 1 | |
| 221 | L1-17 | NH | 1 | |
| 222 | L1-18 | NH | 1 | |
| 223 | L1-19 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |

TABLE 3-continued

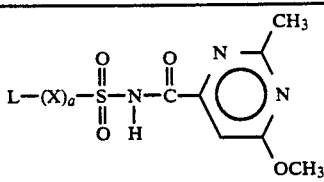

| Ex. No. | L | X | a | m.p. [°C.] |
|---|---|---|---|---|
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH₂ | 1 | |
| 279 | L3-2 | CH₂ | 1 | |
| 280 | L3-3 | CH₂ | 1 | |
| 281 | L3-4 | CH₂ | 1 | |
| 282 | L3-5 | CH₂ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH₂ | 1 | |
| 299 | L4-2 | CH₂ | 1 | |
| 300 | L4-3 | CH₂ | 1 | |
| 301 | L4-4 | CH₂ | 1 | |
| 302 | L4-5 | CH₂ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 319 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-19 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH₂ | 1 | |

TABLE 3-continued

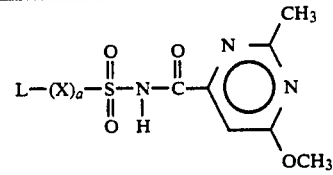

| Ex. No. | L | X | a | m.p. [°C.] |
|---|---|---|---|---|
| 338 | L5-2 | CH₂ | 1 | |
| 339 | L5-3 | CH₂ | 1 | |
| 340 | L5-4 | CH₂ | 1 | |
| 341 | L5-5 | CH₂ | 1 | |
| 342 | L5-6 | CH₂ | 1 | |
| 343 | L5-7 | CH₂ | 1 | |
| 344 | L5-8 | CH₂ | 1 | |
| 345 | L5-9 | CH₂ | 1 | |
| 346 | L5-10 | CH₂ | 1 | |
| 347 | L5-11 | CH₂ | 1 | |
| 348 | L5-12 | CH₂ | 1 | |
| 349 | L5-13 | CH₂ | 1 | |
| 350 | L5-14 | CH₂ | 1 | |
| 351 | L5-15 | CH₂ | 1 | |
| 352 | L5-16 | CH₂ | 1 | |
| 353 | L5-17 | CH₂ | 1 | |
| 354 | L5-18 | CH₂ | 1 | |
| 355 | L5-19 | CH₂ | 1 | |
| 356 | L5-20 | CH₂ | 1 | |
| 357 | L5-21 | CH₂ | 1 | |
| 358 | L5-22 | CH₂ | 1 | |
| 359 | L5-23 | CH₂ | 1 | |
| 360 | L5-24 | CH₂ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-19 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 192 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 399 | L5-15 | NH | 1 | |
| 400 | L5-16 | NH | 1 | |
| 401 | L5-17 | NH | 1 | |
| 402 | L5-18 | NH | 1 | |
| 403 | L5-19 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |

TABLE 3-continued

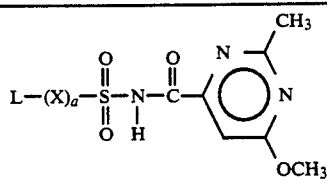

| Ex. No. | L | X | a | m.p. [°C.] |
|---|---|---|---|---|
| 408 | L5-24 | NH | 1 | |

TABLE 4

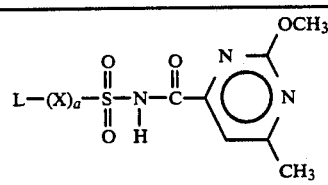

| Ex. No. | L | X | a | m.p. [°C.] |
|---|---|---|---|---|
| 1 | L1-1 | — | 0 | 145–146 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 168–169 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 158–160 |
| 27 | L1-27 | — | 0 | |
| 28 | L1-28 | — | 0 | 212–216 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | 174–176 |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | 138–140 |
| 54 | L1-54 | — | 0 | |
| 55 | L1-55 | — | 0 | |
| 56 | L1-56 | — | 0 | |

TABLE 4-continued

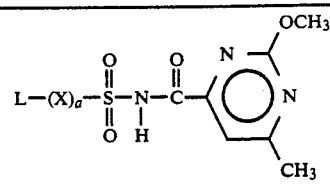

| Ex. No. | L | X | a | m.p. [°C.] |
|---|---|---|---|---|
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | $CH_2$ | 1 | 115–118 |
| 70 | L1-2 | $CH_2$ | 1 | |
| 71 | L1-3 | $CH_2$ | 1 | |
| 72 | L1-4 | $CH_2$ | 1 | |
| 73 | L1-5 | $CH_2$ | 1 | |
| 74 | L1-6 | $CH_2$ | 1 | |
| 75 | L1-7 | $CH_2$ | 1 | |
| 76 | L1-8 | $CH_2$ | 1 | 171–172 |
| 77 | L1-9 | $CH_2$ | 1 | |
| 78 | L1-10 | $CH_2$ | 1 | |
| 79 | L1-11 | $CH_2$ | 1 | |
| 80 | L1-12 | $CH_2$ | 1 | |
| 81 | L1-13 | $CH_2$ | 1 | |
| 82 | L1-14 | $CH_2$ | 1 | |
| 83 | L1-15 | $CH_2$ | 1 | 184–187 |
| 84 | L1-16 | $CH_2$ | 1 | 133–134 |
| 85 | L1-17 | $CH_2$ | 1 | |
| 86 | L1-18 | $CH_2$ | 1 | |
| 87 | L1-19 | $CH_2$ | 1 | |
| 88 | L1-20 | $CH_2$ | 1 | |
| 89 | L1-21 | $CH_2$ | 1 | |
| 90 | L1-22 | $CH_2$ | 1 | |
| 91 | L1-23 | $CH_2$ | 1 | |
| 92 | L1-24 | $CH_2$ | 1 | |
| 93 | L1-25 | $CH_2$ | 1 | |
| 94 | L1-26 | $CH_2$ | 1 | 171–173 |
| 95 | L1-27 | $CH_2$ | 1 | |
| 96 | L1-28 | $CH_2$ | 1 | 178–179 |
| 97 | L1-29 | $CH_2$ | 1 | |
| 98 | L1-30 | $CH_2$ | 1 | |
| 99 | L1-31 | $CH_2$ | 1 | |
| 100 | L1-32 | $CH_2$ | 1 | |
| 101 | L1-33 | $CH_2$ | 1 | |
| 102 | L1-34 | $CH_2$ | 1 | |
| 103 | L1-35 | $CH_2$ | 1 | |
| 104 | L1-36 | $CH_2$ | 1 | |
| 105 | L1-37 | $CH_2$ | 1 | |
| 106 | L1-38 | $CH_2$ | 1 | 146–148 |
| 107 | L1-39 | $CH_2$ | 1 | |
| 108 | L1-40 | $CH_2$ | 1 | |
| 109 | L1-41 | $CH_2$ | 1 | |
| 110 | L1-42 | $CH_2$ | 1 | |
| 111 | L1-43 | $CH_2$ | 1 | |
| 112 | L1-44 | $CH_2$ | 1 | 163–166 |
| 113 | L1-45 | $CH_2$ | 1 | |
| 114 | L1-46 | $CH_2$ | 1 | |
| 115 | L1-47 | $CH_2$ | 1 | |
| 116 | L1-48 | $CH_2$ | 1 | |
| 117 | L1-49 | $CH_2$ | 1 | |
| 118 | L1-50 | $CH_2$ | 1 | |
| 119 | L1-51 | $CH_2$ | 1 | |
| 120 | L1-52 | $CH_2$ | 1 | 151–153 |
| 121 | L1-53 | $CH_2$ | 1 | 100–101 |
| 122 | L1-54 | $CH_2$ | 1 | 162–164 |
| 123 | L1-55 | $CH_2$ | 1 | |
| 124 | L1-56 | $CH_2$ | 1 | |
| 125 | L1-57 | $CH_2$ | 1 | |
| 126 | L1-58 | $CH_2$ | 1 | |
| 127 | L1-59 | $CH_2$ | 1 | 170–172 |
| 128 | L1-60 | $CH_2$ | 1 | |

TABLE 4-continued

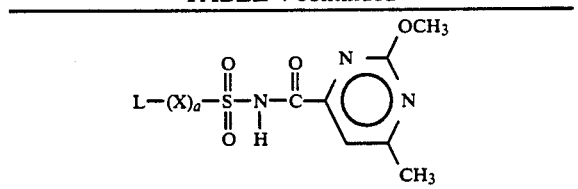

| Ex. No. | L | X | a | m.p. [°C.] |
|---|---|---|---|---|
| 129 | L1-61 | CH$_2$ | 1 | 150 |
| 130 | L1-62 | CH$_2$ | 1 | |
| 131 | L1-63 | CH$_2$ | 1 | |
| 132 | L1-64 | CH$_2$ | 1 | |
| 133 | L1-65 | CH$_2$ | 1 | |
| 134 | L1-66 | CH$_2$ | 1 | |
| 135 | L1-67 | CH$_2$ | 1 | |
| 136 | L1-68 | CH$_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-19 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |

TABLE 4-continued

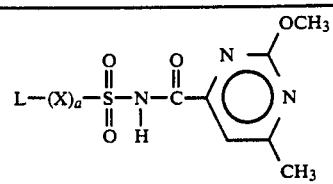

| Ex. No. | L | X | a | m.p. [°C.] |
|---|---|---|---|---|
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 219 | L1-15 | NH | 1 | |
| 220 | L1-16 | NH | 1 | |
| 221 | L1-17 | NH | 1 | |
| 222 | L1-18 | NH | 1 | |
| 223 | L1-19 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | 133–134 |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | 170 |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | 154–156 |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |

TABLE 4-continued

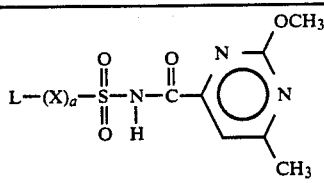

| Ex. No. | L | X | a | m.p. [°C.] |
|---|---|---|---|---|
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH$_2$ | 1 | |
| 299 | L4-2 | CH$_2$ | 1 | |
| 300 | L4-3 | CH$_2$ | 1 | |
| 301 | L4-4 | CH$_2$ | 1 | |
| 302 | L4-5 | CH$_2$ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 319 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-19 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH$_2$ | 1 | |
| 338 | L5-2 | CH$_2$ | 1 | |
| 339 | L5-3 | CH$_2$ | 1 | |
| 340 | L5-4 | CH$_2$ | 1 | |
| 341 | L5-5 | CH$_2$ | 1 | |
| 342 | L5-6 | CH$_2$ | 1 | 170–172 |
| 343 | L5-7 | CH$_2$ | 1 | 235–236 |
| 344 | L5-8 | CH$_2$ | 1 | |

TABLE 4-continued

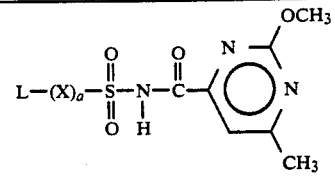

| Ex. No. | L | X | a | m.p. [°C.] |
|---|---|---|---|---|
| 345 | L5-9 | CH$_2$ | 1 | |
| 346 | L5-10 | CH$_2$ | 1 | |
| 347 | L5-11 | CH$_2$ | 1 | |
| 348 | L5-12 | CH$_2$ | 1 | |
| 349 | L5-13 | CH$_2$ | 1 | |
| 350 | L5-14 | CH$_2$ | 1 | |
| 351 | L5-15 | CH$_2$ | 1 | |
| 352 | L5-16 | CH$_2$ | 1 | |
| 353 | L5-17 | CH$_2$ | 1 | |
| 354 | L5-18 | CH$_2$ | 1 | |
| 355 | L5-19 | CH$_2$ | 1 | |
| 356 | L5-20 | CH$_2$ | 1 | |
| 357 | L5-21 | CH$_2$ | 1 | |
| 358 | L5-22 | CH$_2$ | 1 | |
| 359 | L5-23 | CH$_2$ | 1 | |
| 360 | L5-24 | CH$_2$ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-19 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 192 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 399 | L5-15 | NH | 1 | |
| 400 | L5-16 | NH | 1 | |
| 401 | L5-17 | NH | 1 | |
| 402 | L5-18 | NH | 1 | |
| 403 | L5-19 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 5

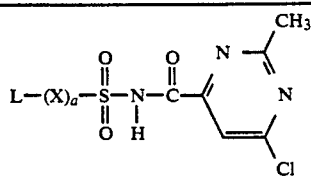

| Ex. No. | L | X | a | m.p. [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 134–135 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | CH$_2$ | 1 | |
| 70 | L1-2 | CH$_2$ | 1 | |
| 71 | L1-3 | CH$_2$ | 1 | |
| 72 | L1-4 | CH$_2$ | 1 | |

TABLE 5-continued

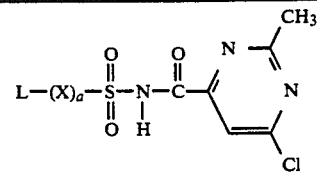

| Ex. No. | L | X | a | m.p. [°C.] |
|---|---|---|---|---|
| 73 | L1-5 | CH$_2$ | 1 | |
| 74 | L1-6 | CH$_2$ | 1 | |
| 75 | L1-7 | CH$_2$ | 1 | |
| 76 | L1-8 | CH$_2$ | 1 | 186–189 |
| 77 | L1-9 | CH$_2$ | 1 | |
| 78 | L1-10 | CH$_2$ | 1 | |
| 79 | L1-11 | CH$_2$ | 1 | |
| 80 | L1-12 | CH$_2$ | 1 | |
| 81 | L1-13 | CH$_2$ | 1 | |
| 82 | L1-14 | CH$_2$ | 1 | |
| 83 | L1-15 | CH$_2$ | 1 | |
| 84 | L1-16 | CH$_2$ | 1 | |
| 85 | L1-17 | CH$_2$ | 1 | |
| 86 | L1-18 | CH$_2$ | 1 | |
| 87 | L1-19 | CH$_2$ | 1 | |
| 88 | L1-20 | CH$_2$ | 1 | |
| 89 | L1-21 | CH$_2$ | 1 | |
| 90 | L1-22 | CH$_2$ | 1 | |
| 91 | L1-23 | CH$_2$ | 1 | |
| 92 | L1-24 | CH$_2$ | 1 | |
| 93 | L1-25 | CH$_2$ | 1 | |
| 94 | L1-26 | CH$_2$ | 1 | |
| 95 | L1-27 | CH$_2$ | 1 | |
| 96 | L1-28 | CH$_2$ | 1 | 190–192 |
| 97 | L1-29 | CH$_2$ | 1 | |
| 98 | L1-30 | CH$_2$ | 1 | |
| 99 | L1-31 | CH$_2$ | 1 | |
| 100 | L1-32 | CH$_2$ | 1 | |
| 101 | L1-33 | CH$_2$ | 1 | |
| 102 | L1-34 | CH$_2$ | 1 | |
| 103 | L1-35 | CH$_2$ | 1 | |
| 104 | L1-36 | CH$_2$ | 1 | |
| 105 | L1-37 | CH$_2$ | 1 | |
| 106 | L1-38 | CH$_2$ | 1 | |
| 107 | L1-39 | CH$_2$ | 1 | |
| 108 | L1-40 | CH$_2$ | 1 | |
| 109 | L1-41 | CH$_2$ | 1 | |
| 110 | L1-42 | CH$_2$ | 1 | |
| 111 | L1-43 | CH$_2$ | 1 | |
| 112 | L1-44 | CH$_2$ | 1 | |
| 113 | L1-45 | CH$_2$ | 1 | |
| 114 | L1-46 | CH$_2$ | 1 | |
| 115 | L1-47 | CH$_2$ | 1 | |
| 116 | L1-48 | CH$_2$ | 1 | |
| 117 | L1-49 | CH$_2$ | 1 | |
| 118 | L1-50 | CH$_2$ | 1 | |
| 119 | L1-51 | CH$_2$ | 1 | |
| 120 | L1-52 | CH$_2$ | 1 | |
| 121 | L1-53 | CH$_2$ | 1 | |
| 122 | L1-54 | CH$_2$ | 1 | |
| 123 | L1-55 | CH$_2$ | 1 | |
| 124 | L1-56 | CH$_2$ | 1 | |
| 125 | L1-57 | CH$_2$ | 1 | |
| 126 | L1-58 | CH$_2$ | 1 | |
| 127 | L1-59 | CH$_2$ | 1 | |
| 128 | L1-60 | CH$_2$ | 1 | |
| 129 | L1-61 | CH$_2$ | 1 | |
| 130 | L1-62 | CH$_2$ | 1 | |
| 131 | L1-63 | CH$_2$ | 1 | |
| 132 | L1-64 | CH$_2$ | 1 | |
| 133 | L1-65 | CH$_2$ | 1 | |
| 134 | L1-66 | CH$_2$ | 1 | |
| 135 | L1-67 | CH$_2$ | 1 | |
| 136 | L1-68 | CH$_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |

TABLE 5-continued

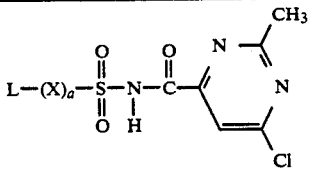

| Ex. No. | L | X | a | m.p. [°C.] |
|---|---|---|---|---|
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-19 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |

TABLE 5-continued

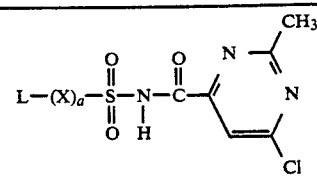

| Ex. No. | L | X | a | m.p. [°C.] |
|---|---|---|---|---|
| 217 | L1-13 | NH | 1 | |
| 218 | L1-14 | NH | 1 | |
| 219 | L1-15 | NH | 1 | |
| 220 | L1-16 | NH | 1 | |
| 221 | L1-17 | NH | 1 | |
| 222 | L1-18 | NH | 1 | |
| 223 | L1-19 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |

TABLE 5-continued

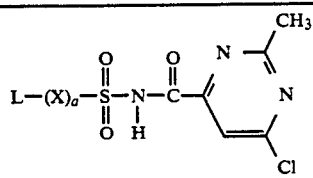

| Ex. No. | L | X | a | m.p. [°C.] |
|---|---|---|---|---|
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH₂ | 1 | |
| 299 | L4-2 | CH₂ | 1 | |
| 300 | L4-3 | CH₂ | 1 | |
| 301 | L4-4 | CH₂ | 1 | |
| 302 | L4-5 | CH₂ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 319 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-19 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH₂ | 1 | |
| 338 | L5-2 | CH₂ | 1 | |
| 339 | L5-3 | CH₂ | 1 | |
| 340 | L5-4 | CH₂ | 1 | |
| 341 | L5-5 | CH₂ | 1 | |
| 342 | L5-6 | CH₂ | 1 | |
| 343 | L5-7 | CH₂ | 1 | |
| 344 | L5-8 | CH₂ | 1 | |
| 345 | L5-9 | CH₂ | 1 | |
| 346 | L5-10 | CH₂ | 1 | |
| 347 | L5-11 | CH₂ | 1 | |
| 348 | L5-12 | CH₂ | 1 | |
| 349 | L5-13 | CH₂ | 1 | |
| 350 | L5-14 | CH₂ | 1 | |
| 351 | L5-15 | CH₂ | 1 | |
| 352 | L5-16 | CH₂ | 1 | |
| 353 | L5-17 | CH₂ | 1 | |
| 354 | L5-18 | CH₂ | 1 | |
| 355 | L5-19 | CH₂ | 1 | |
| 356 | L5-20 | CH₂ | 1 | |
| 357 | L5-21 | CH₂ | 1 | |
| 358 | L5-22 | CH₂ | 1 | |
| 359 | L5-23 | CH₂ | 1 | |
| 360 | L5-24 | CH₂ | 1 | |

TABLE 5-continued

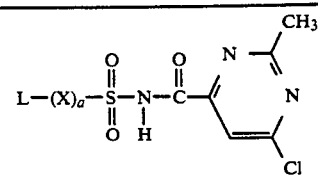

| Ex. No. | L | X | a | m.p. [°C.] |
|---|---|---|---|---|
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-19 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 192 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 399 | L5-15 | NH | 1 | |
| 400 | L5-16 | NH | 1 | |
| 401 | L5-17 | NH | 1 | |
| 402 | L5-18 | NH | 1 | |
| 403 | L5-19 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 6

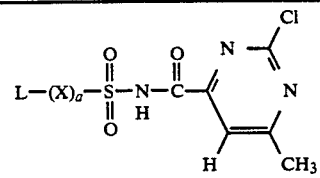

| Ex. No. | L | X | a | m.p. [°C.] |
|---|---|---|---|---|
| 1 | L1-1 | — | 0 | 144–145 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 182–184 |
| 9 | L1-9 | — | 0 | |

TABLE 6-continued

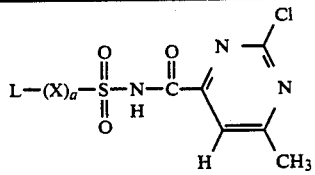

| Ex. No. | L | X | a | m.p. [°C.] |
|---|---|---|---|---|
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | 125–128 |
| 17 | L1-17 | — | 0 | |
| 18 | L1-18 | — | 0 | |
| 29 | L1-29 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 165–166 |
| 27 | L1-27 | — | 0 | |
| 28 | L1-28 | — | 0 | 181–182 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | $CH_2$ | 1 | 126–127 |
| 70 | L1-2 | $CH_2$ | 1 | |
| 71 | L1-3 | $CH_2$ | 1 | |
| 72 | L1-4 | $CH_2$ | 1 | |
| 73 | L1-5 | $CH_2$ | 1 | |
| 74 | L1-6 | $CH_2$ | 1 | |
| 75 | L1-7 | $CH_2$ | 1 | |
| 76 | L1-8 | $CH_2$ | 1 | 198–199 |
| 77 | L1-9 | $CH_2$ | 1 | |
| 78 | L1-10 | $CH_2$ | 1 | |
| 79 | L1-11 | $CH_2$ | 1 | |
| 80 | L1-12 | $CH_2$ | 1 | |
| 81 | L1-13 | $CH_2$ | 1 | |

TABLE 6-continued

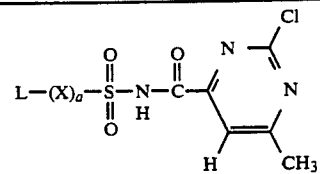

| Ex. No. | L | X | a | m.p. [°C.] |
|---|---|---|---|---|
| 82 | L1-14 | $CH_2$ | 1 | |
| 83 | L1-15 | $CH_2$ | 1 | 162 |
| 84 | L1-16 | $CH_2$ | 1 | 132–133 |
| 85 | L1-17 | $CH_2$ | 1 | |
| 86 | L1-18 | $CH_2$ | 1 | |
| 87 | L1-29 | $CH_2$ | 1 | |
| 88 | L1-20 | $CH_2$ | 1 | |
| 89 | L1-21 | $CH_2$ | 1 | |
| 90 | L1-22 | $CH_2$ | 1 | |
| 91 | L1-23 | $CH_2$ | 1 | |
| 92 | L1-24 | $CH_2$ | 1 | |
| 93 | L1-25 | $CH_2$ | 1 | |
| 94 | L1-26 | $CH_2$ | 1 | 182–183 |
| 95 | L1-27 | $CH_2$ | 1 | |
| 96 | L1-28 | $CH_2$ | 1 | 184–186 |
| 97 | L1-29 | $CH_2$ | 1 | |
| 98 | L1-30 | $CH_2$ | 1 | |
| 99 | L1-31 | $CH_2$ | 1 | |
| 100 | L1-32 | $CH_2$ | 1 | |
| 101 | L1-33 | $CH_2$ | 1 | |
| 102 | L1-34 | $CH_2$ | 1 | |
| 103 | L1-35 | $CH_2$ | 1 | |
| 104 | L1-36 | $CH_2$ | 1 | |
| 105 | L1-37 | $CH_2$ | 1 | |
| 106 | L1-38 | $CH_2$ | 1 | |
| 107 | L1-39 | $CH_2$ | 1 | |
| 108 | L1-40 | $CH_2$ | 1 | |
| 109 | L1-41 | $CH_2$ | 1 | |
| 110 | L1-42 | $CH_2$ | 1 | |
| 111 | L1-43 | $CH_2$ | 1 | |
| 112 | L1-44 | $CH_2$ | 1 | |
| 113 | L1-45 | $CH_2$ | 1 | |
| 114 | L1-46 | $CH_2$ | 1 | |
| 115 | L1-47 | $CH_2$ | 1 | |
| 116 | L1-48 | $CH_2$ | 1 | |
| 117 | L1-49 | $CH_2$ | 1 | |
| 118 | L1-50 | $CH_2$ | 1 | |
| 129 | L1-51 | $CH_2$ | 1 | |
| 120 | L1-52 | $CH_2$ | 1 | |
| 121 | L1-53 | $CH_2$ | 1 | 145–146 |
| 122 | L1-54 | $CH_2$ | 1 | 174–176 |
| 123 | L1-55 | $CH_2$ | 1 | |
| 124 | L1-56 | $CH_2$ | 1 | |
| 125 | L1-57 | $CH_2$ | 1 | |
| 126 | L1-58 | $CH_2$ | 1 | |
| 127 | L1-59 | $CH_2$ | 1 | |
| 128 | L1-60 | $CH_2$ | 1 | |
| 129 | L1-61 | $CH_2$ | 1 | 171–172 |
| 130 | L1-62 | $CH_2$ | 1 | |
| 131 | L1-63 | $CH_2$ | 1 | |
| 132 | L1-64 | $CH_2$ | 1 | |
| 133 | L1-65 | $CH_2$ | 1 | |
| 134 | L1-66 | $CH_2$ | 1 | |
| 135 | L1-67 | $CH_2$ | 1 | |
| 136 | L1-68 | $CH_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |

TABLE 6-continued

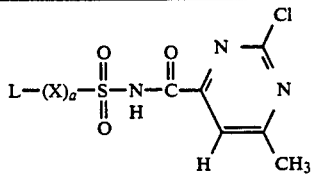

| Ex. No. | L | X | a | m.p. [°C.] |
|---|---|---|---|---|
| 154 | L1-18 | O | 1 | |
| 155 | L1-29 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 229 | L1-15 | NH | 1 | |
| 220 | L1-16 | NH | 1 | |
| 221 | L1-17 | NH | 1 | |
| 222 | L1-18 | NH | 1 | |
| 223 | L1-29 | NH | 1 | |
| 224 | L1-20 | NH | 1 | |
| 225 | L1-21 | NH | 1 | |

TABLE 6-continued

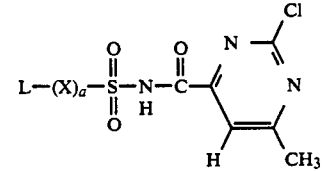

| Ex. No. | L | X | a | m.p. [°C.] |
|---|---|---|---|---|
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |

TABLE 6-continued

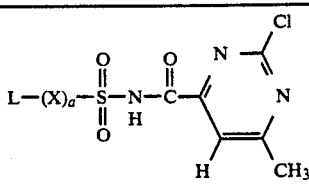

| Ex. No. | L | X | a | m.p. [°C.] |
|---|---|---|---|---|
| 298 | L4-1 | CH₂ | 1 | |
| 299 | L4-2 | CH₂ | 1 | |
| 300 | L4-3 | CH₂ | 1 | |
| 301 | L4-4 | CH₂ | 1 | |
| 302 | L4-5 | CH₂ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 329 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-29 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH₂ | 1 | |
| 338 | L5-2 | CH₂ | 1 | |
| 339 | L5-3 | CH₂ | 1 | |
| 340 | L5-4 | CH₂ | 1 | |
| 341 | L5-5 | CH₂ | 1 | |
| 342 | L5-6 | CH₂ | 1 | |
| 343 | L5-7 | CH₂ | 1 | |
| 344 | L5-8 | CH₂ | 1 | |
| 345 | L5-9 | CH₂ | 1 | |
| 346 | L5-10 | CH₂ | 1 | |
| 347 | L5-11 | CH₂ | 1 | |
| 348 | L5-12 | CH₂ | 1 | |
| 349 | L5-13 | CH₂ | 1 | |
| 350 | L5-14 | CH₂ | 1 | |
| 351 | L5-15 | CH₂ | 1 | |
| 352 | L5-16 | CH₂ | 1 | |
| 353 | L5-17 | CH₂ | 1 | |
| 354 | L5-18 | CH₂ | 1 | |
| 355 | L5-29 | CH₂ | 1 | |
| 356 | L5-20 | CH₂ | 1 | |
| 357 | L5-21 | CH₂ | 1 | |
| 358 | L5-22 | CH₂ | 1 | |
| 359 | L5-23 | CH₂ | 1 | |
| 360 | L5-24 | CH₂ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |

TABLE 6-continued

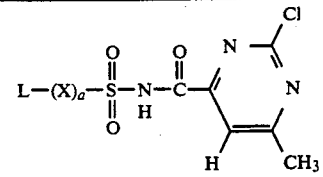

| Ex. No. | L | X | a | m.p. [°C.] |
|---|---|---|---|---|
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-29 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 392 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 499 | L5-15 | NH | 1 | |
| 400 | L5-16 | NH | 1 | |
| 401 | L5-17 | NH | 1 | |
| 402 | L5-18 | NH | 1 | |
| 403 | L5-29 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 7

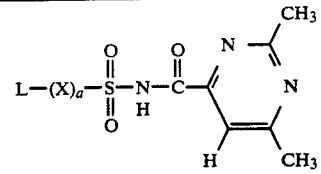

| Ex. No. | L | X | a | m.p. [°C.] |
|---|---|---|---|---|
| 1 | L1-1 | — | 0 | 152 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 147–150 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |

TABLE 7-continued

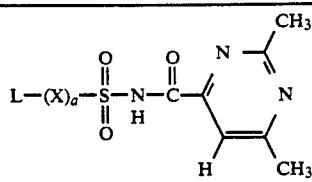

| Ex. No. | L | X | a | m.p. [°C.] |
|---|---|---|---|---|
| 29 | L1-29 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 164–165 |
| 27 | L1-27 | — | 0 | |
| 28 | L1-28 | — | 0 | 154–157 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | 166–167 |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | CH$_2$ | 1 | 155 |
| 70 | L1-2 | CH$_2$ | 1 | |
| 71 | L1-3 | CH$_2$ | 1 | |
| 72 | L1-4 | CH$_2$ | 1 | |
| 73 | L1-5 | CH$_2$ | 1 | |
| 74 | L1-6 | CH$_2$ | 1 | |
| 75 | L1-7 | CH$_2$ | 1 | |
| 76 | L1-8 | CH$_2$ | 1 | 145 |
| 77 | L1-9 | CH$_2$ | 1 | |
| 78 | L1-10 | CH$_2$ | 1 | |
| 79 | L1-11 | CH$_2$ | 1 | |
| 80 | L1-12 | CH$_2$ | 1 | |
| 81 | L1-13 | CH$_2$ | 1 | |
| 82 | L1-14 | CH$_2$ | 1 | |
| 83 | L1-15 | CH$_2$ | 1 | |
| 84 | L1-16 | CH$_2$ | 1 | |
| 85 | L1-17 | CH$_2$ | 1 | |
| 86 | L1-18 | CH$_2$ | 1 | |
| 87 | L1-29 | CH$_2$ | 1 | |
| 88 | L1-20 | CH$_2$ | 1 | |
| 89 | L1-21 | CH$_2$ | 1 | |
| 90 | L1-22 | CH$_2$ | 1 | |

TABLE 7-continued

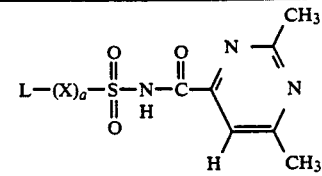

| Ex. No. | L | X | a | m.p. [°C.] |
|---|---|---|---|---|
| 91 | L1-23 | CH$_2$ | 1 | |
| 92 | L1-24 | CH$_2$ | 1 | |
| 93 | L1-25 | CH$_2$ | 1 | |
| 94 | L1-26 | CH$_2$ | 1 | 175–179 |
| 95 | L1-27 | CH$_2$ | 1 | |
| 96 | L1-28 | CH$_2$ | 1 | 200–206 |
| 97 | L1-29 | CH$_2$ | 1 | |
| 98 | L1-30 | CH$_2$ | 1 | |
| 99 | L1-31 | CH$_2$ | 1 | |
| 100 | L1-32 | CH$_2$ | 1 | |
| 101 | L1-33 | CH$_2$ | 1 | |
| 102 | L1-34 | CH$_2$ | 1 | |
| 103 | L1-35 | CH$_2$ | 1 | |
| 104 | L1-36 | CH$_2$ | 1 | |
| 105 | L1-37 | CH$_2$ | 1 | |
| 106 | L1-38 | CH$_2$ | 1 | |
| 107 | L1-39 | CH$_2$ | 1 | |
| 108 | L1-40 | CH$_2$ | 1 | |
| 109 | L1-41 | CH$_2$ | 1 | |
| 110 | L1-42 | CH$_2$ | 1 | |
| 111 | L1-43 | CH$_2$ | 1 | |
| 112 | L1-44 | CH$_2$ | 1 | |
| 113 | L1-45 | CH$_2$ | 1 | |
| 114 | L1-46 | CH$_2$ | 1 | |
| 115 | L1-47 | CH$_2$ | 1 | |
| 116 | L1-48 | CH$_2$ | 1 | |
| 117 | L1-49 | CH$_2$ | 1 | |
| 118 | L1-50 | CH$_2$ | 1 | |
| 129 | L1-51 | CH$_2$ | 1 | |
| 120 | L1-52 | CH$_2$ | 1 | |
| 121 | L1-53 | CH$_2$ | 1 | |
| 122 | L1-54 | CH$_2$ | 1 | 167–169 |
| 123 | L1-55 | CH$_2$ | 1 | |
| 124 | L1-56 | CH$_2$ | 1 | |
| 125 | L1-57 | CH$_2$ | 1 | |
| 126 | L1-58 | CH$_2$ | 1 | |
| 127 | L1-59 | CH$_2$ | 1 | |
| 128 | L1-60 | CH$_2$ | 1 | |
| 129 | L1-61 | CH$_2$ | 1 | |
| 130 | L1-62 | CH$_2$ | 1 | |
| 131 | L1-63 | CH$_2$ | 1 | |
| 132 | L1-64 | CH$_2$ | 1 | |
| 133 | L1-65 | CH$_2$ | 1 | |
| 134 | L1-66 | CH$_2$ | 1 | |
| 135 | L1-67 | CH$_2$ | 1 | |
| 136 | L1-68 | CH$_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-29 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |

TABLE 7-continued

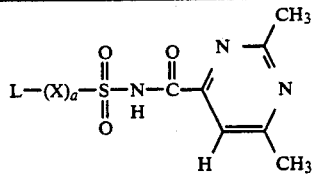

| Ex. No. | L | X | a | m.p. [°C.] |
|---|---|---|---|---|
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 229 | L1-15 | NH | 1 | |
| 220 | L1-16 | NH | 1 | |
| 221 | L1-17 | NH | 1 | |
| 222 | L1-18 | NH | 1 | |
| 223 | L1-29 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |

TABLE 7-continued

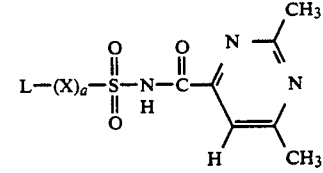

| Ex. No. | L | X | a | m.p. [°C.] |
|---|---|---|---|---|
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | $CH_2$ | 1 | |
| 279 | L3-2 | $CH_2$ | 1 | |
| 280 | L3-3 | $CH_2$ | 1 | |
| 281 | L3-4 | $CH_2$ | 1 | |
| 282 | L3-5 | $CH_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | $CH_2$ | 1 | |
| 299 | L4-2 | $CH_2$ | 1 | |
| 300 | L4-3 | $CH_2$ | 1 | |
| 301 | L4-4 | $CH_2$ | 1 | |
| 302 | L4-5 | $CH_2$ | 1 | |
| 303 | L4-1 | O | 1 | |
| 304 | L4-2 | O | 1 | |
| 305 | L4-3 | O | 1 | |
| 306 | L4-4 | O | 1 | |

TABLE 7-continued

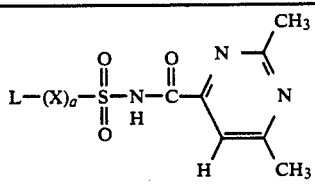

| Ex. No. | L | X | a | m.p. [°C.] |
|---|---|---|---|---|
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 329 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-29 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH$_2$ | 1 | |
| 338 | L5-2 | CH$_2$ | 1 | |
| 339 | L5-3 | CH$_2$ | 1 | |
| 340 | L5-4 | CH$_2$ | 1 | |
| 341 | L5-5 | CH$_2$ | 1 | |
| 342 | L5-6 | CH$_2$ | 1 | |
| 343 | L5-7 | CH$_2$ | 1 | |
| 344 | L5-8 | CH$_2$ | 1 | |
| 345 | L5-9 | CH$_2$ | 1 | |
| 346 | L5-10 | CH$_2$ | 1 | |
| 347 | L5-11 | CH$_2$ | 1 | |
| 348 | L5-12 | CH$_2$ | 1 | |
| 349 | L5-13 | CH$_2$ | 1 | |
| 350 | L5-14 | CH$_2$ | 1 | |
| 351 | L5-15 | CH$_2$ | 1 | |
| 352 | L5-16 | CH$_2$ | 1 | |
| 353 | L5-17 | CH$_2$ | 1 | |
| 354 | L5-18 | CH$_2$ | 1 | |
| 355 | L5-29 | CH$_2$ | 1 | |
| 356 | L5-20 | CH$_2$ | 1 | |
| 357 | L5-21 | CH$_2$ | 1 | |
| 358 | L5-22 | CH$_2$ | 1 | |
| 359 | L5-23 | CH$_2$ | 1 | |
| 360 | L5-24 | CH$_2$ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |

TABLE 7-continued

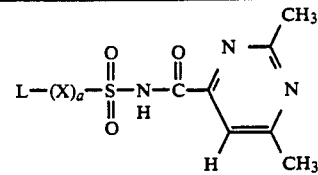

| Ex. No. | L | X | a | m.p. [°C.] |
|---|---|---|---|---|
| 379 | L5-29 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 392 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 499 | L5-15 | NH | 1 | |
| 400 | L5-16 | NH | 1 | |
| 401 | L5-17 | NH | 1 | |
| 402 | L5-18 | NH | 1 | |
| 403 | L5-29 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 8

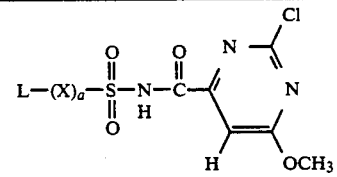

| Ex. No. | L | X | a | m.p. [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 29 | L1-29 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |

TABLE 8-continued

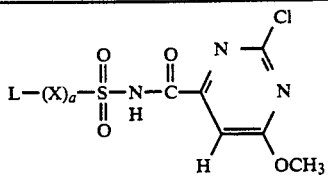
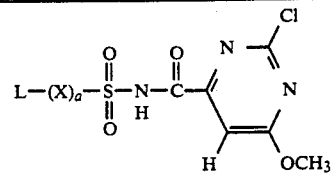

| Ex. No. | L | X | a | m.p. [°C.] |
|---|---|---|---|---|
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | CH$_2$ | 1 | |
| 70 | L1-2 | CH$_2$ | 1 | |
| 71 | L1-3 | CH$_2$ | 1 | |
| 72 | L1-4 | CH$_2$ | 1 | |
| 73 | L1-5 | CH$_2$ | 1 | |
| 74 | L1-6 | CH$_2$ | 1 | |
| 75 | L1-7 | CH$_2$ | 1 | |
| 76 | L1-8 | CH$_2$ | 1 | |
| 77 | L1-9 | CH$_2$ | 1 | |
| 78 | L1-10 | CH$_2$ | 1 | |
| 79 | L1-11 | CH$_2$ | 1 | |
| 80 | L1-12 | CH$_2$ | 1 | |
| 81 | L1-13 | CH$_2$ | 1 | |
| 82 | L1-14 | CH$_2$ | 1 | |
| 83 | L1-15 | CH$_2$ | 1 | |
| 84 | L1-16 | CH$_2$ | 1 | |
| 85 | L1-17 | CH$_2$ | 1 | |
| 86 | L1-18 | CH$_2$ | 1 | |
| 87 | L1-29 | CH$_2$ | 1 | |
| 88 | L1-20 | CH$_2$ | 1 | |
| 89 | L1-21 | CH$_2$ | 1 | |
| 90 | L1-22 | CH$_2$ | 1 | |
| 91 | L1-23 | CH$_2$ | 1 | |
| 92 | L1-24 | CH$_2$ | 1 | |
| 93 | L1-25 | CH$_2$ | 1 | |
| 94 | L1-26 | CH$_2$ | 1 | |
| 95 | L1-27 | CH$_2$ | 1 | |
| 96 | L1-28 | CH$_2$ | 1 | |
| 97 | L1-29 | CH$_2$ | 1 | |
| 98 | L1-30 | CH$_2$ | 1 | |
| 99 | L1-31 | CH$_2$ | 1 | |
| 100 | L1-32 | CH$_2$ | 1 | |
| 101 | L1-33 | CH$_2$ | 1 | |
| 102 | L1-34 | CH$_2$ | 1 | |
| 103 | L1-35 | CH$_2$ | 1 | |
| 104 | L1-36 | CH$_2$ | 1 | |
| 105 | L1-37 | CH$_2$ | 1 | |
| 106 | L1-38 | CH$_2$ | 1 | |
| 107 | L1-39 | CH$_2$ | 1 | |
| 108 | L1-40 | CH$_2$ | 1 | |
| 109 | L1-41 | CH$_2$ | 1 | |
| 110 | L1-42 | CH$_2$ | 1 | |
| 111 | L1-43 | CH$_2$ | 1 | |
| 112 | L1-44 | CH$_2$ | 1 | |
| 113 | L1-45 | CH$_2$ | 1 | |
| 114 | L1-46 | CH$_2$ | 1 | |
| 115 | L1-47 | CH$_2$ | 1 | |
| 116 | L1-48 | CH$_2$ | 1 | |
| 117 | L1-49 | CH$_2$ | 1 | |
| 118 | L1-50 | CH$_2$ | 1 | |
| 129 | L1-51 | CH$_2$ | 1 | |
| 120 | L1-52 | CH$_2$ | 1 | |
| 121 | L1-53 | CH$_2$ | 1 | |
| 122 | L1-54 | CH$_2$ | 1 | |
| 123 | L1-55 | CH$_2$ | 1 | |
| 124 | L1-56 | CH$_2$ | 1 | |
| 125 | L1-57 | CH$_2$ | 1 | |
| 126 | L1-58 | CH$_2$ | 1 | |
| 127 | L1-59 | CH$_2$ | 1 | |
| 128 | L1-60 | CH$_2$ | 1 | |
| 129 | L1-61 | CH$_2$ | 1 | |
| 130 | L1-62 | CH$_2$ | 1 | |
| 131 | L1-63 | CH$_2$ | 1 | |
| 132 | L1-64 | CH$_2$ | 1 | |
| 133 | L1-65 | CH$_2$ | 1 | |
| 134 | L1-66 | CH$_2$ | 1 | |
| 135 | L1-67 | CH$_2$ | 1 | |
| 136 | L1-68 | CH$_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-29 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |

TABLE 8-continued

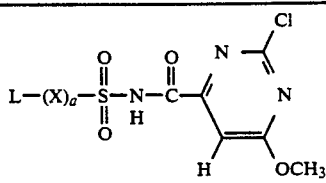

| Ex. No. | L | X | a | m.p. [°C.] |
|---|---|---|---|---|
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 229 | L1-15 | NH | 1 | |
| 220 | L1-16 | NH | 1 | |
| 221 | L1-17 | NH | 1 | |
| 222 | L1-18 | NH | 1 | |
| 223 | L1-29 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |

TABLE 8-continued

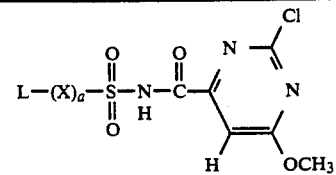

| Ex. No. | L | X | a | m.p. [°C.] |
|---|---|---|---|---|
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH$_2$ | 1 | |
| 299 | L4-2 | CH$_2$ | 1 | |
| 300 | L4-3 | CH$_2$ | 1 | |
| 301 | L4-4 | CH$_2$ | 1 | |
| 302 | L4-5 | CH$_2$ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |

TABLE 8-continued

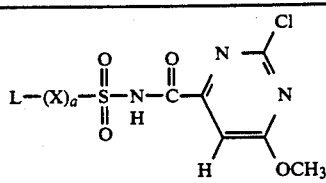

| Ex. No. | L | X | a | m.p. [°C.] |
|---|---|---|---|---|
| 316 | L5-4 | — | 0 | |
| 317 | L5-5 | — | 0 | |
| 318 | L5-6 | — | 0 | |
| 329 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-29 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH$_2$ | 1 | |
| 338 | L5-2 | CH$_2$ | 1 | |
| 339 | L5-3 | CH$_2$ | 1 | |
| 340 | L5-4 | CH$_2$ | 1 | |
| 341 | L5-5 | CH$_2$ | 1 | |
| 342 | L5-6 | CH$_2$ | 1 | |
| 343 | L5-7 | CH$_2$ | 1 | |
| 344 | L5-8 | CH$_2$ | 1 | |
| 345 | L5-9 | CH$_2$ | 1 | |
| 346 | L5-10 | CH$_2$ | 1 | |
| 347 | L5-11 | CH$_2$ | 1 | |
| 348 | L5-12 | CH$_2$ | 1 | |
| 349 | L5-13 | CH$_2$ | 1 | |
| 350 | L5-14 | CH$_2$ | 1 | |
| 351 | L5-15 | CH$_2$ | 1 | |
| 352 | L5-16 | CH$_2$ | 1 | |
| 353 | L5-17 | CH$_2$ | 1 | |
| 354 | L5-18 | CH$_2$ | 1 | |
| 355 | L5-29 | CH$_2$ | 1 | |
| 356 | L5-20 | CH$_2$ | 1 | |
| 357 | L5-21 | CH$_2$ | 1 | |
| 358 | L5-22 | CH$_2$ | 1 | |
| 359 | L5-23 | CH$_2$ | 1 | |
| 360 | L5-24 | CH$_2$ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-29 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |

TABLE 8-continued

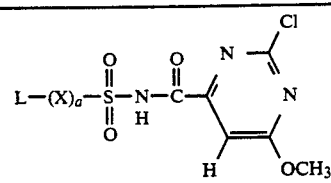

| Ex. No. | L | X | a | m.p. [°C.] |
|---|---|---|---|---|
| 388 | L5-4 | NH | 1 | |
| 389 | L5-5 | NH | 1 | |
| 390 | L5-6 | NH | 1 | |
| 391 | L5-7 | NH | 1 | |
| 392 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |
| 397 | L5-13 | NH | 1 | |
| 398 | L5-14 | NH | 1 | |
| 499 | L5-15 | NH | 1 | |
| 400 | L5-16 | NH | 1 | |
| 401 | L5-17 | NH | 1 | |
| 402 | L5-18 | NH | 1 | |
| 403 | L5-29 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 9

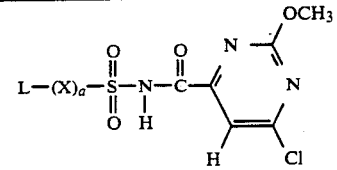

| Ex. No. | L | X | a | m.p. [°C.] |
|---|---|---|---|---|
| 1 | L1-1 | — | 0 | 124–126 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 29 | L1-29 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |

TABLE 9-continued

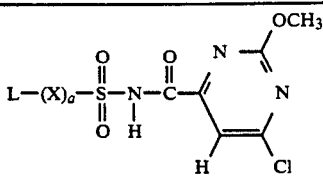

| Ex. No. | L | X | a | m.p. [°C.] |
|---|---|---|---|---|
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-55 | — | 0 | |
| 56 | L1-56 | — | 0 | |
| 57 | L1-57 | — | 0 | |
| 58 | L1-58 | — | 0 | |
| 59 | L1-59 | — | 0 | |
| 60 | L1-60 | — | 0 | |
| 61 | L1-61 | — | 0 | |
| 62 | L1-62 | — | 0 | |
| 63 | L1-63 | — | 0 | |
| 64 | L1-64 | — | 0 | |
| 65 | L1-65 | — | 0 | |
| 66 | L1-66 | — | 0 | |
| 67 | L1-67 | — | 0 | |
| 68 | L1-68 | — | 0 | |
| 69 | L1-1 | $CH_2$ | 1 | |
| 70 | L1-2 | $CH_2$ | 1 | |
| 71 | L1-3 | $CH_2$ | 1 | |
| 72 | L1-4 | $CH_2$ | 1 | |
| 73 | L1-5 | $CH_2$ | 1 | |
| 74 | L1-6 | $CH_2$ | 1 | |
| 75 | L1-7 | $CH_2$ | 1 | |
| 76 | L1-8 | $CH_2$ | 1 | |
| 77 | L1-9 | $CH_2$ | 1 | |
| 78 | L1-10 | $CH_2$ | 1 | |
| 79 | L1-11 | $CH_2$ | 1 | |
| 80 | L1-12 | $CH_2$ | 1 | |
| 81 | L1-13 | $CH_2$ | 1 | |
| 82 | L1-14 | $CH_2$ | 1 | |
| 83 | L1-15 | $CH_2$ | 1 | |
| 84 | L1-16 | $CH_2$ | 1 | |
| 85 | L1-17 | $CH_2$ | 1 | |
| 86 | L1-18 | $CH_2$ | 1 | |
| 87 | L1-29 | $CH_2$ | 1 | |
| 88 | L1-20 | $CH_2$ | 1 | |
| 89 | L1-21 | $CH_2$ | 1 | |
| 90 | L1-22 | $CH_2$ | 1 | |
| 91 | L1-23 | $CH_2$ | 1 | |
| 92 | L1-24 | $CH_2$ | 1 | |
| 93 | L1-25 | $CH_2$ | 1 | |
| 94 | L1-26 | $CH_2$ | 1 | |
| 95 | L1-27 | $CH_2$ | 1 | |
| 96 | L1-28 | $CH_2$ | 1 | |
| 97 | L1-29 | $CH_2$ | 1 | |
| 98 | L1-30 | $CH_2$ | 1 | |
| 99 | L1-31 | $CH_2$ | 1 | |
| 100 | L1-32 | $CH_2$ | 1 | |
| 101 | L1-33 | $CH_2$ | 1 | |
| 102 | L1-34 | $CH_2$ | 1 | |
| 103 | L1-35 | $CH_2$ | 1 | |
| 104 | L1-36 | $CH_2$ | 1 | |
| 105 | L1-37 | $CH_2$ | 1 | |
| 106 | L1-38 | $CH_2$ | 1 | |
| 107 | L1-39 | $CH_2$ | 1 | |
| 108 | L1-40 | $CH_2$ | 1 | |

TABLE 9-continued

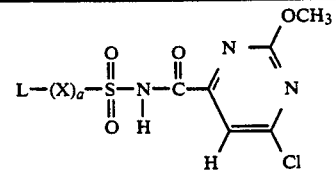

| Ex. No. | L | X | a | m.p. [°C.] |
|---|---|---|---|---|
| 109 | L1-41 | $CH_2$ | 1 | |
| 110 | L1-42 | $CH_2$ | 1 | |
| 111 | L1-43 | $CH_2$ | 1 | |
| 112 | L1-44 | $CH_2$ | 1 | |
| 113 | L1-45 | $CH_2$ | 1 | |
| 114 | L1-46 | $CH_2$ | 1 | |
| 115 | L1-47 | $CH_2$ | 1 | |
| 116 | L1-48 | $CH_2$ | 1 | |
| 117 | L1-49 | $CH_2$ | 1 | |
| 118 | L1-50 | $CH_2$ | 1 | |
| 129 | L1-51 | $CH_2$ | 1 | |
| 120 | L1-52 | $CH_2$ | 1 | |
| 121 | L1-53 | $CH_2$ | 1 | |
| 122 | L1-54 | $CH_2$ | 1 | |
| 123 | L1-55 | $CH_2$ | 1 | |
| 124 | L1-56 | $CH_2$ | 1 | |
| 125 | L1-57 | $CH_2$ | 1 | |
| 126 | L1-58 | $CH_2$ | 1 | |
| 127 | L1-59 | $CH_2$ | 1 | |
| 128 | L1-60 | $CH_2$ | 1 | |
| 129 | L1-61 | $CH_2$ | 1 | |
| 130 | L1-62 | $CH_2$ | 1 | |
| 131 | L1-63 | $CH_2$ | 1 | |
| 132 | L1-64 | $CH_2$ | 1 | |
| 133 | L1-65 | $CH_2$ | 1 | |
| 134 | L1-66 | $CH_2$ | 1 | |
| 135 | L1-67 | $CH_2$ | 1 | |
| 136 | L1-68 | $CH_2$ | 1 | |
| 137 | L1-1 | O | 1 | |
| 138 | L1-2 | O | 1 | |
| 139 | L1-3 | O | 1 | |
| 140 | L1-4 | O | 1 | |
| 141 | L1-5 | O | 1 | |
| 142 | L1-6 | O | 1 | |
| 143 | L1-7 | O | 1 | |
| 144 | L1-8 | O | 1 | |
| 145 | L1-9 | O | 1 | |
| 146 | L1-10 | O | 1 | |
| 147 | L1-11 | O | 1 | |
| 148 | L1-12 | O | 1 | |
| 149 | L1-13 | O | 1 | |
| 150 | L1-14 | O | 1 | |
| 151 | L1-15 | O | 1 | |
| 152 | L1-16 | O | 1 | |
| 153 | L1-17 | O | 1 | |
| 154 | L1-18 | O | 1 | |
| 155 | L1-29 | O | 1 | |
| 156 | L1-20 | O | 1 | |
| 157 | L1-21 | O | 1 | |
| 158 | L1-22 | O | 1 | |
| 159 | L1-23 | O | 1 | |
| 160 | L1-24 | O | 1 | |
| 161 | L1-25 | O | 1 | |
| 162 | L1-26 | O | 1 | |
| 163 | L1-27 | O | 1 | |
| 164 | L1-28 | O | 1 | |
| 165 | L1-29 | O | 1 | |
| 166 | L1-30 | O | 1 | |
| 167 | L1-31 | O | 1 | |
| 168 | L1-32 | O | 1 | |
| 169 | L1-33 | O | 1 | |
| 170 | L1-34 | O | 1 | |
| 171 | L1-35 | O | 1 | |
| 172 | L1-36 | O | 1 | |
| 173 | L1-37 | O | 1 | |
| 174 | L1-38 | O | 1 | |
| 175 | L1-39 | O | 1 | |
| 176 | L1-40 | O | 1 | |
| 177 | L1-41 | O | 1 | |
| 178 | L1-42 | O | 1 | |
| 179 | L1-43 | O | 1 | |
| 180 | L1-44 | O | 1 | |

TABLE 9-continued

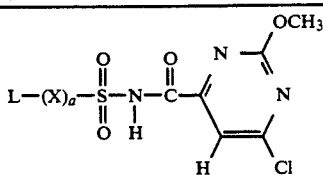

| Ex. No. | L | X | a | m.p. [°C.] |
|---|---|---|---|---|
| 181 | L1-45 | O | 1 | |
| 182 | L1-46 | O | 1 | |
| 183 | L1-47 | O | 1 | |
| 184 | L1-48 | O | 1 | |
| 185 | L1-49 | O | 1 | |
| 186 | L1-50 | O | 1 | |
| 187 | L1-51 | O | 1 | |
| 188 | L1-52 | O | 1 | |
| 189 | L1-53 | O | 1 | |
| 190 | L1-54 | O | 1 | |
| 191 | L1-55 | O | 1 | |
| 192 | L1-56 | O | 1 | |
| 193 | L1-57 | O | 1 | |
| 194 | L1-58 | O | 1 | |
| 195 | L1-59 | O | 1 | |
| 196 | L1-60 | O | 1 | |
| 197 | L1-61 | O | 1 | |
| 198 | L1-62 | O | 1 | |
| 199 | L1-63 | O | 1 | |
| 200 | L1-64 | O | 1 | |
| 201 | L1-65 | O | 1 | |
| 202 | L1-66 | O | 1 | |
| 203 | L1-67 | O | 1 | |
| 204 | L1-68 | O | 1 | |
| 205 | L1-1 | NH | 1 | |
| 206 | L1-2 | NH | 1 | |
| 207 | L1-3 | NH | 1 | |
| 208 | L1-4 | NH | 1 | |
| 209 | L1-5 | NH | 1 | |
| 210 | L1-6 | NH | 1 | |
| 211 | L1-7 | NH | 1 | |
| 212 | L1-8 | NH | 1 | |
| 213 | L1-9 | NH | 1 | |
| 214 | L1-10 | NH | 1 | |
| 215 | L1-11 | NH | 1 | |
| 216 | L1-12 | NH | 1 | |
| 217 | L1-13 | NH | 1 | |
| 218 | L1-14 | NH | 1 | |
| 229 | L1-15 | NH | 1 | |
| 220 | L1-16 | NH | 1 | |
| 221 | L1-17 | NH | 1 | |
| 222 | L1-18 | NH | 1 | |
| 223 | L1-29 | NH | 1 | |
| 224 | L1-20 | NH | 1 | |
| 225 | L1-21 | NH | 1 | |
| 226 | L1-22 | NH | 1 | |
| 227 | L1-23 | NH | 1 | |
| 228 | L1-24 | NH | 1 | |
| 229 | L1-25 | NH | 1 | |
| 230 | L1-26 | NH | 1 | |
| 231 | L1-27 | NH | 1 | |
| 232 | L1-28 | NH | 1 | |
| 233 | L1-29 | NH | 1 | |
| 234 | L1-30 | NH | 1 | |
| 235 | L1-31 | NH | 1 | |
| 236 | L1-32 | NH | 1 | |
| 237 | L1-33 | NH | 1 | |
| 238 | L1-34 | NH | 1 | |
| 239 | L1-35 | NH | 1 | |
| 240 | L1-36 | NH | 1 | |
| 241 | L1-37 | NH | 1 | |
| 242 | L1-38 | NH | 1 | |
| 243 | L1-39 | NH | 1 | |
| 244 | L1-40 | NH | 1 | |
| 245 | L1-41 | NH | 1 | |
| 246 | L1-42 | NH | 1 | |
| 247 | L1-43 | NH | 1 | |
| 248 | L1-44 | NH | 1 | |
| 249 | L1-45 | NH | 1 | |
| 250 | L1-46 | NH | 1 | |
| 251 | L1-47 | NH | 1 | |
| 252 | L1-48 | NH | 1 | |

TABLE 9-continued

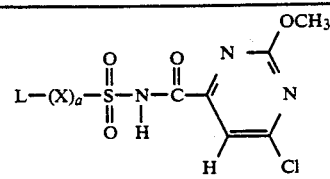

| Ex. No. | L | X | a | m.p. [°C.] |
|---|---|---|---|---|
| 253 | L1-49 | NH | 1 | |
| 254 | L1-50 | NH | 1 | |
| 255 | L1-51 | NH | 1 | |
| 256 | L1-52 | NH | 1 | |
| 257 | L1-53 | NH | 1 | |
| 258 | L1-54 | NH | 1 | |
| 259 | L1-55 | NH | 1 | |
| 260 | L1-56 | NH | 1 | |
| 261 | L1-57 | NH | 1 | |
| 262 | L1-58 | NH | 1 | |
| 263 | L1-59 | NH | 1 | |
| 264 | L1-60 | NH | 1 | |
| 265 | L1-61 | NH | 0 | |
| 266 | L1-62 | NH | 0 | |
| 267 | L1-63 | NH | 1 | |
| 268 | L1-64 | NH | 1 | |
| 269 | L1-65 | NH | 1 | |
| 270 | L1-66 | NH | 1 | |
| 271 | L1-67 | NH | 1 | |
| 272 | L1-68 | NH | 1 | |
| 273 | L3-1 | — | 0 | |
| 274 | L3-2 | — | 0 | |
| 275 | L3-3 | — | 0 | |
| 276 | L3-4 | — | 0 | |
| 277 | L3-5 | — | 0 | |
| 278 | L3-1 | CH$_2$ | 1 | |
| 279 | L3-2 | CH$_2$ | 1 | |
| 280 | L3-3 | CH$_2$ | 1 | |
| 281 | L3-4 | CH$_2$ | 1 | |
| 282 | L3-5 | CH$_2$ | 1 | |
| 283 | L3-1 | O | 1 | |
| 284 | L3-2 | O | 1 | |
| 285 | L3-3 | O | 1 | |
| 286 | L3-4 | O | 1 | |
| 287 | L3-5 | NH | 1 | |
| 288 | L3-1 | NH | 1 | |
| 289 | L3-2 | NH | 1 | |
| 290 | L3-3 | NH | 1 | |
| 291 | L3-4 | NH | 1 | |
| 292 | L3-5 | NH | 1 | |
| 293 | L4-1 | — | 0 | |
| 294 | L4-2 | — | 0 | |
| 295 | L4-3 | — | 0 | |
| 296 | L4-4 | — | 0 | |
| 297 | L4-5 | — | 0 | |
| 298 | L4-1 | CH$_2$ | 1 | |
| 299 | L4-2 | CH$_2$ | 1 | |
| 300 | L4-3 | CH$_2$ | 1 | |
| 301 | L4-4 | CH$_2$ | 1 | |
| 302 | L4-5 | CH$_2$ | 1 | |
| 303 | L4-1 | O | 1 | |
| 304 | L4-2 | O | 1 | |
| 305 | L4-3 | O | 1 | |
| 306 | L4-4 | O | 1 | |
| 307 | L4-5 | O | 1 | |
| 308 | L4-1 | NH | 1 | |
| 309 | L4-2 | NH | 1 | |
| 310 | L4-3 | NH | 1 | |
| 311 | L4-4 | NH | 1 | |
| 312 | L4-5 | NH | 1 | |
| 313 | L5-1 | — | 0 | |
| 314 | L5-2 | — | 0 | |
| 315 | L5-3 | — | 0 | |
| 316 | L5-4 | — | 0 | |
| 317 | L5-5 | — | 0 | |
| 318 | L5-6 | — | 0 | |
| 329 | L5-7 | — | 0 | |
| 320 | L5-8 | — | 0 | |
| 321 | L5-9 | — | 0 | |
| 322 | L5-10 | — | 0 | |
| 323 | L5-11 | — | 0 | |
| 324 | L5-12 | — | 0 | |

TABLE 9-continued

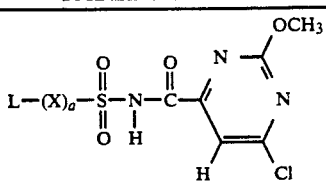

| Ex. No. | L | X | a | m.p. [°C.] |
|---|---|---|---|---|
| 325 | L5-13 | — | 0 | |
| 326 | L5-14 | — | 0 | |
| 327 | L5-15 | — | 0 | |
| 328 | L5-16 | — | 0 | |
| 329 | L5-17 | — | 0 | |
| 330 | L5-18 | — | 0 | |
| 331 | L5-29 | — | 0 | |
| 332 | L5-20 | — | 0 | |
| 333 | L5-21 | — | 0 | |
| 334 | L5-22 | — | 0 | |
| 335 | L5-23 | — | 0 | |
| 336 | L5-24 | — | 0 | |
| 337 | L5-1 | CH$_2$ | 1 | |
| 338 | L5-2 | CH$_2$ | 1 | |
| 339 | L5-3 | CH$_2$ | 1 | |
| 340 | L5-4 | CH$_2$ | 1 | |
| 341 | L5-5 | CH$_2$ | 1 | |
| 342 | L5-6 | CH$_2$ | 1 | |
| 343 | L5-7 | CH$_2$ | 1 | |
| 344 | L5-8 | CH$_2$ | 1 | |
| 345 | L5-9 | CH$_2$ | 1 | |
| 346 | L5-10 | CH$_2$ | 1 | |
| 347 | L5-11 | CH$_2$ | 1 | |
| 348 | L5-12 | CH$_2$ | 1 | |
| 349 | L5-13 | CH$_2$ | 1 | |
| 350 | L5-14 | CH$_2$ | 1 | |
| 351 | L5-15 | CH$_2$ | 1 | |
| 352 | L5-16 | CH$_2$ | 1 | |
| 353 | L5-17 | CH$_2$ | 1 | |
| 354 | L5-18 | CH$_2$ | 1 | |
| 355 | L5-29 | CH$_2$ | 1 | |
| 356 | L5-20 | CH$_2$ | 1 | |
| 357 | L5-21 | CH$_2$ | 1 | |
| 358 | L5-22 | CH$_2$ | 1 | |
| 359 | L5-23 | CH$_2$ | 1 | |
| 360 | L5-24 | CH$_2$ | 1 | |
| 361 | L5-1 | O | 1 | |
| 362 | L5-2 | O | 1 | |
| 363 | L5-3 | O | 1 | |
| 364 | L5-4 | O | 1 | |
| 365 | L5-5 | O | 1 | |
| 366 | L5-6 | O | 1 | |
| 367 | L5-7 | O | 1 | |
| 368 | L5-8 | O | 1 | |
| 369 | L5-9 | O | 1 | |
| 370 | L5-10 | O | 1 | |
| 371 | L5-11 | O | 1 | |
| 372 | L5-12 | O | 1 | |
| 373 | L5-13 | O | 1 | |
| 374 | L5-14 | O | 1 | |
| 375 | L5-15 | O | 1 | |
| 376 | L5-16 | O | 1 | |
| 377 | L5-17 | O | 1 | |
| 378 | L5-18 | O | 1 | |
| 379 | L5-29 | O | 1 | |
| 380 | L5-20 | O | 1 | |
| 381 | L5-21 | O | 1 | |
| 382 | L5-22 | O | 1 | |
| 383 | L5-23 | O | 1 | |
| 384 | L5-24 | O | 1 | |
| 385 | L5-1 | NH | 1 | |
| 386 | L5-2 | NH | 1 | |
| 387 | L5-3 | NH | 1 | |
| 388 | L5-4 | NH | 1 | |
| 389 | L5-5 | NH | 1 | |
| 390 | L5-6 | NH | 1 | |
| 391 | L5-7 | NH | 1 | |
| 392 | L5-8 | NH | 1 | |
| 393 | L5-9 | NH | 1 | |
| 394 | L5-10 | NH | 1 | |
| 395 | L5-11 | NH | 1 | |
| 396 | L5-12 | NH | 1 | |

TABLE 9-continued

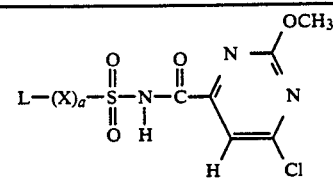

| Ex. No. | L | X | a | m.p. [°C.] |
|---|---|---|---|---|
| 397 | L5-13 | NH | 1 | |
| 398 | L5-14 | NH | 1 | |
| 499 | L5-15 | NH | 1 | |
| 400 | L5-16 | NH | 1 | |
| 401 | L5-17 | NH | 1 | |
| 402 | L5-18 | NH | 1 | |
| 403 | L5-29 | NH | 1 | |
| 404 | L5-20 | NH | 1 | |
| 405 | L5-21 | NH | 1 | |
| 406 | L5-22 | NH | 1 | |
| 407 | L5-23 | NH | 1 | |
| 408 | L5-24 | NH | 1 | |

TABLE 10

Examples of salts with bases

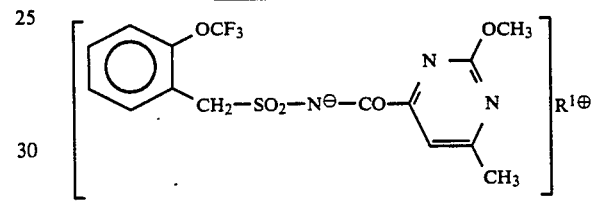

| Ex. No. | R$^1$ | m.p. [°C.] |
|---|---|---|
| 1 | Na | 188–189 (dec.) |
| 2 | K | 251–253 |
| 3 | (C$_2$H$_5$)$_3$NH | Oil |
| 4 | [CH(CH$_3$)$_2$]$_2$NH$_2$ | 108–111 |
| 5 | Li | 227–229 |

TABLE 11

Examples of acid addition salts

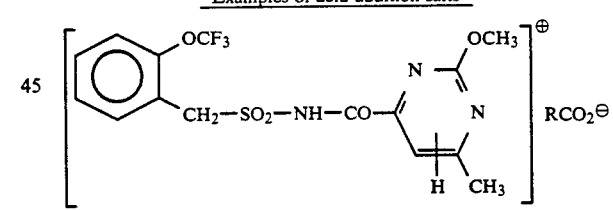

| Ex. No. | R | m.p. [°C.] |
|---|---|---|
| 1 | CH$_3$ | 88–95 |
| 2 | n-C$_{15}$H$_{31}$ | 114–116 |

TABLE 12

Examples of intermediates of the formula III
(R$^1$ = H; X = CH$_2$; a = 1)

L—CH$_2$—SO$_2$—NH$_2$

| Ex. No. | L | m.p. [°C.] |
|---|---|---|
| 1 | L 5-1 | |
| 2 | L 5-2 | |
| 3 | L 5-3 | |
| 4 | L 5-4 | |
| 5 | L 5-5 | |
| 6 | L 5-6 | 245–246 (dec.) |
| 7 | L 5-7 | 126–128 |
| 8 | L 5-8 | 160 |
| 9 | L 5-9 | |
| 10 | L 5-10 | |

TABLE 12-continued

Examples of intermediates of the formula III
($R^1 = H$; $X = CH_2$; $a = 1$)

L—$CH_2$—$SO_2$—$NH_2$

| Ex. No. | L | m.p. [°C.] |
|---|---|---|
| 11 | L 5-11 | |
| 12 | L 5-12 | |
| 13 | L 5-13 | |
| 14 | L 5-14 | |
| 15 | L 5-15 | |
| 16 | L 5-16 | |
| 17 | L 5-17 | |
| 18 | L 5-18 | |
| 19 | L 5-19 | |
| 20 | L 5-20 | |
| 21 | L 5-21 | |
| 22 | L 5-22 | |
| 23 | L 5-23 | |
| 24 | L 5-24 | |
| 25 | L 5-25 | 165–168 |
| 26 | L 5-26 | |
| 27 | L 5-27 | |
| 28 | L 5-28 | |
| 29 | L 5-29 | |

C. Biological examples
1. Herbicidal action

The damage to the wed plants or the tolerability of the cultivated plants was assessed according to a key in which the activity is expressed by numerical values from 0–5. The figures have the following meaning:

0 = without action or damage
1 = 0–20% action or damage
2 = 20–40% action or damage
3 = 40–60% action or damage
4 = 60–80% action or damage
5 = 80–100% action or damage.

1.1 Weed action pre-emergence

Seeds or pieces of rhizome from mono- and dicotyledon weed plants were planted in sandy loam soil in plastic pots and covered with soil. The compounds according t the invention formulated in the form of wettable powders or emulsion concentrates were then applied to the surface of the covering soil in different dosages as aqueous suspensions or emulsions with a water application rate of 600–800 l/ha in converted form.

After treatment, the pots were placed in a greenhouse and kept under good growing conditions for the weeds. The plant or emergence damage was visually assessed in comparison to untreated controls after the emergence of the test plants after a test period of 3–4 weeks.

As the assessment values in Table 13 show, the compounds according to the invention have a good herbicidal pre-emergence activity against a wide spectrum of weed grasses and weeds.

TABLE 13

Herbicidal action of the compounds according to the invention pre-emergence

| Table | Ex. No. | Dose (kg a.s./ha) | STME | CRSE | SIAL | LOMU | ECCR | AVSA |
|---|---|---|---|---|---|---|---|---|
| 2 | 1 | 0,3 | 5 | 2 | 5 | 5 | 3 | 1 |
| 2 | 28 | 0,3 | 4 | 3 | 5 | 3 | 5 | 1 |
| 2 | 37 | 0,3 | 3 | 2 | 5 | 3 | 2 | 1 |
| 2 | 8 | 0,3 | 5 | 5 | 5 | 5 | 3 | 3 |
| 2 | 76 | 0,3 | 5 | 5 | 5 | 4 | 3 | 2 |
| 2 | 16 | 0,3 | 5 | 3 | 5 | 2 | 2 | 3 |
| 2 | 69 | 0,3 | 5 | 5 | 5 | 2 | 5 | 3 |
| 2 | 212 | 0,3 | 4 | 5 | 4 | 3 | 4 | 3 |
| 2 | 122 | 0,3 | 4 | 5 | 4 | 4 | 4 | 3 |
| 2 | 44 | 0,3 | 5 | 5 | 5 | 5 | 5 | 4 |
| 2 | 35 | 0,3 | 5 | 4 | 3 | 4 | 3 | 1 |
| 2 | 96 | 0,3 | 4 | 4 | 4 | 3 | 2 | 3 |
| 2 | 54 | 0,3 | 5 | 5 | 5 | 4 | 2 | 1 |
| 4 | 8 | 0,3 | 4 | 5 | 5 | 3 | 2 | 0 |
| 4 | 76 | 0,3 | 5 | 5 | 5 | 5 | 5 | 1 |
| 3 | 127 | 0,3 | 5 | 5 | 5 | 2 | 3 | 3 |
| 4 | 122 | 0,3 | 5 | 5 | 5 | 5 | 5 | 1 |
| 4 | 1 | 0,3 | 3 | 1 | 5 | 1 | 1 | 1 |
| 4 | 44 | 0,3 | 5 | 5 | 5 | 5 | 5 | 1 |
| 4 | 96 | 0,3 | 5 | 5 | 5 | 5 | 4 | 3 |
| 4 | 69 | 0,3 | 5 | 5 | 5 | 5 | 5 | 4 |
| 4 | 26 | 0,3 | 4 | 5 | 5 | 4 | 3 | 3 |
| 4 | 94 | 0,3 | 5 | 5 | 5 | 5 | 5 | 3 |
| 7 | 8 | 0,3 | 5 | 5 | 5 | 3 | 3 | 2 |
| 4 | 127 | 0,3 | 5 | 5 | 5 | 2 | 2 | 1 |
| 2 | 15 | 0,3 | 4 | 2 | 3 | 2 | 2 | 1 |
| 7 | 76 | 0,3 | 5 | 5 | 5 | 5 | 5 | 2 |
| 4 | 28 | 0,3 | 4 | 3 | 4 | 4 | 3 | 3 |
| 4 | 112 | 0,3 | 2 | 2 | 5 | 1 | 1 | 1 |
| 7 | 26 | 0,3 | 5 | 5 | 5 | 4 | 4 | 2 |
| 7 | 122 | 0,3 | 5 | 5 | 5 | 5 | 5 | 3 |
| 7 | 1 | 0,3 | 1 | 2 | 4 | 2 | 2 | 2 |
| 4 | 121 | 0,3 | 5 | 5 | 5 | 5 | 5 | 3 |
| 4 | 53 | 0,3 | 3 | 3 | 3 | 3 | 2 | 3 |
| 5 | 76 | 0,3 | 3 | 4 | 5 | 2 | 3 | 2 |
| 5 | 96 | 0,3 | 5 | 3 | 5 | 3 | 2 | 3 |
| 5 | 8 | 0,3 | 1 | 2 | 2 | 2 | 2 | 1 |
| 2 | 53 | 0,3 | 5 | 5 | 5 | 5 | 2 | 2 |
| 6 | 28 | 0,3 | 2 | 3 | 2 | 2 | 2 | 3 |
| 6 | 76 | 0,3 | 5 | 5 | 5 | 5 | 5 | 3 |
| 4 | 84 | 0,3 | 5 | 5 | 5 | 5 | 5 | 4 |
| 4 | 83 | 0,3 | 5 | 5 | 5 | 5 | 5 | 4 |
| 6 | 8 | 0,3 | 5 | 4 | 5 | 4 | 4 | 3 |
| 3 | 28 | 0,3 | 5 | 4 | 5 | 3 | 5 | 2 |

TABLE 13-continued

| | | | Herbicidal action of the compounds according to the invention pre-emergence | | | | | | |
|---|---|---|---|---|---|---|---|---|---|
| | | Dose | | | herbicidal action | | | | |
| Table | Ex. No. | (kg a.s./ha) | STME | CRSE | SIAL | LOMU | ECCR | AVSA | |
| 3 | 84 | 0,3 | 5 | 5 | 5 | 4 | 4 | 3 | |
| 3 | 76 | 0,3 | 5 | 4 | 4 | 3 | 4 | 3 | |
| 3 | 8 | 0,3 | 5 | 5 | 5 | 3 | 5 | 3 | |
| 6 | 122 | 0,3 | 5 | 5 | 5 | 5 | 5 | 4 | |
| 4 | 343 | 0,3 | 5 | 5 | 5 | 5 | 5 | 5 | |
| 4 | 230 | 0,3 | 4 | 4 | 4 | 5 | 2 | 2 | |
| 4 | 342 | 0,3 | 5 | 5 | 5 | 5 | 5 | 5 | |
| 6 | 121 | 0,3 | 5 | 5 | 5 | 5 | 5 | 3 | |
| 6 | 69 | 0,3 | 5 | 5 | 5 | 5 | 5 | 3 | |
| 6 | 94 | 0,3 | 4 | 5 | 5 | 5 | 4 | 3 | |
| 6 | 1 | 0,3 | 3 | 4 | 4 | 2 | 3 | 3 | |
| 6 | 26 | 0,3 | 3 | 5 | 5 | 4 | 4 | 3 | |
| 4 | 106 | 0,3 | 5 | 5 | 5 | 5 | 5 | 3 | |
| 6 | 84 | 0,3 | 5 | 5 | 5 | 3 | 5 | 2 | |
| 4 | 258 | 0,3 | 3 | 5 | 5 | 2 | 1 | 2 | |
| 7 | 69 | 0,3 | 2 | 5 | 3 | 2 | 4 | 1 | |
| 4 | 129 | 0,3 | 5 | 5 | 5 | 5 | 5 | 2 | |
| 10 | 1 | 0,3 | 5 | 5 | 5 | 5 | 5 | 2 | |
| 10 | 2 | 0,3 | 4 | 5 | 5 | 5 | 3 | 2 | |
| 10 | 3 | 0,3 | 5 | 5 | 5 | 5 | 3 | 3 | |
| 10 | 4 | 0,3 | 5 | 5 | 5 | 5 | 3 | 3 | |
| 11 | 1 | 0,3 | 5 | 5 | 5 | 5 | 3 | 3 | |
| 11 | 2 | 0,3 | 4 | 5 | 5 | 5 | 3 | 3 | |
| 10 | 5 | 0,3 | 5 | 5 | 5 | 5 | 3 | 2 | |
| 4 | 120 | 0,3 | 5 | 5 | 5 | 5 | 5 | 2 | |
| 6 | 83 | 0,3 | 4 | 5 | 5 | 3 | 5 | 3 | |

Abbreviations:
STME = *Stellaria media*
CRSE = *Chrysanthemum segetum*
SIAL = *Sinapis alba*
LOMU = *Lolium multiflorum*
ECCR = *Echinochloa crus-galli*
AVSA = *Avena sativa*
a.s. = active substance 1.2 Weed action in post-emergence Seeds or pieces of rhizome from mono- and dicotyledon weeds were [lacuna] in sandy loam soil in plastic pots, covered with soil and placed in a greenhouse under good growing conditions. Three weeks after sowing, the test plants were treated in the three-leaf stage.

The compounds according to the invention formulated as wettable powders or as emulsion concentrates were sprayed onto the green plant parts in various dosages with a water application rate of 600–800 l/ha in converted form and, after a standing period of the test plants in the greenhouse under optimum growing conditions, as [sic] action of the preparations was assessed visually in comparison to untreated controls.

The agents according to the invention also have a good herbicidal activity, post-emergence against a wide spectrum of economically important weed grasses and weeds (Table 14).

TABLE 14

| | | Herbicidal action of the compound [sic] according to the invention post-emergence | | | | | | |
|---|---|---|---|---|---|---|---|---|
| | | Dose | | | herbicidal action | | | |
| Table | Ex. No. | (kg a.s./ha) | STME | CRSE | SIAL | LOMU | ECCR | AVSA |
| 2 | 26 | 0,3 | 5 | 5 | 5 | 2 | 3 | 0 |
| 2 | 1 | 0,3 | 5 | 5 | 5 | 5 | 5 | 2 |
| 2 | 38 | 0,3 | 5 | 5 | 5 | 3 | 3 | 2 |
| 2 | 28 | 0,3 | 3 | 5 | 4 | 3 | 4 | 1 |
| 2 | 37 | 0,3 | 4 | 1 | 4 | 3 | 2 | 1 |
| 2 | 94 | 0,3 | 3 | 5 | 4 | 2 | 1 | 1 |
| 2 | 8 | 0,3 | 5 | 4 | 5 | 5 | 3 | 2 |
| 2 | 76 | 0,3 | 4 | 5 | 5 | 4 | 2 | 2 |
| 2 | 16 | 0,3 | 4 | 3 | 5 | 1 | 3 | 1 |
| 2 | 69 | 0,3 | 4 | 3 | 5 | 2 | 4 | 1 |
| 2 | 122 | 0,3 | 2 | 4 | 4 | 4 | 1 | 1 |
| 2 | 44 | 0,3 | 3 | 2 | 5 | 4 | 3 | 1 |
| 2 | 35 | 0,3 | 5 | 4 | 4 | 2 | 2 | 1 |
| 2 | 93 | 0,3 | 5 | 3 | 4 | 1 | 1 | 2 |
| 2 | 220 | 0,3 | 5 | 5 | 4 | 2 | 2 | 2 |
| 2 | 96 | 0,3 | 3 | 2 | 4 | 1 | 1 | 2 |
| 2 | 54 | 0,3 | 4 | 3 | 5 | 4 | 1 | 2 |
| 4 | 8 | 0,3 | 3 | 5 | 5 | 2 | 1 | 1 |
| 4 | 76 | 0,3 | 5 | 5 | 5 | 5 | 5 | 1 |
| 2 | 127 | 0,3 | 5 | 5 | 5 | 1 | 4 | 1 |
| 4 | 122 | 0,3 | 5 | 5 | 5 | 5 | 4 | 1 |
| 4 | 1 | 0,3 | 4 | 3 | 4 | 1 | 0 | 0 |
| 4 | 44 | 0,3 | 5 | 4 | 5 | 5 | 2 | 0 |

TABLE 14-continued

Herbicidal action of the compound [sic] according to the invention post-emergence

| Table | Ex. No. | Dose (kg a.s./ha) | STME | CRSE | SIAL | LOMU | ECCR | AVSA |
|---|---|---|---|---|---|---|---|---|
| 4 | 96 | 0,3 | 4 | 4 | 5 | 3 | 3 | 2 |
| 4 | 69 | 0,3 | 5 | 5 | 5 | 3 | 5 | 2 |
| 4 | 26 | 0,3 | 3 | 5 | 5 | 2 | 3 | 1 |
| 4 | 94 | 0,3 | 5 | 5 | 5 | 2 | 3 | 2 |
| 4 | 127 | 0,3 | 5 | 5 | 5 | 1 | 2 | 1 |
| 2 | 15 | 0.3 | 4 | 0 | 5 | 1 | 0 | 1 |
| 7 | 76 | 0.3 | 3 | 5 | 5 | 3 | 4 | 1 |
| 4 | 28 | 0,3 | 2 | 1 | 4 | 1 | 1 | 0 |
| 4 | 112 | 0,3 | 2 | 2 | 5 | 0 | 3 | 3 |
| 7 | 26 | 0,3 | 5 | 4 | 5 | 4 | 3 | 2 |
| 7 | 122 | 0,3 | 5 | 5 | 5 | 5 | 3 | 2 |
| 7 | 1 | 0,3 | 2 | 2 | 4 | 1 | 2 | 2 |
| 4 | 121 | 0,3 | 5 | 5 | 5 | 5 | 4 | 2 |
| 4 | 53 | 0,3 | 4 | 5 | 0 | 0 | 3 | 2 |
| 5 | 76 | 0,3 | 2 | 3 | 4 | 0 | 3 | 1 |
| 5 | 96 | 0,3 | 2 | 2 | 4 | 0 | 3 | 2 |
| 5 | 8 | 0,3 | 3 | 2 | 5 | 1 | 3 | 2 |
| 2 | 53 | 0,3 | 1 | 4 | 5 | 1 | 1 | 0 |
| 6 | 28 | 0,3 | 2 | 4 | 4 | 0 | 3 | 1 |
| 6 | 76 | 0.3 | 5 | 5 | 5 | 5 | 5 | 3 |
| 4 | 84 | 0,3 | 5 | 5 | 5 | 5 | 4 | 2 |
| 4 | 83 | 0,3 | 5 | 5 | 5 | 5 | 5 | 2 |
| 6 | 8 | 0,3 | 4 | 5 | 5 | 4 | 5 | 2 |
| 3 | 28 | 0,3 | 4 | 5 | 5 | 3 | 4 | 2 |
| 3 | 84 | 0,3 | 4 | 4 | 5 | 2 | 2 | 2 |
| 3 | 76 | 0,3 | 5 | 4 | 4 | 2 | 3 | 2 |
| 3 | 8 | 0,3 | 3 | 4 | 5 | 2 | 4 | 1 |
| 6 | 122 | 0,3 | 5 | 5 | 5 | 5 | 4 | 3 |
| 4 | 343 | 0,3 | 5 | 5 | 5 | 5 | 5 | 4 |
| 4 | 230 | 0,3 | 2 | 4 | 3 | 1 | 2 | 2 |
| 4 | 342 | 0,3 | 5 | 5 | 5 | 5 | 5 | 4 |
| 6 | 121 | 0,3 | 5 | 5 | 5 | 5 | 4 | 2 |
| 6 | 69 | 0,3 | 3 | 5 | 5 | 5 | 4 | 3 |
| 6 | 94 | 0,3 | 3 | 5 | 5 | 2 | 3 | 2 |
| 6 | 1 | 0,3 | 2 | 4 | 5 | 2 | 2 | 2 |
| 6 | 26 | 0,3 | 4 | 5 | 5 | 3 | 4 | 2 |
| 4 | 106 | 0,3 | 3 | 5 | 5 | 3 | 4 | 2 |
| 6 | 84 | 0,3 | 3 | 5 | 5 | 2 | 4 | 1 |
| 4 | 258 | 0,3 | 3 | 4 | 3 | 2 | 3 | 2 |
| 7 | 69 | 0,3 | 3 | 3 | 4 | 3 | 4 | 2 |
| 4 | 129 | 0,3 | 5 | 5 | 5 | 5 | 5 | 3 |
| 10 | 1 | 0,3 | 5 | 5 | 5 | 5 | 3 | 1 |
| 10 | 2 | 0,3 | 5 | 5 | 5 | 5 | 3 | 1 |
| 10 | 3 | 0,3 | 5 | 5 | 5 | 5 | 4 | 1 |
| 10 | 4 | 0,3 | 5 | 5 | 5 | 5 | 4 | 1 |
| 11 | 1 | 0,3 | 5 | 5 | 5 | 5 | 4 | 1 |
| 11 | 2 | 0,3 | 5 | 5 | 5 | 4 | 3 | 1 |
| 10 | 5 | 0,3 | 5 | 5 | 5 | 5 | 5 | 1 |
| 4 | 120 | 0,3 | 4 | 5 | 5 | 3 | 2 | 2 |
| 6 | 83 | 0,3 | 3 | 5 | 4 | 1 | 2 | 2 |

Abbreviations:
STME = *Stellaria media*
CRSE = *Chrysanthemum segetum*
SIAL = *Sinapis alba*
LOMU = *Lolium multiflorum*
ECCR = *Echinochloa crus-galli*
AVSA = *Avena sativa*
a.s. = active substance 2. Fungicidal action Barley plants were heavily inoculated in the 2-leaf stage with barley mildew conidia (Erysiphe graminis hordei) and cultivated further in a greenhouse at 20° C. and a relative atmospheric humidity of about 50%. 1 day after inoculation, the plants were uniformly wetted with the compounds shown in Table 15 in the active compound concentrations indicated. After an incubation period of 7-9 days, the plants were examined for attack by barley mildew. The degree of attack is expressed in % of attached leaf surface, relative to untreated infected control plants (=100% attack). The result is summarized in Table 15.

TABLE 15

Fungicidal action against barley mildew

| Compounds according to Table/Example | Leaf surface attacked by barley mildew in % at 500 or 250 mg of active compound/liter of spray liquor | |
|---|---|---|
| | 500 | 250 |
| 10/1 | 0 | 0 |
| 10/2 | 0 | 0 |
| 10/3 | 0 | 0 |
| 10/4 | 0 | 0 |
| 11/1 | 0 | 0 |
| 11/2 | 0 | 0 |
| 10/5 | 0 | 0 |
| Control with untreated | | 100 |

TABLE 15-continued

| Fungicidal action against barley mildew | | |
|---|---|---|
| Compounds according to Table/Example | Leaf surface attacked by barley mildew in % at 500 or 250 mg of active compound/liter of spray liquor | |
| | 500 | 250 |
| infected plants | | |

We claim:

1. A compound of the formula I or its salts

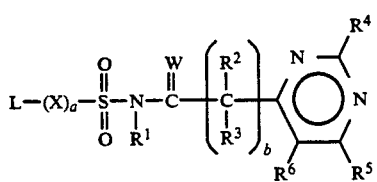
(I)

in which

R[1] is hydrogen, ($C_1$-$C_4$)alkyl, ($C_2$-$C_6$)alkenyl or ($C_2$-$C_6$)-alkynyl;

R[2], R[3] independently of one another are hydrogen, ($C_1$-$C_3$)-alkyl or phenyl;

W is O, S, NR[7] or NOR[7];

X is CHR[2], O, NR[7] or NOR[7];

R[4], R[5] independently of one another are hydrogen, hydroxyl, halogen, ($C_1$-$C_6$)alkyl, ($C_1$-$C_6$)alkoxy or ($C_1$-$C_6$)alkylthio, where the three abovementioned radicals can be monosubstituted or polysubstituted by halogen or monosubstituted or disubstituted by ($C_1$-$C_4$)alkoxy or ($C_1$-$C_4$)alkylthio; —NR[8]R[9], ($C_3$-$C_6$)-cycloalkyl, —OCHR[8]CO$_2$R[10], ($C_2$-$C_5$)alkenyl, ($C_2$-$C_4$)-alkynyl, ($C_3$-$C_5$)alkenyloxy or ($C_3$-$C_5$)alkynyloxy;

R[6] is hydrogen, halogen, ($C_1$-$C_3$)alkyl, ($C_1$-$C_3$)alkoxy, —CN, —NO$_2$, —CO—R[11], —CO$_2$R[12], ($C_1$-$C_3$)alkylthio, —SO—R[12], —SO$_2$—R[12] or —CO—NR[8]R[9];

R[7] is hydrogen, ($C_1$-$C_3$)alkyl, ($C_1$-$C_3$)haloalkyl or phenyl;

R[8] is hydrogen or ($C_1$-$C_4$)alkyl or R[8] and R[9] together are —(CH$_2$)$_2$(CH$_2$)$_c$(CH$_2$)$_2$— or —(CH$_2$)$_2$O(CH$_2$)$_2$—;

R[9] is hydrogen, ($C_1$-$C_4$)alkyl, ($C_1$-$C_4$)alkoxy, ($C_2$-$C_4$)alkenyl or R[8] and R[9] together are —(CH$_2$)$_2$—(CH$_2$)$_c$—(CH$_2$2— or —(CH$_2$)$_2$O(CH$_2$)$_2$—;

R[10] is hydrogen, ($C_1$-$C_4$)alkyl which is unsubstituted, or monosubstituted or polysubstituted by halogen or monosubstituted or disubstituted by CN, CO$_2$—R[12], —NR[8]R[9], OR[12] or Si(CH$_3$)$_3$; ($C_3$-$C_4$)alkynyl or ($C_3$-$C_4$)—alkenyl, where the two abovementioned radicals are unsubstituted or substituted by CH$_3$ or —Si(CH$_3$)$_3$; ($C_3$-$C_6$)cycloalkyl which is unsubstituted or substituted by ($C_1$-$C_4$)alkyl or ($C_1$-$C_4$)alkoxy; or Si(CH$_3$)$_3$;

R[11] is hydrogen, ($C_1$-$C_4$)alkyl, ($C_1$-$C_4$)alkyl which is monosubstituted or polysubstituted by halogen or ($C_1$-$C_3$)alkoxy; ($C_3$-$C_6$)cycloalkyl which is unsubstituted, or monosubstituted or polysubstituted by halogen or CH$_3$; ($C_2$-$C_4$)alkenyl or ($C_2$-$C_4$)alkynyl;

R[12] is ($C_1$-$C_3$)alkyl;

L is a hetero- or isocyclic radical of the formulae (L1) to (L5)

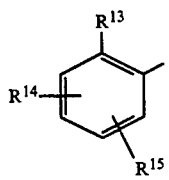
(L1)

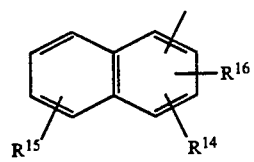
(L2)

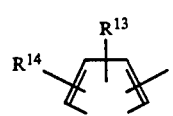
(L3)

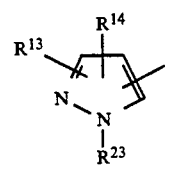
(L4)

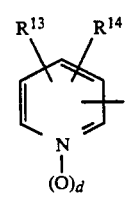
(L5)

R[13] is hydrogen, halogen, NO$_2$, CN, ($C_1$-$C_4$)alkyl which is unsubstituted, or monosubstituted or polysubstituted by halogen, or monosubstituted by CN, OCH$_3$ or SCH$_3$; ($C_2$-$C_4$)alkenyl which is unsubstituted, or monosubstituted or polysubstituted by halogen, or monosubstituted by OCH$_3$; ($C_2$-$C_4$)alkynyl which is unsubstituted, or monosubstituted or polysubstituted by halogen, or monosubstituted by OCH$_3$ or Si(CH$_3$)$_3$; ($C_3$-$C_6$)cycloalkyl which is unsubstituted, or monosubstituted or polysubstituted by halogen or CH$_3$; —CO—R[11], —OCH$_2$CH$_2$OR[11], —OH, —C(R[11])(OR[17])(OR[18]); —CO$_2$R[10], —CO—NR[8]R[9], —N$_3$, SO$_2$NR[8]R[9], —SO$_3$R[19], —OSO$_2$R[20]; phenyl which is unsubstituted, or monosubstituted or polysubstituted by halogen, CH$_3$ or OCH$_3$; E—R[21] or —(CH$_2$)$_e$—G;

R[14] is hydrogen, halogen; CN, NO$_2$, ($C_1$-$C_4$)alkyl which is unsubstituted, or monosubstituted or polysubstituted by halogen or monosubstituted or disubstituted by —CO$_2$R[10], —SO$_2$NR[8]R[9], —NR[8]R[9], ($C_1$-$C_2$)alkoxy, —E—R[22], ($C_1$-$C_2$)haloalkoxy, ($C_1$-$C_2$)alkylthio, ($C_1$-$C_2$)haloalkylthio, —CN, —OH or SH; —CO$_2$R[10], —SO$_2$NR[8]R[9], —NR[8]R[9] or —E—R[22];

R[15] is hydrogen, ($C_1$-$C_4$)alkyl, ($C_1$-$C_4$)haloalkyl, ($C_2$-$C_4$)-alkenyl, phenyl or phenyl which is monosubstituted or polysubstituted by halogen or —E—R[22]; —E—R[22] or halogen;

R[16] is hydrogen, ($C_1$-$C_4$)alkyl, ($C_1$-$C_4$)haloalkyl, halogen, —CO$_2$R[10], —SO$_2$NR[8]R[9], —OSO$_2$R[20], —E—R[22], —CN or —NO$_2$;

E, Z independently of one another are O or S(O)$_f$;

a, b, c, d, e independently of one another are 0 or 1;
f is 0, 1 or 2;
$R^{17}$, $R^{18}$ independently of one another are ($C_1$-$C_4$)alkyl, or $R^{17}$ and $R^{18}$ together are —$CH_2CH_2$—, —$CH_2OCH_2$— or —$CH_2$—$C(CH_3)_2CH_2$—;
$R^{19}$ is ($C_1$-$C_4$)alkyl or ($C_1$-$C_4$)haloalkyl,
$R^{20}$ is ($C_1$-$C_4$)alkyl, —$NR^8R^9$ or ($C_1$-$C_4$)haloalkyl,
$R^{21}$ is ($C_1$-$C_4$)alkyl, ($C_1$-$C_4$)haloalkyl, ($C_2$-$C_4$)alkoxyalkyl, ($C_2$-$C_4$)alkenyl, ($C_3$-$C_4$)alkynyl, phenyl or phenyl which is monosubstituted or polysubstituted by halogen, ($C_1$-$C_3$)alkyl, ($C_1$-$C_3$)alkoxy or ($C_1$-$C_3$)haloalkyl; or ($C_2$-$C_4$)haloalkenyl;
$R^{22}$ is ($C_1$-$C_4$)alkyl or ($C_1$-$C_4$)alkyl which is monosubstituted or polysubstituted by halogen or monosubstituted by $OR^{19}$;
$R^{23}$ is hydrogen, ($C_1$-$C_4$)alkyl which is unsubstituted, or monosubstituted or polysubstituted by halogen or monosubstituted by phenyl, or ($C_2$-$C_4$)alkenyl, phenyl or phenyl which is monosubstituted or polysubstituted by halogen, ($C_1$-$C_4$)alkyl, ($C_1$-$C_4$)haloalkyl, —$NO_2$, —CN or ($C_1$-$C_4$)alkoxy,
G is a heterocyclic radical from the group comprising (G1)–(G25);

(G1) 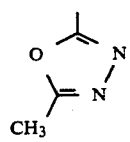

(G2) 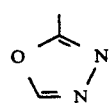

(G3) 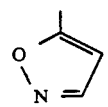

(G4) 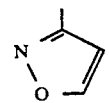

(G5) 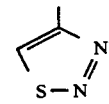

(G6) 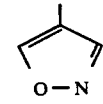

(G7) 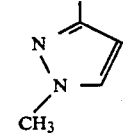

(G8) 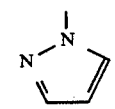

-continued (G9) 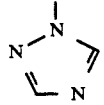

(G10) 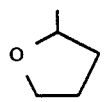

(G11) 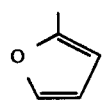

(G12) 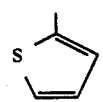

(G13) 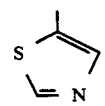

(G14) 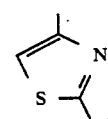

(G15) 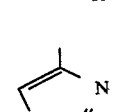

(G16) 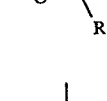

(G17) 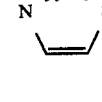

(G18) 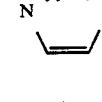

(G19) 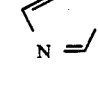

(G20) 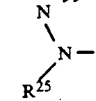

-continued

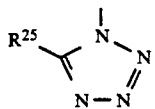
(G21)

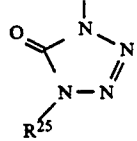
(G22)

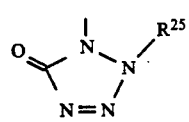
(G23)

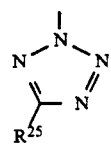
(G24)

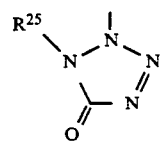
(G25)

and
$R^{24}$ is hydrogen or $(C_1-C_4)$alkyl;
$R^{25}$ is hydrogen, $(C_1-C_3)$alkyl or $(C_2-C_4)$alkenyl.

2. The compound or its salts as claimed i claim 1, wherein
L is a radical of the formulae (L1), (L3), (L4) or (L5);
X is $CH_2$, $CH(CH_3)$, O, NH, $NCH_3$, $NC_2H_5$, $NOCH_3$, in particular $CH_2$, O or NH;
W is oxygen;
$R^1$ is hydrogen;
$R^2$, $R^3$ independently of one another are hydrogen or $(C_1-C_3)$alkyl, in particular hydrogen;
$R^4$, $R^5$ independently of one another are hydrogen, $(C_1-C_2)$-alkyl, $(C_1-C_2)$alkoxy, $-OCH_2OCH_3$, $-CH_2OCH_3$, F, Cl, Br, I, $-CH_2OCH_2CH_3$, $-NHCH_3$, $-N(CH_3)_2$, $-N(CH_3)OCH_3$, $-CF_3$, $-SCH_3$, $-CH(OCH_3)_2$, $-OCH_2CH=CH_2$, $-OCH_2C\equiv CH$, $-OCH_2CH_2OC-H_3$, $-CH_2SCH_3$, $-OCHF_2$, $-SCHF_2$, cyclopropyl, $-C\equiv CH$ or $C\equiv C-CH_3$;
$R^6$ is hydrogen, halogen, $-CH_3$, $-OCH_3$, $-NO_2$, $-CN$, $-CHO$, $-CO_2CH_3$, $CO_2C_2H_5$ or $-SCH_3$
$R^8$ is hydrogen or $-CH_3$ or $R^8$ and $R^9$ together are $-(CH_2)_4-$, $-(CH_2)_5-$ or $-(CH_2)_2O(CH_2)_2-$;
$R^9$ is $-CH_3$, $-CH_2CH_3$, $-OCH_3$ or $R^8$ and $R^9$ together are $-(CH_2)_4-$, $-(CH_2)_5-$ or $-(CH_2)_2O(CH_2)_2-$;
$R^{10}$ is $(C_1-C_3)$alkyl, $(C_3)$alkenyl, $(C_3)$alkynyl, $-CH_2CH_2F$, $-CH_2CH_2Cl$, $-CH_2CH_2OCH_3$, $-CH_2CH_2Si(CH_3)_3$ or cyclopropylmethyl;
$R^{11}$ is $(C_1-C_3)$alkyl, hydrogen, cyclopropyl or $(C_3)$alkenyl;
$R^{12}$ is $-CH_3$, $-CH_2CH_3$, $-CH_2CH_2CH_3$ or $-CH(CH_3)_2$;
$R^{13}$ is halogen, $-NO_2$, $-CN$, $(C_1-C_3)$alkyl which is unsubstituted or substituted by F, Cl, Br, CN, $OCH_3$ or $SCH_3$; $(C_3)$alkenyl which is unsubstituted or substituted by F, Cl or Br, $(C_3)$alkynyl, cyclopropyl which is unsubstituted or substituted by F, Cl or $CH_3$; $-C(O)R^{11}$, $-OCH_2CH_2OR^{11}$, $-OH$, $C(R^{11})(OR^{17})(OR^{18})$, $-CO_2R^{10}$, $-CO-NR^8R^9$, $-N_3$, $-SO_2NR^8R^9$, $-OSO_2R^{20}$, $-E$ $-R^{21}$ or $-(CH_2)_eG$;
$R^{14}$ is hydrogen, halogen, $-CN$, $-NO_2$, $-CH_3$, $-CF_3$, $-E-R^{22}$, or $(C_1-C_2)$alkoxy—$(C_1-C_2)$alkyl, $-CO_2R^{10}$ or $SO_2NR^8R^9$;
$R^{15}$ is hydrogen;
$R^{17}$, $R^{18}$ independently of one another are $(C_1-C_2)$alkyl $R^{17}$ and $R^{18}$ together are $-CH_2CH_2-$;
$R^{20}$ is $(C_1-C_3)$alkyl or $(C_1-C_3)$haloalkyl;
$R^{21}$ is $(C_1-C_3)$alkyl, $(C_1-C_3)$haloalkyl, $(C_2-C_3)$alkoxyalkyl, allyl, propargyl or $(C_2-C_3)$haloalkenyl;
$R^{22}$ is $(C_1-C_2)$alkyl which is unsubstituted or substituted by F, Cl or $OCH_3$;
$R^{23}$ is hydrogen, $(C_1-C_3)$alkyl, phenyl or phenyl which is monosubstituted or polysubstituted by halogen, $-NO_2$, $(C_1-C_3)$alkyl, $(C_1-C_3)$haloalkyl or $(C_1-C_3)$alkoxy;
$R^{24}$ is hydrogen or $(C_1-C_3)$alkyl;
$R^{25}$ is hydrogen or $(C_1-C_3)$alkyl;
Z is S;
d is O;
e is O;
and E, a, b, f and G are as defined in claim 1.

3. The compound or its salts as claimed in claim 2, wherein $R^4$ and $R^5$ independently of one another are hydrogen, $CH_3$, $OCH_3$, $CH_2CH_3$, $OCH_2CH_3$, $OCHF_2$, $OCH_2OCH_3$, $CH_2OCH_3$, $NHCH_3$, $CH(OCH_3)_2$, Cl or cyclopropyl.

4. The compound or its salts as claimed in claim 2, wherein L is an isocyclic radical of the formula L1.

5. A method for controlling undesired plants or regulating the growth of plants, which comprises applying an effective amount of a compound of the formula I as defined in claim 1 as a herbicide or plant growth regulator.

6. The method as claimed in claim 5, wherein an effective amount of a compound of the formula I or its salts as defined in claim 1 is applied as a herbicide or plant growth regulator to the plants or to the soil in which the plants are cultivated 7. A herbicidal or plant growth regulating composition which comprises an effective amount of the compound of formula I or its salts as claimed in claim 1, and formulation auxiliaries.

8. The compound or its salts as claimed in claim 2, wherein $R^4$ and $R^5$ independently of one another are hydrogen, $CH_3$, $OCH_3$, $C_2CH_3$, $OCH_2CH_3$, $OCHF_2$, $OCH_2OCH_3$, $CH_2OCH_3$, $NHCH_2$, $CH(OCH_3)_2$, Cl or cyclopropyl.

9. The compound of formula I or its salt as claimed in claim 8, wherein L is a radical of the formula L1.

10. The compound of the formula I or its salt as claimed in claim 8, wherein L is a radical of the formula L3.

11. The compound of the formula I or its salt as claimed in claim 8, wherein L is a radical of the formula L4.

12. The compound of the formula I or its salt as claimed in claim 8, wherein L is a radical of the formula L5.

13. The compound of the formula I or its salt as claimed in claim 9, wherein
X is $CH_2$, O or NH,
a is 0 or 1,
$R^{13}$ is halogen, $NO_2$, $(C_1-C_3)$-alkyl which is unsubstituted or substituted by F or Cl, or is $CO_2R^{10}$, $SO_2NR^8R^9$, or $-E-R^{21}$, and
$R^{14}$ is hydrogen or methyl.

* * * * *